United States Patent [19]
Bender et al.

[11] Patent Number: 5,932,595
[45] Date of Patent: Aug. 3, 1999

[54] MATRIX METALLOPROTEASE INHIBITORS

[75] Inventors: Steven Lee Bender, Oceanside; Chris Allen Broka, Foster City; Jeffrey Allen Campbell, Fremont, all of Calif.; Arlindo Lucas Castelhano, New York, N.Y.; Lawrence Emerson Fisher, Mountain View; Robert Than Hendricks, Palo Alto, both of Calif.; Keshab Sarma, Sunnyvale, Calif.

[73] Assignees: Syntex (U.S.A.) Inc., Palo Alto; Agouron Pharmaceuticals, Inc., San Diego, both of Calif.

[21] Appl. No.: 08/769,049

[22] Filed: Dec. 18, 1996

Related U.S. Application Data

[60] Provisional application No. 60/022,439, Aug. 7, 1996, provisional application No. 60/008,939, Dec. 20, 1995, and provisional application No. 60/032,096, Dec. 4, 1996.

[51] Int. Cl.$^6$ .......................... A01N 43/40; A01N 43/36; A01N 37/10; C07C 415/00; C07C 233/00; C07D 211/08; C07D 207/00; C07D 333/32

[52] U.S. Cl. .......................... 514/317; 514/319; 514/327; 514/330; 514/331; 514/354; 514/357; 514/423; 514/438; 514/451; 514/565; 514/588; 514/595; 514/618; 514/625; 514/628; 514/825; 514/885; 514/900; 514/903; 546/192; 546/195; 546/225; 546/227; 546/229; 546/233; 546/235; 546/238; 546/239; 546/242; 546/245; 548/531; 548/537; 548/566; 548/572; 549/66; 549/71; 549/426; 549/427; 562/431; 562/452; 562/503; 562/504; 562/507; 562/555; 562/556; 564/42; 564/56; 564/57; 564/209; 564/224

[58] Field of Search .................................. 562/429, 427, 562/426, 431, 432, 503, 504, 507, 555, 556; 564/209, 224, 56, 57, 42; 546/192, 95, 227, 225, 229, 233, 235, 238, 239, 242, 245; 548/531, 537, 566, 572; 549/66, 71, 426, 427; 514/825, 900, 903, 885, 317, 319, 327, 330, 331, 354, 357, 423, 438, 451, 568, 588, 595, 618, 125, 628

[56] References Cited

U.S. PATENT DOCUMENTS

| | | | |
|---|---|---|---|
| 4,268,516 | 5/1981 | Lombardino et al. | 424/273 |
| 4,394,520 | 7/1983 | Kalopissis | 562/557 |
| 5,183,900 | 2/1993 | Galardy et al. | 548/495 |
| 5,189,178 | 2/1993 | Galardy et al. | 548/495 |
| 5,268,391 | 12/1993 | Hanson et al. | 514/616 |
| 5,475,013 | 12/1995 | Talley et al. | 514/311 |

FOREIGN PATENT DOCUMENTS

| | | |
|---|---|---|
| 0 276 436 A1 | 8/1988 | European Pat. Off. . |
| 0 438 223 A1 | 7/1991 | European Pat. Off. . |
| 0 606 046 | 7/1994 | European Pat. Off. . |
| 0 606 046 A1 | 7/1994 | European Pat. Off. . |
| 1 580 899 | 9/1969 | France . |
| 2 355 095 | 1/1978 | France . |
| WO90/05719 | 5/1990 | WIPO . |
| WO 92/06966 | 4/1992 | WIPO . |
| WO92/08688 | 5/1992 | WIPO . |
| WO 92/09563 | 6/1992 | WIPO . |
| WO 92/21360 | 12/1992 | WIPO . |
| WO93/20047 | 10/1993 | WIPO . |
| WO 94/25434 | 11/1994 | WIPO . |
| WO95/09841 | 4/1995 | WIPO . |
| WO95/29892 | 11/1995 | WIPO . |
| WO95/33731 | 12/1995 | WIPO . |
| WO96/06074 | 2/1996 | WIPO . |
| WO96/15096 | 5/1996 | WIPO . |
| WO97/24117 | 7/1997 | WIPO . |

OTHER PUBLICATIONS

Cas Registry Handbook: American Chemical Society, 1965–1971; RN: 331–89–5; 331–90–8; 331–93–1; 405–23–2; 780–95–0; 5463–52–5; 5464–62–0; 5445–04–5; 5445–05–6; 5460–58–2; 6803–08–3; 6534–37–8; 21056–72–4.

Clayton, et al., Tetrahedron, vol. 49:4, 1993, Oxford GB, pp. 939–946, "Direct Aromatic tert–Butylation during the Synthesis of Thiochroman–4–ones".

Chemical Abstracts, vol. 125:13, Sep. 23, 1996; abstract No. 167779x (for JP 08127581A, May 21, 1996.

Chemical Abstracts, vol. 93:19, Nov. 10, 1980; abstract No. 186144y (For JP 55027116A, Hokko Chemical Industry).

Chemical Abstracts, vol. 77:13, Sep. 25, 1972; abstract No. 88024j.

Rynbrandt, et al., Tetrahedron; Vol. 19, 1972, pp. 1937–1940, "The Oxidation of Aminocyclopropyl Sulfides".

Chemical Abstracts, vol. 76:21, May 22, 1972; abstract No. 126719d.

Katekar, et al., Aust. J. Chem.; vol. 25:3, 1972, pp. 647–653, "1–Thioisoflavanones and Related Compounds".

Chemical Abstracts, vol. 74:3, Jan. 18, 1971, abstract No. 13116v.

Dostert, et al., Helvetica Chimica Acta; vol. 53:7, 1970, pp. 1813–1827, "Synthese d'analogues partielment satures des neuroleptiques tricycliques clothiapine et octoclothepine".

Chemical Abstracts, vol. 69:19; Nov. 4, 1968, abstract No. 76817s (for Janczewski, et al., Ann. Univ. Mariae Curie–Sklodowska; Vol. 21, 1967, pp. 49–64).

Chemical Abstracts; Vol. 69:19, Nov. 4, 1968, abstract No. 75267a.

(List continued on next page.)

*Primary Examiner*—John Kight
*Assistant Examiner*—Raymond Covington
*Attorney, Agent, or Firm*—Rohan Peries

[57] ABSTRACT

The present invention relates to compounds of Formula I:

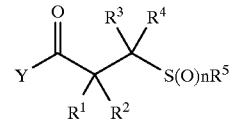

that are matrix metalloprotease inhibitors, pharmaceutical compositions containing them, methods for their use and methods of preparing these compounds.

60 Claims, No Drawings

OTHER PUBLICATIONS

Gillham, et al. Biochem. Journal; vol. 109:1, 1968, pp. 143–147, "The Isolation of Premercapturic Acids From the Urine of Animals does with Chlorobenzene and Bromobenzene".

Chemical Abstracts, vol. 67:15, Oct. 9, 1967, abstract No. 73477d.

Sen, et al., Journal Indian Chem. Soc.; vol. 43:7, 1966, pp. 521–525, "Synthesis of Potential Amoebacides. Part XXIV".

Chemical Astracts, vol. 67:9, Aug. 28, 1967; abstract No. 43615e.

Cagniant, et al., Bull. Soc. Chim. Fr., vol. 11, 1966, pp. 3674–3682, "Contributioni a l'etude des heterocycles sulfures condenses".

Chemical Abstracts, vol. 66:11, Mar. 13, 1967, abstract No. 46292n.

Degani, et al., Boll. Sci. Fac. Chim. Ind. Bologna, vol. 24:2–3, 1966, pp. 75–91, "Cationi eteroaromatici".

Chemical Abstracts, vol. 93:7, Aug. 18, 1980, abstract No. 61046m.

Johnson, et al., J. Enzyme Inhibition, vol. 2, 1987, pp. 1–22, "Collagenase Inhibitos: Their Design and Potential Therapeutic Use".

Sanquinetti, et al, CA 124 No. 8886 Method of Treating cardiac arrhythmia 1995.

Annunziata et al., CA 82 No. 170264 Acyloxyoxosulfonium intermediates, 1975.

Kindecher, CA 86 No. 94112 "Corrosion Protection of iron, 1976".

Chemical Abstract, vol. 109 No. 100759, Casadei et al., "Electrochemical Studies on Beta,–Lactams Part 3" (1988).

Chemical Abstracts vol. 123 No. 143709, Groutas et al, "The Gabriel–Colman Rearrangement in Biological Systems" (1975).

MATRIX METALLOPROTEASE INHIBITORS

CROSS-REFERENCE TO RELATED APPLICATIONS

This application claims the benefit under 35 U.S.C. 119(e) of U.S. Provisional application Nos. 60/022,439, filed Aug. 7, 1996; and 60/008,939, filed Dec. 20, 1995, and 60/032,096, filed Dec. 4, 1996.

FIELD OF THE INVENTION

The present invention relates to compounds, and their pharmaceutically acceptable salts and esters thereof, that inhibit matrix metalloproteases, particularly interstitial collagenases, and are therefore useful in the treatment of mammals having disease states alleviated by the inhibition of such matrix metalloproteases.

BACKGROUND INFORMATION AND RELATED DISCLOSURES

Matrix metalloproteases ("MMPs") are a family of proteases (enzymes) involved in the degradation and remodeling of connective tissues. Members of this family of endopeptidase enzymes are present in various cell types that reside in or are associated with connective tissue, such as fibroblasts, monocytes, macrophages, endothelial cells, and invasive or metastatic tumor cells. MMP expression is stimulated by growth factors and cytokines in the local tissue environment, where these enzymes act to specifically degrade protein components of the extracellular matrix, such as collagen, proteoglycans (protein core), fibronectin and laminin. These ubiquitous extracellular matrix components are present in the linings of joints, interstitial connective tissues, basement membranes, and cartilage. Excessive degradation of extracellular matrix by MMPs is implicated in the pathogenesis of many diseases, including rheumatoid arthritis, osteoarthritis, multiple sclerosis, chronic obstructive pulmonary disease, cerebral hemorrhaging associated with stroke, periodontal disease, aberrant angiogenesis, tumor invasion and metastasis, corneal ulceration, and in complications of diabetes. MMP inhibition is, therefore, recognized as a good target for therapeutic intervention.

The MMPs share a number of properties, including zinc and calcium dependence, secretion as zymogens, and 40–50% amino acid sequence homology. The MMP family currently consists of at least eleven enzymes, and includes collagenases, stromelysins, gelatinases, matrilysin, metalloelastase, and membrane-type MMP, as discussed in greater detail below.

Interstitial collagenases catalyze the initial and rate-limiting cleavage of native collagen types I, II, and III. Collagen, the major structural protein of mammals, is an essential component of the matrix of many tissues, for example, cartilage, bone, tendon and skin. Interstitial collagenases are very specific matrix metalloproteases which cleave these collagens to give two fragments which spontaneously denature at physiological temperatures and therefore become susceptible to cleavage by less specific enzymes. Cleavage by the collagenases results in the loss of structural integrity of the target tissue, essentially an irreversible process. There are currently three known human collagenases. The first is human fibroblast-type collagenase (HFC, MMP-1, or collagenase-1) that is produced by a wide variety of cells including fibroblasts and macrophages. The second is human neutrophil-type collagenase (HNC, MMP-8, or collagenase-2) that has so far only been demonstrated to be produced by neutrophils. The most recently discovered member of this group of MMPs is human collagenase-3 (MMP-13) which was originally found in breast carcinomas, but has since shown to be produced by chondrocytes. The only collagenase known to exist in rodents is the homolog of human collagenase-3.

The gelatinases include two distinct, but highly related, enzymes: a 72-kD enzyme (gelatinase A, HFG, MMP-2) secreted by fibroblasts and a wide variety of other cell types, and a 92-kD enzyme (gelatinase B, HNG, MMP-9) released by mononuclear phagocytes, neutrophils, corneal epithelial cells, tumor cells, cytotrophoblasts and keratinocytes. These gelatinases have been shown to degrade gelatins (denatured collagens), collagen types IV (basement membrane) and V, fibronectin and insoluble elastin.

Stromelysins 1 and 2 have been shown to cleave a broad range of matrix substrates, including laminin, fibronectin, proteoglycans, and collagen types IV and IX in their non-helical domains.

Matrilysin (MP-7, PUMP-1) has been shown to degrade a wide range of matrix substrates including proteoglycans, gelatins, fibronectin, elastin, and laminin. Its expression has been documented in mononuclear phagocytes, rat uterine explants and sporadically in tumors. Other less characterized MMPs include macrophage metalloelastase (MME, MMP-12), membrane type MMP (MMP-14), and stromelysin-3 (MMP-11).

Inhibitors of MEPs provide useful treatments for diseases associated with the excessive degradation of extracellular matrix, such as arthritic diseases (rheumatoid arthritis and osteoarthritis), multiple sclerosis, bone resorptive diseases (such as osteoporosis), the enhanced collagen destruction associated with diabetes, chronic obstructive pulmonary disease, cerebral hemorrhaging associated with stroke, periodontal disease, corneal or gastric ulceration, ulceration of the skin, tumor invasion and metastasis, and aberrant angiogenesis. The involvement of individual collagenases in the degradation of tissue collagens probably depends markedly on the tissue. The tissue distribution of human collagenases suggests that collagenase-3 is the major participant in the degradation of the collagen matrix of cartilage, while collagenase-1 is more likely to be involved in tissue remodeling of skin and other soft tissues. Thus, inhibitors selective for collagenase-3 over collagenase-1 are preferred for treatment of diseases associated with cartilage erosion, such as arthritis, etc.

Inhibitors of MMP also are known to substantially inhibit the release of tumor necrosis factor (TNF) from cells, and which therefore may be used in the treatment of conditions mediated by TNF. Such uses include, but are not limited to, the treatment of inflammation, fever, cardiovascular effects, hemorrhage, coagulation and acute phase response, cachexia and anorexia, acute infections, shock states, restinosis, aneurysmal disease, graft versus host reactions and autoimmune disease.

In addition to these effects on the release of TNF from cells, MMP inhibitors have also been shown to inhibit the release of other biologically active molecules from cells, including soluble receptors (CD30 and receptors for TNF (p55 and p75), IL-6, IL-1 and TSH), adhesion molecules (e.g., L-selection, ICAM-1, fibronectin) and other growth factors and cytokines, including Fas ligand, TGF-α, EGF, HB-EGF, SCF and M-CSF. Inhibition of the release or shedding of such proteins may be of benefit in a number of disease states, including rheumatoid arthritis, multiple sclerosis, vascular disease, Type II diabetes, HIV, cachexia, psoriasis, allergy, hepatitis, inflammatory bowel disease, and cancer.

Since non-specific inhibition of the shedding enzymes (sheddases) may have opposite pharmacological effects, selectivity will be a particular advantage, e.g., the inhibition of TNF release without the concurrent inhibition of TNF receptor release.

The design and uses of MMP inhibitors is described, for example, in *J. Enzyme Inhibition*, 2, 1–22 (1987); *Drug News & Prospectives*, 3 (8), 453–458 (1990); *Arthritis and Rheumatism*, 36(2), 181–189 (1993); *Arthritis and Rheumatism*, 34(9), 1073–1075 (1991); *Seminars in Arthritis and Rheumatism*, 19 (4), Supplement 1 (February), 16–20 (1990); *Drugs of the Future*, 15(5), 495–508 (1990); and *J. Enzyme Inhibition*, 2, 1–22 (1987). MMP inhibitors are also the subject of various patents and patent applications, for example, U.S. Pat. Nos. 5,189,178 and 5,183,900, European Published Patent Applications 438 223, 606 426, and 276 436, and Patent Cooperation Treaty International Applications 92/21360, 92/06966, 92/09563, and 94/25434.

SUMMARY OF THE INVENTION

One aspect of the invention concerns compounds represented by Formula I:

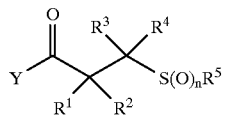

wherein:
n is 0, 1 or 2;
Y is hydroxy or XONH—, where X is hydrogen or lower alkyl;
$R^1$ is hydrogen or lower alkyl;
$R^2$ is hydrogen, lower alkyl, heteroalkyl, aryl, aralkyl, arylheteroalkyl, cycloalkyl, cycloalkylalkyl, heteroaryl, heteroaralkyl, heteroarylheteroalkyl, heterocyclo, heterocylo-lower alkyl, heterocyclo-lower heteroalkyl or —$NR^6R^7$, wherein:
  $R^6$ is hydrogen, lower alkyl, cycloalkyl or cycloalkylalkyl, aryl, heteroaryl and heteroaralkyl;
  $R^7$ is hydrogen, lower alkyl, cycloalkyl or cycloalkylalkyl, aryl, aralkyl, heteroaryl, heteroaralkyl, —$C(O)R^8$, —$C(O)NR^8R^9$, —$SO_2NR^8R^9$, —$SO_2R^{10}$, aryloxycarbonyl, or alkoxycarbonyl; or
  $R^6$ and $R^7$ together with the nitrogen atom to which they are attached represent a heterocyclo group; wherein
  $R^8$ and $R^9$ are independently hydrogen, lower alkyl, cycloalkyl, cycloalkylalkyl, aryl, aralkyl, heteroaryl, heteroaralkyl or heteroalkyl; and
  $R^{10}$ is lower alkyl, cycloalkyl, cycloalkylalkyl, aryl, aralkyl, heteroaryl, heteroaralkyl, heteroalkyl or heterocyclo; or
$R^1$ and $R^2$ together with the carbon atom to which they are attached represent a cycloalkyl or heterocyclo group;
$R^3$ is hydrogen, lower alkyl, cycloalkyl, cycloalkylalkyl, aryl, aralkyl, heteroaryl, heteroaralkyl, heteroalkyl or lower alkoxy;
$R^4$ is hydrogen, lower alkyl, cycloalkyl or cycloalkylalkyl; or
$R^2$ and $R^3$ together with the carbons to which they are attached represent a cycloalkyl or heterocyclo group; or $R^3$ and $R^4$ together with the carbon to which they are attached represent a cycloalkyl or heterocyclo group; and
$R^5$ is lower alkyl, cycloalkyl, cycloalkylalkyl, aryl, aralkyl, heteroaryl or heteroaralkyl;
or a pharmaceutically acceptable salt or ester thereof.

A second aspect of this invention relates to pharmaceutical compositions containing a therapeutically effective amount of a compound of Formula I or a pharmaceutically acceptable salt or ester thereof admixed with at least one pharmaceutically acceptable excipient.

A third aspect of this invention relates to methods for treating mammals having a disease state alleviated by the inhibition of matrix metalloproteases, by administering an effective amount of a compound of Formula I, or a pharmaceutical composition thereof, to the mammal. Such disease states include arthritic diseases, multiple sclerosis, bone resorption disease (such as osteoporosis), the enhanced collagen destruction associated with diabetes, chronic obstructive pulmonary disease, cerebral hemorrhaging associated with stroke, periodontal disease, corneal or gastric ulceration, ulceration of the skin, and tumor metastasis.

A fourth aspect of this invention relates to methods for preparing compounds of Formula I.

PREFERRED EMBODIMENTS

Among the family of compounds of the present invention, a preferred category includes the compounds of Formula I where n is 2 and Y is —NHOH.

Within this category, one preferred group includes the compounds where $R^1$ is hydrogen and $R^5$ is aryl. One preferred subgroup within this group includes the compounds where $R^2$ is hydrogen and $R^3$ is aralkyl, especially benzyl, and $R^4$ is hydrogen and $R^5$ is optionally substituted phenyl or naphthyl, more especially where $R^5$ is 4-methoxyphenyl, phenylthiophenyl, phenoxyphenyl or biphenyl. Another preferred subgroup within this group includes the compounds where $R^3$ and $R^4$ together with the carbon to which they are attached form a cycloalkyl group, especially cyclopentyl and cyclcohexyl, more especially where $R^5$ is 4-methoxyphenyl. Yet another preferred subgroup within this group includes the compounds where $R^3$ and $R^4$ together with the carbon to which they are attached form a heterocyclo group, in particular optionally substituted piperidinyl or tetrahydropyranyl, especially piperidin-4-yl, 1-methylpiperidin-4-yl, 1-(cyclopropylmethyl)piperidin-4-yl, or tetrahydropyranyl, more especially where $R^5$ is 4-phenoxyphenyl, 4-(4-chlorophenoxy)phenyl, or 4-(4-fluorophenoxy)phenyl.

Another preferred group within this category includes the compounds where $R^2$ is —$NR^6R^7$, $R^1$, $R^3$ and $R^4$ are hydrogen, and $R^5$ is aryl. One preferred subgroup within this group includes the compounds where $R^5$ is 4-phenoxyphenyl, 4-(4-chlorophenoxy)phenyl, or 4-(4-fluorophenoxy)phenyl, especially where $R^6$ is hydrogen and $R^7$ is CBZ-valinamido or valinamido.

Another preferred group within this category includes the compounds where $R^3$ and $R^4$ are hydrogen and $R^1$ and $R^2$ together with the carbon to which they are attached form a heterocyclo group, in particular optionally substituted piperidinyl or tetrahydropyranyl, especially piperidin-4-yl, 1-methylpiperidin-4-yl, 1-(cyclopropylmethyl)piperidin-4-yl, or most preferably tetrahydropyranyl, more especially where $R^5$ is 4-phenoxyphenyl, 4-(4-chlorophenoxy)phenyl, 4-(4-bromophenoxy)phenyl, 4-(4-fluorophenoxy)phenyl, 4-(thiophen-2-yl)phenoxy)phenyl, 4-(thiophen-3-yl)

phenoxy)phenyl, 4-(thiazol-2-yl)phenoxy)phenyl, 4-(2-pyridyloxy)phenyl, or 4-(5-chloro-2-pyridyloxy)phenyl.

At present, the preferred compounds are:

N-hydroxy-2-[4-(4-phenoxyphenylsulfonyl)-tetrahydropyran-4-yl]-acetamide;

2-{4-[4-(4-chlorophenoxy)-phenylsulfonyl]-tetrahydropyran-4-yl}-N-hydroxyacetamide;

2-{4-[4-(4-fluorophenoxy)-phenylsulfonyl]-tetrahydropyran-4-yl}-N-hydroxyacetamide;

N-hydroxy-2-[4-(4-phenoxyphenylsulfonyl)-piperidin-4-yl]-acetamide;

2-{4-[4-(4-chlorophenoxy)-phenylsulfonyl]-piperidin-4-yl}-N-hydroxyacetamide;

2-{4-[4-(4-fluorophenoxy)-phenylsulfonyl]-piperidin-4-yl}-N-hydroxyacetamide;

N-hydroxy-2-[1-methyl-4-(4-phenoxyphenylsulfonyl)-piperidin-4-yl]-acetamide;

N-hydroxy-2-{1-methyl-4-[4-(4-chlorophenoxy)-phenylsulfonyl]-piperidin-4-yl}-acetamide;

N-hydroxy-2-{1-methyl-4-[4-(4-fluorophenoxy)-phenylsulfonyl]-piperidin-4-yl}-acetamide;

2-[1-cyclopropylmethyl-4-(4-phenoxyphenylsulfonyl)-piperidin-4-yl]-N-hydroxyacetamide;

2-{1-cyclopropylmethyl-4-[4-(4-chlorophenoxy)-phenylsulfonyl]-piperidin-4-yl}-N-hydroxyacetamide;

2-{1-cyclopropylmethyl-4-[4-(4-fluorophenoxy)-phenylsulfonyl]-piperidin-4-yl}-N-hydroxyacetamide;

N-hydroxy-2-[4-(4-phenoxyphenylsulfinyl)-tetrahydropyran-4-yl]-acetamide;

2-{4-[4-(4-chlorophenoxy)-phenylsulfinyl]-tetrahydropyran-4-yl}-N-hydroxyacetamide;

2-{4-[4-(4-fluorophenoxy)-phenylsulfinyl]-tetrahydropyran-4-yl}-N-hydroxyacetamide;

N-hydroxy-2-[4-(4-phenoxyphenylthio)-tetrahydropyran-4-yl]-acetamide;

2-{4-[4-(4-chlorophenoxy)-phenylthio]-tetrahydropyran-4-yl}-N-hydroxyacetamide;

2-[4-[4-(4-fluorophenoxy)-phenylthio]-tetrahydropyran-4-yl}-N-hydroxyacetamide;

4-[4-(4-chlorophenoxy)phenylsulfonylmethyl]-tetrahydropyran-4-(N-hydroxycarboxamide);

4-[4-(4-bromophenoxy)phenylsulfonylmethyl]-tetrahydropyran-4-(N-hydroxycarboxamide);

4-[4-(4-fluorophenoxy)-phenylsulfonylmethyl]-tetrahydropyran-4-(N-hydroxycarboxamide);

3-[4-(4-chlorophenoxy)phenylsulfonyl]-2,2-dimethyl-N-hydroxypropionamide;

4-[4-(4-chlorophenoxy)phenylsulfonylmethyl]-1-(cyclopropylmethyl)piperidine-4-(N-hydroxycarboxamide);

4-[4-(4-chlorophenoxy)phenylsulfonylmethyl]-1-(nicotinoyl)piperidine-4-(N-hydroxycarboxamide);

4-[4-(phenoxy)phenylsulfonylmethyl]-tetrahydropyran-4-(N-hydroxycarboxamide);

4-[4-(4-(thiophen-2-yl)-phenoxy)phenylsulfonylmethyl]-tetrahydropyran-4-(N-hydroxycarboxamide);

4-[4-(4-(thiophen-3-yl)-phenoxy)phenylsulfonylmethyl]-tetrahydropyran-4-(N-hydroxycarboxamide);

4-[4-(4-(furan-2-yl)-phenoxy)phenylsulfonylmethyl]-tetrahydropyran-4-(N-hydroxycarboxamide);

4-[4-[4-(benzofuran-2-yl)-phenoxy)phenylsulfonylmethyl]-tetrahydropyran-4-(N-hydroxycarboxamide);

4-[4-(4-(thiazol-2-yl)-phenoxy)phenylsulfonylmethyl]-tetrahydropyran-4-(N-hydroxycarboxamide);

4-[4-(4-(thiazol-4-yl)-phenoxy)phenylsulfonylmethyl]-tetrahydropyran-4-(N-hydroxycarboxamide);

4-[4-(4-(thiazol-5-yl)-phenoxy)phenylsulfonylmethyl]-tetrahydropyran-4-(N-hydroxycarboxamide);

4-[4-(4-(imidazol-1-yl)-phenoxy)phenylsulfonylmethyl]-tetrahydropyran-4-(N-hydroxycarboxamide);

4-[4-(4-(imidazol-2-yl)-phenoxy)phenylsulfonylmethyl]-tetrahydropyran-4-(N-hydroxycarboxamide);

4-[4-(5-chloro-2-pyridyloxy)-phenylsulfonylmethyl]-tetrahydropyran-4-(N-hydroxycarboxamide);

3-[4-(5-chloro-2-pyridyloxy)phenylsulfonyl]-2,2-dimethyl-N-hydroxypropionamide.

DETAILED DESCRIPTION OF THE INVENTION

Definitions

The following definitions are set forth to illustrate and define the meaning and scope of the various terms used to describe the invention herein.

"Alkyl" means a branched or unbranched saturated hydrocarbon chain containing 1 to 8 carbon atoms, such as methyl, ethyl, propyl, tert-butyl, n-hexyl, n-octyl and the like.

"Lower alkyl" means a branched or unbranched saturated hydrocarbon chain containing 1 to 6 carbon atoms, such as methyl, ethyl, propyl, isopropyl, tert-butyl, n-butyl, n-hexyl and the like, unless otherwise indicated.

The term "heteroalkyl" refers to a branched or unbranched, cyclic or acyclic saturated organic radical containing carbon, hydrogen and one or more heteroatom containing substituents independently selected from $OR^a$, $NR^aR^b$, and $S(O)_nR^a$ (where n is 0, 1 or 2) and $R^a$ is hydrogen, alkyl, cycloalkyl, aryl, aralkyl, heteroaryl, heteroaralkyl or acyl, $R^b$ is hydrogen, alkyl, cycloalkyl, aryl, aralkyl, acyl, alkylsulfonyl, carboxamido, or mono- or di-alkylcarbamoyl. Representative examples include hydroxyalkyl, aminoalkyl, alkoxyalkyl, aryloxymethyl, N-acylaminoalkyl, thienylthiomethyl and the like.

"Acyl" refers to the group —C(O)—R', where R' is lower alkyl.

"Alkylene" refers to a straight chain or branched chain divalent radical consisting solely of carbon and hydrogen, containing no unsaturation and having from one to six carbon atoms, e.g., methylene, ethylene, propylene, 2-methylpropylene, butylene, 2-ethylbutylene, hexylene, and the like.

"Lower alkoxy" means the group —O—R', where R' is lower alkyl.

"Alkoxycarbonyl" means the group RO—C(O)— where R is alkyl as herein defined.

"Alkoxycarbonylalkyl" means the group ROC(O) $(CH_2)_n$— where R is alkyl as herein defined and n is 1, 2 or 3.

"Aryl" refers to a monovalent aromatic carbocyclic radical having a single ring (e.g., phenyl) or two condensed rings (e.g., naphthyl), which can optionally be mono-, di- or tri-substituted, independently, with hydroxy, carboxy, lower alkyl, cycloalkyl, cycloalkyloxy, lower alkoxy, chloro, fluoro, trifluoromethyl and/or cyano. The ring(s) can alternatively be optionally monosubstituted with the group $R^a$—Z—, where Z is oxygen, sulfur, —CH═CH—, —$CH_2$, carbonyl, a covalent bond, or nitrogen optionally substituted with lower alkyl, and $R^a$ is a monovalent aromatic carbocyclic, heteroaryl or heterocyclo radical, or a combination thereof, having 1 or 2 rings, for example phenyl, pyridyl, thienyl, imidazolyl, furanyl, pyrimidinyl, benzothiophene, azanaphthalene, indolyl, phenyl-(furan-2-yl), phenyl-(thien-2-yl), phenyl-(thien-3-yl), phenyl-(imidazol-2-yl), phenyl-(thiazol-2-yl), phenyl-(morpholin-2-yl), and phenyl-(oxazol-2-yl), (the ring(s) represented by $R^a$ being optionally mono- or disubstituted by hydroxy, carboxy, lower alkyl, lower alkoxy, halo, trifluoromethyl and/or cyano). Examples of aryl substituted by $R^a$—Z— are benzoyl, diphenylmethane, biphenyl, 6-methoxybiphenyl, 4-(4-methylphenoxy)phenyl, 4-phenoxyphenyl, 2-thiophenoxyphenyl, 4-pyridethenylphenyl, 4-(thiophen-2-yl)phenoxyphenyl, 4-(thiophen-3-yl)phenoxyphenyl, 4-(2-pyridyloxy)phenyl, 4-(5-chloro-2-pyridyloxy)phenyl, 4-(thiazol-5-yl)phenoxyphenyl, 4-(imidazol-2-yl)phenoxyphenyl, and the like.

"Heteroaryl" refers to a monovalent aromatic carbocyclic radical having one or two rings incorporating one, two or three heteroatoms (chosen from N, O or S) within the ring(s), such as thiazole, oxazole, imidazole, thiophene, quinolyl, benzofuranyl, pyridyl, and indolyl, which can optionally be mono-, di- or tri-substituted, independently, with OH, COOH, lower alkyl, lower alkoxy, halo, trifluoromethyl and/or cyano.

"Aralkyl" refers to a radical of the formula $R^b$—$R^c$—, wherein $R^b$ is aryl as defined above and $R^c$ is alkylene as defined above, for example benzyl, phenylethylene, 3-phenylpropyl, biphenylpropyl.

"Benzyloxycarbonyl" refers to a radical of the formula $R^d$CH$_2$OC(O)—, where $R^d$ is phenyl. "Benzyloxycarbonylamino" refers to a radical of the formula $R^d$CH$_2$OC(O)NH—, where $R^d$ is phenyl.

"Cycloalkyl" means a saturated monovalent monocyclic hydrocarbon radical containing 3–8 carbon atoms, such as cyclopropyl, cyclobutyl, cyclopentyl, cyclohexyl, cycloheptyl and cyclooctyl.

"Cycloalkylalkyl" means cycloalkyl as defined above attached to an alkylene radical as defined above.

"Halo" refers to bromo, chloro or fluoro.

"Heteroaralkyl" refers to a radical of the formula $R^e R^c$—, where $R^e$ is heteroaryl as defined above and $R^c$ is alkylene as defined above.

"Heterocyclo" refers to a monovalent saturated carbocyclic radical, consisting of either a 5 to 7 membered monocyclic ring or a 9 to 14 membered bicyclic ring, substituted by one, two or three heteroatoms chosen from N, O, or S, optionally fused to a substituted or unsubstituted benzene ring. Examples of heterocyclo radicals are morpholino, piperazinyl, piperidinyl, pyrrolidinyl, tetrahydrothiopyranyl, tetrahydrothiopyranyl-1,1-dioxide, tetrahydropyranyl, and the like, which can be optionally substituted by one or more substituents independently selected from lower alkyl, lower alkoxy, alkylamino, alkylaminoalkyl, acyl valyl, alkylsulfonyl, dialkylamino, heteroaroyl, alkoxycarbonylalkyl, and an amino protecting group where appropriate (e.g. CBZ, for example, 1-CBZ-piperidin-4-yl). However, the definition "$R^6$ and $R^7$ together with the nitrogen to which they are attached represent a heterocyclo group" clearly can refer only to a heterocyclo group containing at least one nitrogen atom.

"Hydroxylamino" refers to the group —NHOH.

"BOC" refers to tert-butoxycarbonyl.

"CBZ" refers to benzyloxycarbonyl (carbobenzyloxy).

"DCC" refers to 1,3-dicyclohexylcarbodiimide.

"Valine amide" refers to the radical (CH$_3$)$_2$CHCH(NH$_2$)C(O)NH—.

"Optional" or "optionally" means that the subsequently described event of circumstances may or may not occur, and that the description includes instances where said event or circumstance occurs and instances in which it does not. For example, "optionally substituted phenyl or aryl" means that the phenyl or aryl moiety may or may not be substituted and that the description includes both substituted and unsubstituted phenyl. The phrase "optional pharmaceutical excipients" indicates that a composition or dosage form so described may or may not include pharmaceutical excipients other than those specifically stated to be present, and that the formulation or dosage form so described includes instances in which optional excipients are present and instances in which they are not.

"Amino-protecting group" as used herein refers to those organic groups intended to protect nitrogen atoms against undesirable reactions during synthetic procedures, and includes, but is not limited to, benzyl, acyl, benzyloxycarbonyl (carbobenzyloxy), p-methoxybenzyloxy-carbonyl, p-nitrobenzyloxycarbonyl, tert-butoxycarbonyl, trifluoroacetyl, and the like.

"Base" as used here includes both strong inorganic bases such as sodium hydroxide, lithium hydroxide, ammonium hydroxide, potassium carbonate and the like, and organic bases such as pyridine, diisopropylethylamine, 4-methylmorpholine, triethylamine, dimethylaminopyridine and the like.

"Pharmaceutically acceptable salt" refers to those salts which retain the biological effectiveness and properties of the free bases or free acids and which are not biologically or otherwise undesirable. If the compound exists as a free base, the desired acid salt may be prepared by methods known to those of ordinary skill in the art, such as treatment of the compound with an inorganic acids such as hydrochloric acid, hydrobromic acid, sulfuric acid, nitric acid, phosphoric acid and the like; or with an organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. If the compound exists as a free acid, the desired base salt may also be prepared by methods known to those of ordinary skill in the art, such as the treatment of the compound with an inorganic base or an organic base. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

"Pharmaceutically acceptable ester" as used herein refers for example to those non-toxic esters of a compound of Formula I where $R^1$ is hydroxy, and are formed by reaction of such compounds, by means well known in the art, with an appropriate alkanol of 1–8 carbon atoms, for example methanol, ethanol, n-propanol, isopropanol, n-butanol, tert-butanol, i-butanol (or 2-methylpropanol), n-pentanol, n-hexanol, and the like.

The terms "inert organic solvent" or "inert solvent" mean a solvent inert under the conditions of the reaction being described in conjunction therewith, including, for example, benzene, toluene, acetonitrile, tetrahydrofuran ("THF"), N,N-dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like. Unless specified to the contrary, the solvents used in the reactions of the present invention are inert solvents.

The compounds of this invention may possess one or more asymmetric centers; such compounds can therefore be produced as mixtures of stereoisomers or as individual (R)- or (S)-stereoisomers. The individual enantiomers may be obtained by resolving a racemic or non-racemic mixture of an intermediate at some appropriate stage of the synthesis. It is understood that the individual (R)- or (S)-stereoisomers as well as racemic mixtures and other mixtures of stereoisomers are encompassed within the scope of the present invention.

The use of the symbol "(R)" or "(S)" preceding a substituent designates the absolute stereochemistry of that substituent according to the Cahn-Ingold-Prelog rules [see Cahn et al., *Angew. Chem. Inter. Edit.*, 5, 385 (1966), errata p. 511; Cahn et al., *Angew. Chem.*, 78, 413 (1966); Cahn and Ingold, *J. Chem. Soc.*, (London), 612 (1951); Cahn et al., *Experientia*, 12, 81 (1956); Cahn J., *Chem. Educ.*, 41, 116 (1964)]. Because of the interrelation of the designated substituent with the other substituents in a compound having α or β prefixes, the designation of the absolute configuration of one substituent fixes the absolute configuration of all substituents in the compound and thus the absolute configuration of the compound as a whole.

"Stereoisomers" are isomers that differ only in the way the atoms are arranged in space.

"Enantiomers" are a pair of stereoisomers that are non-superimposable mirror images of each other. Enantiomers rotate the plane of polarized light in opposite directions. The enantiomer that rotates the plane to the left is called the levo isomer, and is designated (−). The enantiomer that rotates the plane to the right is called the dextro isomer, and is designated (+).

"Diastereoisomers" are stereoisomers which are not mirror-images of each other.

"Racemic mixture" means a mixture containing equal parts of individual enantiomers. "Non-racemic mixture" is a mixture containing unequal parts of individual enantiomers.

"Mammal" includes humans and all domestic and wild animals, including, without limitation, cattle, horses, swine, sheep, goats, dogs, cats, and the like.

"Treating" or "treatment" as used herein cover the treatment of a disease-state in a mammal, particularly in a human, and include:
 (i) preventing the disease-state from occurring in a mammal, in particular, when such mammal is predisposed to the disease-state but has not yet been diagnosed as having it;
 (ii) inhibiting the disease-state, i.e., arresting its development; or
 (iii) relieving the disease-state, i.e., causing regression of the disease-state.

The term "therapeutically effective amount" refers to that amount of a compound of Formula I that is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

Nomenclature

The compounds of Formula I, illustrated below, will be named using the indicated numbering system:

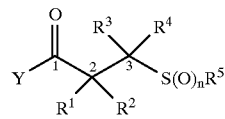

A compound of Formula I wherein is Y is N-hydroxylamino; $R^1$ and $R^2$ are hydrogen; $R^3$ is benzyl; $R^4$ is hydrogen; $R^5$ is 4-methoxyphenyl; and n is 2, is named 3-benzyl-3-(4-methoxyphenylsulfonyl)-N-hydroxypropion-amide.

A compound of Formula I wherein Y is N-hydroxylamino; $R^1$ and $R^2$ are hydrogen; $R^3$ and $R^4$ together with the carbon to which they are attached represent tetrahydropyran-4-yl; $R^5$ is 4-(4-fluorophenoxy)phenyl; and n is 2, is named as an acetic acid derivative, i.e., 2-{4-[4-(4-fluorophenoxy)-phenylsulfonyl]-tetrahydropyran-4-yl}-N-hydroxyacetamide.

A compound of Formula I wherein Y is hydroxy; $R^1$ is hydrogen; $R^2$ is methyl; $R^3$ and $R^4$ together with the carbon to which they are attached represent 1-methylpiperidin-4-yl; $R^5$ is biphenyl; and n is 1, is named 2-[4-(biphenyl-4-sulfinyl)-1-methylpiperidin-4-yl]-propionic acid.

A compound of Formula I wherein Y is N-hydroxylamino; $R^1$ and $R^2$ together with the carbon to which they are attached represent tetrahydropyran-4-yl, $R^3$ and $R^4$ are hydrogen, $R^5$ is 4-(4-chlorophenoxy)phenyl; and n is 2, is named 4-[4-(4-chlorophenoxy)phenylsulfonyl-methyl]-tetrahydropyran-4-(N-hydroxycarboxamide).

Synthetic Reaction Parameters

Unless specified to the contrary, the reactions described herein take place at atmospheric pressure within a temperature range from 5° C. to 100° C. (preferably from 10° C. to 50° C.; most preferably at "room" or "ambient" temperature, e.g., 20° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Amide couplings used to form the compounds of Formula I are generally performed by the carbodiimide method with reagents such as 1,3-dicyclohexylcarbodiimide or N'-ethyl-N'-(3-dimethylaminopropyl)carbodiimide hydrochloride or alternatively 1-(3-dimethylaminopropyl)-3-ethylcarbodiimide hydrochloride (EDCI), in the presence of 1-hydroxybenzotriazole hydrate (HOBT) in an inert solvent such as N,N-dimethylformamide (DMF) or methylene chloride (CH$_2$Cl$_2$). Other methods of forming the amide or peptide bond include, but are not limited to, synthetic routes via an acid chloride, acyl azide, mixed anhydride or activated ester such as a p-nitrophenyl ester. Typically, solution phase amide couplings with or without peptide fragments are performed.

The selection of amino protecting groups used in the preparation of compounds of Formula I is dictated in part by the particular amide coupling conditions, and in part by the components involved in the coupling. Amino-protecting groups commonly used include those which are well-known in the art, for example, benzyloxycarbonyl (carbobenzyloxy) (CBZ), p-methoxybenzyloxycarbonyl, p-nitrobenzyloxycarbonyl, N-tert-butoxycarbonyl (BOC), and the like. It is preferred to use either BOC or CBZ as the protecting group for the α-amino group because of the relative ease of removal by mild acids in the case of BOC, e.g., by trifluoroacetic acid (TFA) or hydrochloric acid in ethyl acetate; or removal by catalytic hydrogenation in the case of CBZ.

PREPARATION OF COMPOUNDS OF FORMULA I

One method of preparing compounds of Formula I where n is 0, $R^1$ is hydrogen and $R^2$ is not —$NR^6R^7$ is from the corresponding unsaturated acid of Formula (4), the preparation of which is shown below in Reaction Scheme I:

REACTION SCHEME I

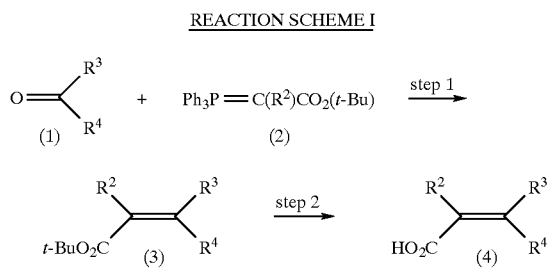

Starting Materials

Aldehydes and ketones of Formula (1) are commercially available, for example from Aldrich Chemical Co., or may be prepared as shown below, or prepared according to methods well known to those skilled in the art. The ylides of Formula (2) are commercially available, for example, (tert-butoxycarbonylmethylene)triphenylphosphorane is available from Aldrich, or may be prepared by standard methods known to those skilled in the art, for example by reacting the appropriate bromo derivative of formula $R^2CHBrCO_2$-(tert-butyl) with triphenylphosphine, and reacting the resulting triphenylphosphonium bromide derivative with a strong base.

Step 1—Preparation of Compounds of Formula (3)

In general, a solution of an aldehyde or ketone compound of Formula (1) is reacted in an inert organic solvent, for example benzene, with a compound of Formula (2) (or alternatively, the corresponding phosphonate, for example trimethyl phosphonoacetate) for a period of 8 to 48 hours at 15° C. to 30° C. (aldehydes), preferably 20° C., or 70° C. to 90° C. (ketones), preferably 80° C., until starting material is consumed. The reaction product, an enoic ester of Formula (3), is isolated and purified by conventional means.

Step 2—Preparation of Compounds of Formula (4)

The compound of Formula (3) is then hydrolyzed under acidic conditions, optionally in the presence of an inert solvent, e.g., treatment with trifluoroacetic acid in methylene chloride for about 20 minutes to 3 hours. The reaction is carried out at a temperature range from about 0° C. to 40° C., preferably at about room temperature. In the case where trimethyl phosphonoacetate is used in Step 1, a methyl ester is produced which may be hydrolyzed conventionally under basic conditions, for example sodium hydroxide in aqueous methanol or ethanol. The reaction product, an enoic acid of Formula (4), is isolated and purified by conventional means.

Preparation of Compounds of Formula (4) where $R^3$ and $R^4$ together with the Carbon to which they are attached represent a Piperidine Derivative The preparation of compounds of Formula (4) where $R^3$ and $R^4$ together with the carbon to which they are attached represent a piperidine derivative, represented below as a compound of Formula (4a), in general requires the protection of the NH group. An example is shown below in Reaction Scheme II.

REACTION SCHEME II

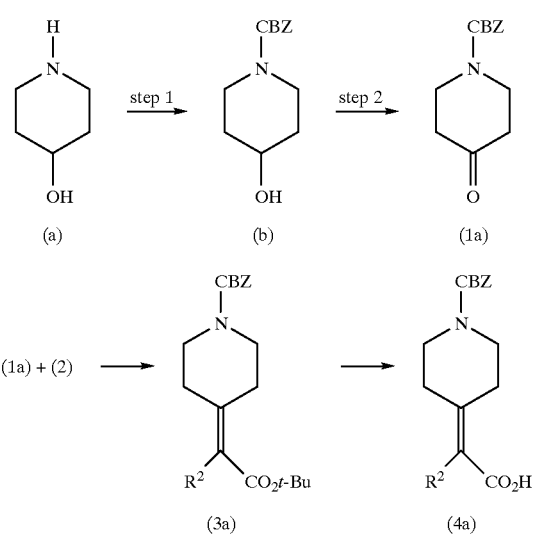

Step 1—Preparation of Compounds of Formula (b)

In general, a solution of a hydroxypiperidine compound of Formula (a) is protected by reaction of (a) in an inert organic solvent, for example tetrahydrofuran, in the presence of an excess of a tertiary base, for example triethylamine, with an equimolar amount of benzyl chloroformate. The reaction is carried out in the temperature range from about 0° C. to 40° C., preferably at about 25° C., for about 10 to 30 hours, preferably about 18 hours. The reaction product of Formula (b) is isolated and purified by conventional means.

Step 2—Preparation of Compounds of Formula (1a)

A compound of Formula (1a) is a compound of Formula (1) where $R^3$ and $R^4$ together with the carbon to which they are attached represent a protected piperidine derivative.

In general, a solution of a compound of Formula (b) is oxidized to a ketone of Formula (1a) by reaction of (b) in an inert organic solvent, for example methylene chloride, with an oxidizing agent, for example pyridinium chlorochromate, preferably in the presence of an inert support, for example Celite. The reaction is carried out in the temperature range from about 0° C. to 40° C., preferably at about 25° C., for about 10 to 30 hours, preferably about 18 hours. The reaction product of Formula (1a) is isolated and purified by conventional means.

Alternatively, reaction of commercially available 4-piperidone monohydrate hydrochloride with benzyl chloroformate under Schotten-Baumann conditions gives a compound of Formula (1a) in a single step.

Preparation of Compounds of Formula (4) where $R^3$ and $R^4$ Together with the Carbon to which they are attached Represent a Piperidine Derivative A compound of Formula (4) where $R^3$ and $R^4$ together with the carbon to which they are attached represent a piperidine derivative is represented as a compound of Formula (4a).

The protected piperidine ketone of Formula (1a) is converted to (3a), which is hydrolyzed to (4a) as described in Reaction Scheme I, Steps 1 and 2. The compound of Formula (4a) is then converted to a compound of Formula I where n is 0 as described in Reaction Scheme III below. The benzyloxycarbonyl (CBZ) protecting group is removed by catalytic hydrogenation, to give a compound of Formula I where $R^3$ and $R^4$ together with the carbon to which they are attached represent piperidine.

Preparation of Compounds of Formula (4) where $R^3$ and $R^4$ Together with the Carbon to which they are attached Represent a Pyran Derivative Compounds of Formula (4) where $R^3$ and $R^4$ together with the carbon to which they are attached represent a tetrahydropyran derivative, represented as Formula (4b), are prepared similarly to the procedure shown above, starting from the corresponding 4-oxotetrahydropyran. The reaction is shown below in Reaction Scheme III and described in Example 3.

REACTION SCHEME III

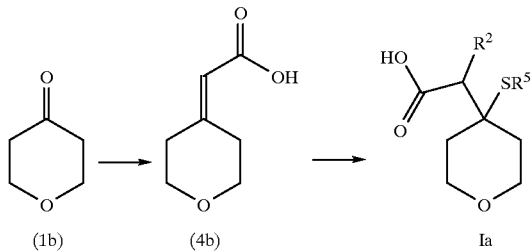

The tetrahydropyran derivative of Formula (4b) is then converted to the corresponding compound of Formula I, i.e., a compound of Formula I where n is 0, as described in Reaction Scheme VII.

Preparation of Compounds of Formula (4) where $R^3$ and $R^4$ Together with the Carbon to which they are Attached represent a Tetrahydrothiopyran-1,1-dioxide Derivative Compounds of Formula (4) where $R^3$ and $R^4$ together with the carbon to which they are attached represent a tetrahydrothiopyran-1,1-dioxide derivative are prepared similarly to the procedure shown above, starting from the corresponding 4-oxotetrahydrothiopyran.

The tetrahydrothiopyran-1,1-dioxide derivative of Formula (4) is then converted to the corresponding compound of Formula I where n is 0 as described in Reaction Scheme III.

Alternative Preparation of Compounds of Formula I

Another method of preparing compounds of Formula I where $R^2$ is not —$NR^6R^7$ and $R^3$ and $R^4$ are both hydrogen is from the corresponding lactone of Formula (10), the preparation of which is shown below in Reaction Scheme IV.

REACTION SCHEME IV

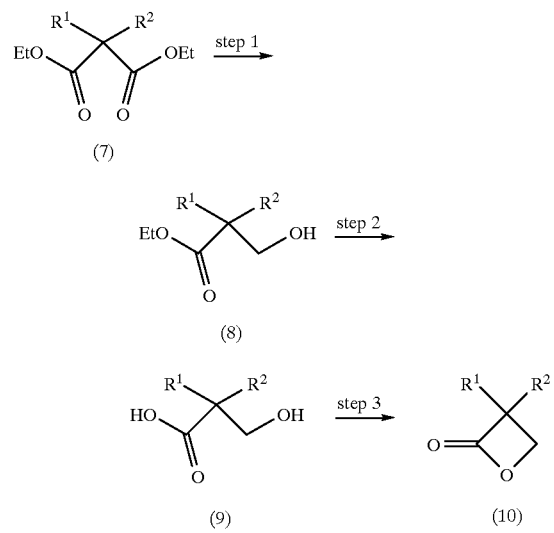

Step 1—Preparation of Compounds of Formula (8)

The starting compounds of Formula (7) are commercially available, or may be prepared by means well known in the art starting from diethyl malonate, e.g., Gibson and Johnson, J. Chem. Soc., p2525 (1930), (other diesters may be employed in place of the diethyl ester if desired). In general, a solution of a compound of Formula (7) is dissolved in an inert aromatic solvent, preferably benzene or toluene, and cooled to about −40° to −20° C., preferably about −30° C. To this cold solution is added a suitable hindered reducing agent, preferably diisobutylaluminum hydride in an inert aromatic solvent, maintaining the temperature at no higher than about 25° C. After the addition is complete, the reaction is maintained at about 15° C. until all the starting material is consumed. After about 10 minutes the reaction is quenched by addition of a protic solvent, preferably ethanol, maintaining the temperature at no higher than about −15° C. Sodium borohydride is optionally added, but preferably the reaction is simply allowed to warm to about room temperature. The reaction product of Formula (8) is isolated and purified by conventional means.

Step 2—Preparation of Compounds of Formula (9)

In general, the compound of Formula (8) is hydrolysed with a base to form the hydroxymethyl acid of Formula (9).

The compound of Formula (8) is dissolved in an aqueous protic solvent, preferably aqueous methanol, and reacted with about 3 molar equivalents of a base, for example potassium hydroxide or lithium iodide, followed by sodium cyanide. The reaction is carried out in the temperature range from about 80° C. to 120° C., preferably at about the reflux temperature of the solvent mixture, for about 8 hours. The reaction product of Formula (9) is isolated and purified by conventional means.

Step 3—Preparation of Compounds of Formula (10)

In general, the compound of Formula (9) is dehydrated to form a lactone of Formula (10).

To a mixture of the compound of Formula (9) and about 2 molar equivalents of a tertiary base, preferably triethylamine, optionally in the presence of 4-dimethylaminopyridine, in an inert solvent, for example, diethyl ether or dichloromethane, at about −20° C., is added about 1 molar equivalent of a dehydrating agent, for example trifluoromethanesulfonic anhydride, methanesulfonic anhydride, methanesulfonyl chloride, p-toluenesulfonyl chloride, benzenesulfonyl chloride, preferably benzenesulfonyl chloride. The reaction is carried out at about −10° C., for about 10 minutes to 4 hours, preferably about 30 minutes. The reaction product of Formula (10) is isolated by conventional means synthesis without further purification.

Preparation of Compounds of Formula (10) where $R^1$ and $R^2$ together with the Carbon to which they are attached Represent a Tetrahydropyran Derivative To give a specific example, the preparation of a compound of Formula (10) where $R^1$ and $R^2$ together with the carbon to which they are attached represent a tetrahydropyran derivative (represented as Formula (10a)) is shown below in Reaction Scheme V, and described in Example 5.

REACTION SCHEME V

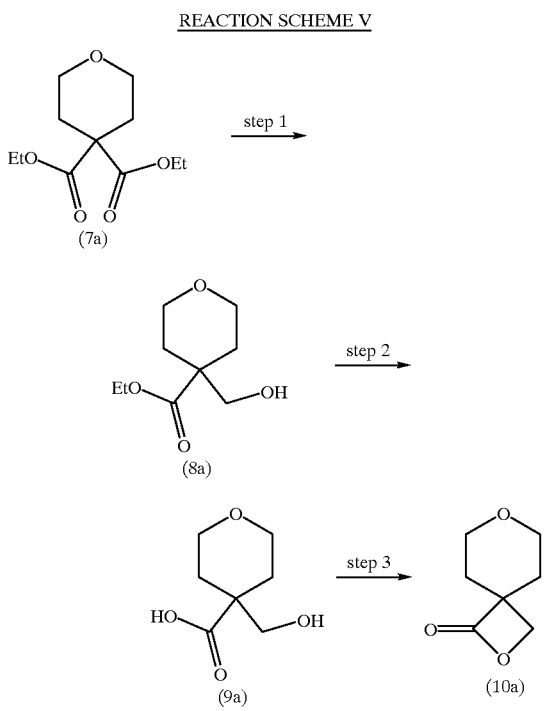

The starting compound of Formula (7a) is either commercially available or may be prepared as shown in Example 31A. Steps 1–3 are carried out in the same manner as shown in Reaction Scheme IV.

Preparation of Compounds of Formula (10) where $R^3$ and $R^4$ are as Defined in the Summary of the Invention The preparation of a compound of Formula (10) where $R^3$ and $R^4$ are as defined in the Summary of the Invention, represented as Formula (10b), is shown below in Reaction Scheme VI, and described in Example 5.

REACTION SCHEME VI

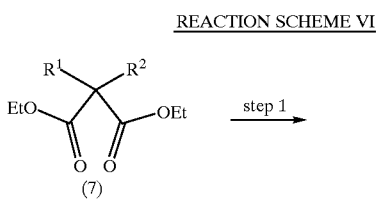

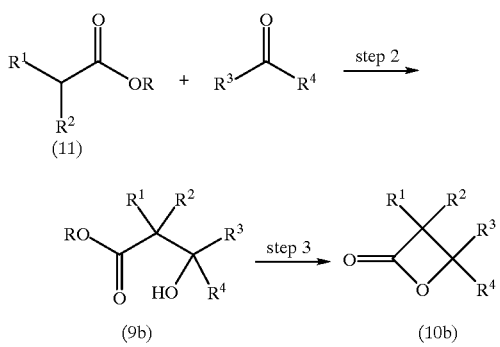

Step 1—Preparation of Compounds of Formula (11)

The compound of Formula (11), where R=Et, may be prepared from the compound of Formula (7) by decarboxylation. In general, the diester is reacted with a mixture of lithium iodide and sodium cyanide at about 130° to 140° C. in a suitable solvent, for example N,N-dimethylformamide, for about 24 hours.

Step 2—Preparation of Compounds of Formula (9b)

In general, an anion of a compound of Formula (11), where R=H or lower alkyl, is reacted with a compound of the formula $R^3R^4C=O$ to form a hydroxy acid or hydroxyester respectively of Formula (9b).

A solution of the compound of Formula (11) in an anhydrous ethereal solvent, preferably tetrahydrofuran, is added to about 1.1 molar equivalent (when R is lower alkyl) or about 2 molar equivalents (when R is hydrogen) of a hindered base, preferably lithium diisopropylamide, in an anhydrous ethereal solvent, preferably tetrahydrofuran, at about 0° C. When the addition is complete, a small quantity of a polar solvent is optionally added, preferably hexamethylphosphoramide. To this mixture is added an excess of a compound of the formula $R^3R^4C=O$. The addition is carried out at a temperature range of about −78 to 10° C., preferably at about −78° C. when $R^3$ and $R^4$ are hydrogen, or preferably 0° C. for ketones, followed by reaction at room temperature for about 2–24 hours, preferably about 10 hours. Where R in the starting material of Formula (11) is hydrogen, the reaction product of Formula (9b) is isolated and purified by conventional means. Where R in the starting material of Formula (11) is lower alkyl, the reaction product of Formula (9b) where R=H is obtained by hydrolyzing the ester product using a base, preferably lithium hydroxide, as described above, then isolating and purifying (9b) by conventional means.

Step 3—Preparation of Compounds of Formula (10b)

The compound of Formula (9b) is then converted to a compound of Formula (10b) in the same manner as described in Reaction Scheme IV.

The method of Reaction Scheme VI can be used, for example, to prepare compounds of Formula (10) where $R^1$ and $R^2$ taken together with the carbon to which they are attached is tetrahydropyran-4-yl, by starting with 4-carboxytetrahydropyran or an ester thereof, for example, the ethyl ester. Similarly, compounds of Formula (10) where $R^1$ and $R^2$ taken together with the carbon to which they are attached is piperidin-4-yl or derivatives thereof, may be prepared by starting with 1-benzyloxycarbonyl-4-carboxypiperidine, N-(tert-butoxycarbonyl)-4-carboxypiperidine, or an ester thereof, for example, the ethyl ester.

Alternative Preparation of Compounds of Formula I

Compounds of Formula I can also be prepared from compounds of Formula (13), the preparation of which is shown below in Reaction Scheme VIa, and described in Example 5A.

REACTION SCHEME VIA

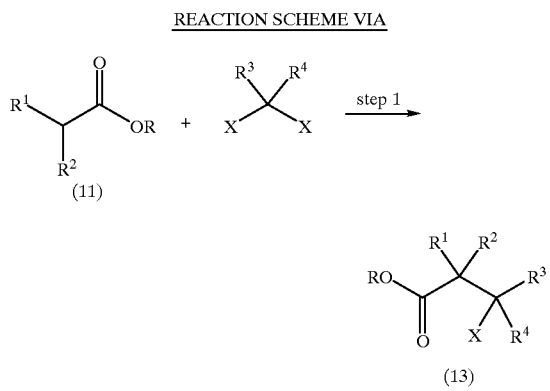

where R is hydrogen or lower alkyl, and X is halo or -p-tosyl.

Step 1—Preparation of Compounds of Formula (13) from (11)

The starting compounds of Formula (13) are commercially available, for example, an ester of commercially available chloropivalic acid may be prepared conventionally, or compounds of Formula (13) may be prepared by means well known in the art, for example, Gibson and Johnson, *J. Chem. Soc.*, p2525 (1930). In general, an anion of a compound of Formula (11) is reacted with an alkyl dihalide to form a halo-substituted hydroxy acid ester of Formula (13)

A solution of the compound of Formula (11) in an anhydrous ethereal solvent, preferably tetrahydrofuran, is added to about 1.1 molar equivalent (when R is lower alkyl) or about 2 molar equivalents (when R is hydrogen) of a hindered base, preferably lithium diisopropylamide, in an anhydrous ethereal solvent, preferably tetrahydrofuran, at about −100 to 0° C., preferably at about −78° C. To this mixture is added an excess of an alkyl dihalide, preferably diiodomethane. The addition is carried out a temperature range of about −5° to 50° C. for about 1–5 hours. The reaction product of Formula (13) is isolated by conventional means, and preferably used in the next step of the synthesis without further purification.

It should be noted that a compounds of Formula (13) where X is p-tosyl, are obtained by tosylation by conventional means of compounds of Formula (8) or (9b).

Preparation of Compounds of Formula I

The intermediates of Formulae (4), (10), and (13) may be converted to compounds of Formula I where Y is hydroxy and n is 0, designated as compounds of Formula Ia, as shown in Reaction Scheme VII below.

REACTION SCHEME VII

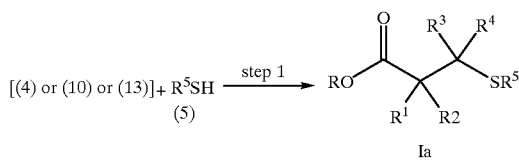

where R is hydrogen or lower alkyl.

Compounds of Formula (4) are either commercially available, for example from Aldrich, or may be prepared according to methods known to those skilled in the art, for example, as described by Mannich and Rister, *Chem. Ber.*, 57, 1116 (1924) for acids where $R^3$ and $R^4$ are each hydrogen, or may be prepared as described above, or as described in Example 3. Compounds of Formula (5) are commercially available, for example from Aldrich, Fluka, etc.), or may be prepared according to methods known to those skilled in the art, e.g., as described below in Example 4.

Step 1—Preparation of Compounds of Formula Ia from (4)

Compounds of Formula I where n is 0 and Y is hydroxy, designated as compounds of Formula Ia, may be prepared by heating an enoic acid of Formula (4) with an equimolar amount of a thiol of Formula (5) in the presence of an approximately equimolar amount of a secondary amine, preferably piperidine. The reaction is carried out in the temperature range from about 70° C. to 120° C., preferably at about 100° C., for about 1 to 24 hours, preferably about 3 hours. The sulfide reaction product, a compound of Formula Ia, is isolated and purified by conventional means.

Step 1—Preparation of Compounds of Formula Ia from (10)

Compounds of Formula I where n is 0 and Y is hydroxy, designated as compounds of Formula Ia, may be prepared by reacting a lactone of Formula (10) with about 1.1 molar equivalents of an anion of a thiol of Formula (5) (generated by reaction of (5) with an alkaline metal hydride, preferably sodium hydride in a polar solvent, preferably N,N-dimethylformamide). The reaction is carried out in a polar solvent, preferably N,N-dimethylformamide, at a temperature range of about 0° C. to 70° C., preferably at about 0° to 25° C. The sulfide reaction product, a compound of Formula Ia, is isolated and purified by conventional means.

Step 1—Preparation of Compounds of Formula Ia from (13)

Compounds of Formula I where n is 0 and Y is hydroxy or lower alkoxy, designated as compounds of Formula Ia, may be prepared by reacting an enoic acid ester of Formula (13) with about 1.1 molar equivalents of an anion of a thiol of Formula (5) (generated by reaction of (5) with an alkaline metal hydride, preferably sodium hydride in a polar solvent, preferably N,N-dimethylformamide). The reaction is carried out in a polar solvent, preferably N,N-dimethylformamide, at a temperature range of about 30° C. to 120° C., preferably at about 80° C., for about 10 minutes. The sulfide reaction product, a compound of Formula Ia, is isolated and purified by conventional means.

Conversion of Compounds of Formula Ia to other Compounds of Formula I

One method of converting compounds of Formula Ia to other compounds of Formula I is shown below in Reaction Scheme VIII.

REACTION SCHEME VIII

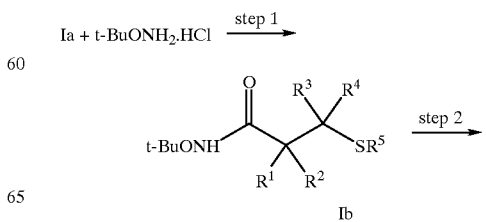

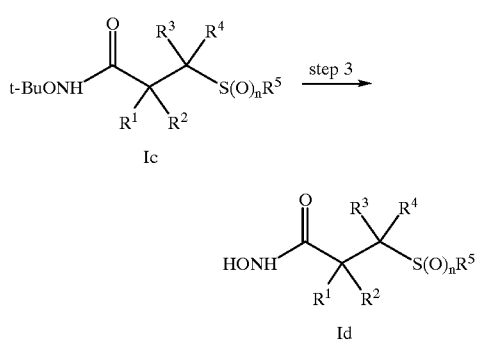

Step 1—Preparation of Compounds of Formula Ib

In general, compounds of Formula I where n is 0 and Y is tert-BuONH—, designated as compounds of Formula Ib, are prepared by reacting a compound of Formula Ia with an excess of a O-(tert-butyl)hydroxylamine hydrochloride and N-ethyl-N'-(3-dimethylaminopropyl)-carbodiimide hydrochloride (or other carbodiimide derivatives, for example 1,3-dicyclohexylcarbodiimide), in the presence of 1-hydroxybenzotriazole hydrate and a tertiary base, for example dimethylaminopyridine, triethylamine, 4-methylmorpholine, pyridine, or a mixture of such bases. The reaction is carried out in an inert solvent, preferably methylene chloride, in the temperature range from about 0° C. to 40° C., preferably at about 25° C., for about 10 to 30 hours, preferably about 18 hours. The N-tert-butoxy reaction product, a compound of Formula Ib, is isolated and purified by conventional means.

Step 2—Preparation of Compounds of Formula Ic where n is 1

In general, compounds of Formula I where n is 1 and Y is tert-BuONH—, (i.e., sulfoxides), designated as compounds of Formula Ic, are prepared from compounds of Formula Ib by reaction with a mild oxidizing agent, for example sodium periodate or one equivalent of "OXONE"™ (potassium peroxymonosulfate, Aldrich Chemical Co.), until starting material can no longer be detected. The reaction is carried out in an inert solvent, preferably aqueous acetone, in the temperature range from about 0° C. to 40° C., preferably at about 25° C., for about 10 minutes to 4 hours, preferably about 30 minutes. The sulfoxide product, a compound of Formula Ic where n is 1, is isolated and purified by conventional means.

Step 2—Preparation of Compounds of Formula Ic where n is 2

In general, compounds of Formula I where n is 2, Y is tert-BuONH—, and $R^1$ is hydrogen (i.e., sulfones), designated as compounds of Formula Ic, are prepared from compounds of Formula Ib by reaction with about 1–3 molar equivalents, preferably about 1.5 molar equivalents, of a strong oxidizing agent, for example, m-chloroperbenzoic acid or OXONE. The reaction is carried out in an inert solvent, preferably a protic solvent, preferably aqueous methanol, in the temperature range from about 0° C. to 40° C., preferably at about 25° C., for about 10 minutes to 4 hours, preferably about 2 hours. The sulfone product, a compound of Formula Ic where n is 2, is isolated and purified by conventional means.

Step 3—Preparation of Compounds of Formula Id

In general, compounds of Formula I where Y is HONH—, designated as compounds of Formula Id, are prepared by hydrolysing an N-tert-butoxy compound of Formula Ib or Ic under acid conditions under conditions similar to that shown for the preparation of compounds of Formula (4) above, or using hydrochloric acid gas in a sealed tube in an inert solvent, for example, 1,2-dichloroethane. The hydroxyamino reaction product, a compound of Formula Id where Y is HONH—, is isolated and purified by conventional means.

Alternative Method of Introduction of $R^3$ and $R^4$ into Compounds of Formula I An alternative method of introducing the groups $R^3$ and $R^4$ into compounds of Formula I is shown below in Reaction Scheme VIIIA.

REACTION SCHEME VIIIA

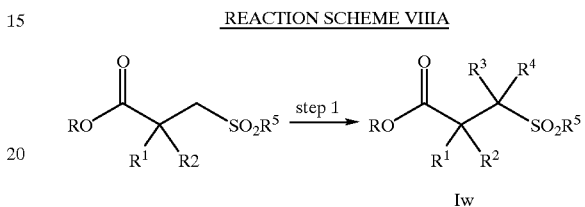

where R is hydrogen or lower alkyl.

Step 1—Preparation of Compounds of Formula I where n is 2, and $R^3$ is as defined in the Summary of the Invention but is other than Hydrogen The compounds of Formula I where n is 2, Y is hydroxy or alkoxy, $R^3$ is as defined in the Summary of the Invention other than hydrogen, and $R^1$, $R^2$, and $R^4$ are defined in the Summary of the Invention, designated as compounds of Formula Iw are prepared by the alkylation of compounds of Formula I where both $R^3$ and $R^4$ are hydrogen.

A solution of the compound of Formula Iw in an anhydrous ethereal solvent, preferably tetrahydrofuran, is added to a hindered base, preferably lithium diisopropylamide, in a manner similar shown above in Reaction Scheme VIA. To this mixture is added about 1 molar equivalent of an alkyl or aralkyl halide. The reaction addition is stirred for about 1–3 hours, then stirred stirred for an additional 1–5 hours, preferably 3 hours, at about room temperature. The reaction product is isolated and purified by conventional means.

$R^4$ may be introduced in the same manner as shown above.

Compounds of Formula Iw can be converted to other compounds of Formula I as shown previously.

Preferred Procedure for Preparing Compounds of Formula Id from Compounds of Formula Ia A preferred method of converting compounds of Formula Ia to other compounds of Formula I is shown below in Reaction Scheme IX.

REACTION SCHEME IX

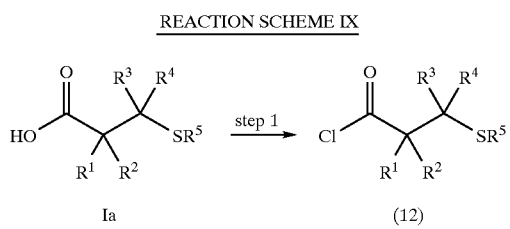

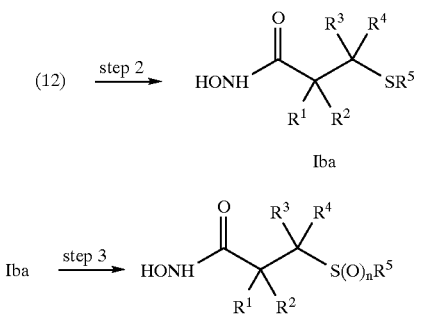

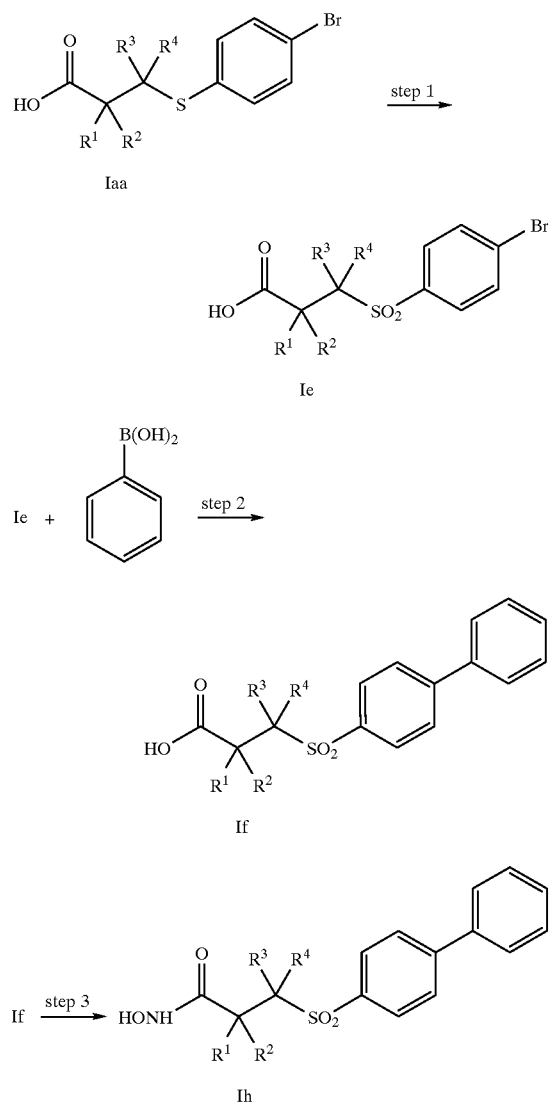

REACTION SCHEME X

Step 1—Preparation of Compounds of Formula Iba

In general, an acid halide of a compound of Formula Ia, designated as compounds of Formula (12), is prepared by reacting a compound of Formula Ia with a halogenating agent.

The compound of Formula Ia is reacted with an excess of a halogenating agent, for example oxalyl chloride, oxalyl bromide, phosphorous oxychoride, phosphorous trichloride, phosphorous pentachloride, thionyl chloride, preferably oxalyl chloride in the presence of a small amount of N,N-dimethylformamide as a catalyst. The reaction is carried out in an inert solvent, preferably methylene chloride, in the temperature range from about 0° C. to 40° C., preferably at about 25° C., for about 10 to 30 hours, preferably about 18 hours. The acid halide reaction product, a compound of Formula (12), is isolated by conventional means.

Step 2—Preparation of Compounds of Formula Iba

Compounds of Formula I where n is 0 and Y is HONH—, designated as compounds of Formula Iba, may be prepared by reacting a compound of Formula (12) with about 1–5 molar equivalents, preferably about 3.5 molar equivalents, of N,O-bis(trimethylsilyl)hydroxylamine, or more preferably aqueous hydroxylamine dissolved in a suitable solvent, for example a mixture of tert-butanol/tetrahydrofuran. The reaction is carried out in an inert solvent, preferably methylene chloride, in the temperature range from about 0° C. to 25° C., preferably at about 25° C., for about 1–10 hours, preferably about 3 hours for N,O-bis(trimethylsilyl) hydroxylamine, or about 1.5 hours for aqueous hydroxylamine. The N-hydroxamic acid product, a compound of Formula Iba, is isolated and purified by conventional means.

Step 3—Preparation of Compounds of Formula Id

The compound of Formula Iba is converted to a compound of Formula Id where n is 1 or 2 in the same manner as shown in Reaction Scheme VIII, steps 2 or 3, above.

Alternative Preparation of Compounds of Formula I

It should be noted that the sequence of the steps in the above Reaction Schemes for the preparation of compounds of Formula Id may be changed. That is, a compound of Formula Ia may be oxidized first to a sulfone, followed by conversion of the carboxy group to hydroxyamino as shown above, if so desired.

Preparation of Compounds of Formula I where $R^5$ is Biphenyl

Compounds of Formula I where $R^5$ is optionally substituted biphenyl are preferably prepared from compounds of Formula Ia where $R^5$ is optionally substituted bromophenyl. For example, compounds where $R^5$ is 4-biphenyl can be prepared from compounds of Formula Ia where $R^5$ is 4-bromophenyl, represented below as a compound of Formula Iaa, as shown below in Reaction Scheme X.

Step 1—Preparation of Compounds of Formula Ie

In general, compounds of Formula I where n is 2, Y is hydroxy, $R^5$ is 4-bromophenyl, and $R^1$, $R^2$, $R^3$, and $R^4$ are as defined in the Summary of the Invention, designated as compounds of Formula Ie, are prepared from compounds of Formula Iaa by reaction with a strong oxidizing agent in the same manner as shown above in Reaction Scheme VIII, Step 2.

Step 2—Preparation of Compounds of Formula If

In general, compounds of Formula I where n is 2, Y is hydroxy, $R^5$ is biphenyl, and $R^1$, $R^2$, $R^3$, and $R^4$ are as defined in the Summary of the Invention, designated as compounds of Formula If, are prepared by reacting a compound of Formula Ie with phenylboronic acid and zerovalent palladium catalysts, preferably tetrakis (triphenylphosphine)palladium. The reaction is carried out in a protic solvent, preferably a mixture of ethanol and benzene, in the temperature range from about 30° C. to 100° C., preferably at about 80° C. When the desired temperature is reached, aqueous 2M sodium carbonate is added, and refluxing continued for about 1–8 hours, preferably about 2 hours. The reaction product, a compound of Formula If, is isolated by conventional means and preferably purified using preparative TLC.

Step 3—Preparation of Compounds of Formula Ih

In general, compounds of Formula I where n is 2, Y is HONH—, $R^5$ is biphenyl, and $R^1$, $R^2$, $R^3$, and $R^4$ are as defined in the Summary of the Invention, designated as compounds of Formula Ih, may be prepared from the corresponding compounds of Formula If in the same manner as shown above in Reaction Scheme VIII, or preferably as shown in Reaction Scheme IX or X.

To prepare compounds of Formula I where $R^5$ is substituted biphenyl, a compound of Formula Iaa optionally substituted on the 4-bromophenyl ring is reacted with an optionally substituted boronic acid in the same manner as shown above.

Preparation of Compounds of Formula I where $R^5$ is Diphenylsulfide

Compounds of Formula I where $R^5$ is optionally substituted diphenylsulfide are preferably prepared from the corresponding compounds of Formula Ie, i.e., compounds of Formula I in which $R^5$ is optionally substituted 4-bromophenyl, prepared as in Reaction Scheme X. For example, compounds where $R^5$ is 4-diphenylsulfide can be prepared from compounds of Formula Ie as shown below in Reaction Scheme XI.

REACTION SCHEME XI

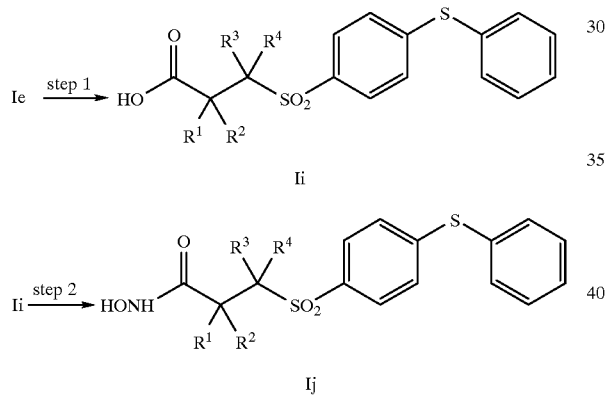

Step 1—Preparation of Compounds of Formula Ii

In general, compounds of Formula I where n is 2, Y is hydroxy, $R^5$ is 4-diphenylsulfide, and $R^1$, $R^2$, $R^3$, and $R^4$ are as defined in the Summary of the Invention, designated as compounds of Formula Ii, are prepared from compounds of Formula Ie by heating an anion of thiophenol (preferably prepared in situ, for example, by treatment of thiophenol with sodium or potassium hydride, preferably potassium hydride, in a polar solvent, preferably N,N-dimethylformamide. The reaction is carried out in a polar solvent, preferably N,N-dimethylformamide, in the temperature range from about 30° C. to 100° C., preferably at about 75° C., for about 4–48 hours, preferably about 18 hours. The reaction product, a compound of Formula Ii, is isolated by conventional means and preferably purified using preparative TLC.

Step 2—Preparation of Compounds of Formula Ii

In general, compounds of Formula I where n is 2, Y is HONH—, $R^5$ is 4-diphenylsulfide, and $R^1$, $R^2$, $R^3$, and $R^4$ are as defined in the Summary of the Invention, designated as compounds of Formula Ij, are prepared from the corresponding compounds of Formula Ii in the same manner as shown above in Reaction Scheme VIII, or preferably as shown in Reaction Scheme IX or X.

To prepare compounds of Formula I where $R^5$ is substituted 4-diphenylsulfide, a compound of Formula Ie optionally substituted on the 4-bromophenyl ring is reacted with an optionally substituted anion of thiophenol in the same manner as shown above.

Preparation of Compounds of Formula I where $R^5$ is 4-[4-(thiophen-2-yl)phenoxy]phenyl Compounds of Formula I where $R^5$ is optionally substituted 4-[4-(4-thiophen-2-yl)phenoxy]phenyl are prepared from the corresponding compounds of Formula I where R is optionally substituted 4-(4-bromophenoxy)phenyl. This reaction is shown in Reaction Scheme XIA.

REACTION SCHEME XIA

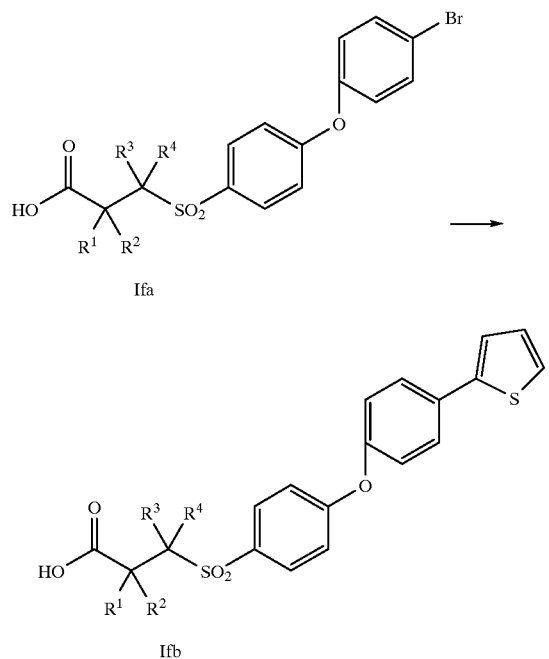

Preparation of Compounds of Formula Ifb

The 4-bromo group of the compound of Formula (Ifa), which may be prepared by methods analogous to those previously shown, or as described in Example 16D, is displaced to give a compound of Formula Ifb, using the same procedure as described in Reaction Scheme X, step 2.

The compound of Formula (Ifa) is reacted similarly in order to introduce other aryl or heteroaryl groups.

Reduction of a compound of Formula Ifa with palladium and hydrogen replaces the bromo group by hydrogen.

Preparation of Compounds of Formula I where $R^5$ is 1,2-Diphenylethene

Compounds of Formula I where $R^5$ is optionally substituted 1,2-diphenylethene are preferably prepared from the corresponding compounds of Formula I where $R^5$ is optionally substituted 4-bromophenyl, as prepared in Reaction Scheme X. For example, compounds where $R^5$ is 4-diphenylethene can be prepared from compounds of Formula Ie as shown below in Reaction Scheme XII.

REACTION SCHEME XII

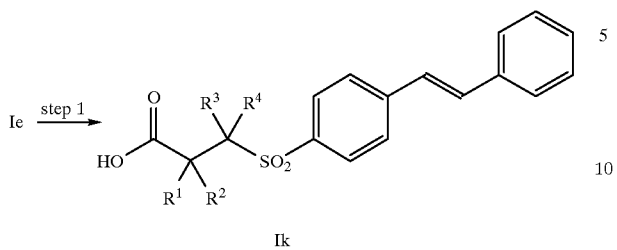

Step 1—Preparation of Compounds of Formula Ik

In general, compounds of Formula I where Y is hydroxy, $R^5$ is 4-(1,2-diphenylethene), and $R^1$, $R^2$, $R^3$, and $R^4$ are as defined in the Summary of the Invention, designated as compounds of Formula Ik, are prepared by reacting a compound of Formula Ie with an optionally substituted styrene in the presence of a hindered tertiary organic base, for example diisopropylethylamine, and palladium diacetate, and trimethylphenylphosphine or other triphenylphosphine derivatives, preferably trimethylphenylphosphine or tetrakis(triphenylphosphine)palladium(O). The reaction is carried out in the absence of solvent, in the temperature range from about 30° C. to 100° C., preferably at about 80° C., for about 4–48 hours, preferably about 16 hours. The reaction product, a compound of Formula Ik, is isolated by conventional means and preferably purified using preparative TLC.

Conversion of the carboxylic acid of Formula Ik to its hydroxyamino equivalent is carried out in the same manner as shown above in Reaction Scheme VIII, or preferably as shown in Reaction Scheme IX or X.

Preparation of Compounds of Formula I where $R^3$ and $R^4$ together with the Carbon to which they are attached represent an N-Substituted Piperidine Derivative The preparation of compounds of Formula I where $R^1$ and $R^2$ or $R^3$ and $R^4$ together with the carbon to which they are attached represent an N-substituted piperidine derivative are prepared from the corresponding unsubstituted piperidine derivative. This procedure is exemplified by reference to a compound of Formula I where $R^3$ and $R^4$ together with the carbon to which they are attached represent an N-substituted piperidine derivative, designated as compounds of Formula Il, as shown below in Reaction Scheme XIII.

REACTION SCHEME XIII

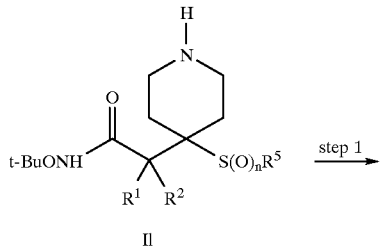

Step 1—Preparation of Compounds of Formula Im

Compounds of Formula I where Y is t-BuONH—, $R^1$ and $R^2$ are as defined in the Summary of the Invention, and $R^3$ and $R^4$ together with the carbon to which they are attached represent an N-substituted piperidine derivative, are designated as compounds of Formula Im.

In general, compounds of Formula Im are prepared by reacting a compound of Formula Il with a compound of the formula RX, where R is lower alkyl, cycloalkylalkyl, acyl, alkoxycarbonylalkyl, picolyl, —SO$_2$R, where $R^a$ is lower alkyl or —NR$^b$R$^c$, where $R^b$ and $R^c$ are independently hydrogen or lower alkyl; and the like, and X is chloro, bromo or iodo; for example, RX may be methyl iodide, cyclopropylmethyl bromide, 3-picolyl chloride, ethyl bromoacetate, bromoacetamide, acetyl chloride, dimethylaminosulfonyl chloride, in the presence of a base, for example triethylamine or potassium carbonate. The reaction is carried out in a polar solvent, preferably N,N-dimethylformamide, in the temperature range from about 0° C. to 50° C., 3 preferably at about 25° C., for about 4 to 48 hours, preferably about 16 hours. The reaction product, a compound of Formula Im, is isolated by conventional means and preferably used with no further purification.

Alternatively, a reductive alkylation may be carried out on a compound of Formula Il to give a compound of Formula Im. For example, reducing a compound of Formula Il in acetone in the presence of a catalyst, for example palladium on carbon, under hydrogen gives an N-isopropyl derivative of Formula Im.

Step 2—Preparation of Compounds of Formula In

Compounds of Formula I where Y is HONH—, $R^1$ and $R^2$ are as defined in the Summary of the Invention, and $R^3$ and $R^4$ together with the carbon to which they are attached represent an N-substituted piperidine derivative, are designated as compounds of Formula In.

In general, compounds of Formula In are prepared from a compound of Formula Im by reaction with a strong acid, preferably hydrochloric acid. The reaction is carried out in a sealed tube in an inert solvent, preferably 1,2-dichloroethane, in the temperature range from about 0° C. to 45° C., preferably at about 20° C., for about 10 to 72 hours, preferably about 48 hours. The reaction product, a compound of Formula In, is isolated and purified by conventional means, preferably by chromatography.

Preparation of Compounds of Formula I where $R^2$ is —NR$^6$R$^7$

Compounds of Formula I where $R^2$ is —$NR^6R^7$, in which R6 is hydrogen and $R^7$ is CBZ, where CBZ represents benzyloxycarbonyl, and $R^1$, $R^3$ and $R^4$ are hydrogen, shown below, for example, as Formulae Ip and Iq, are prepared by a different route, as shown in Reaction Schemes XIV, XV, and XVI. This route provides compounds of Formula Iab, optically pure or as racemic mixtures, depending upon the chirality of the starting lactone.

REACTION SCHEME XIV

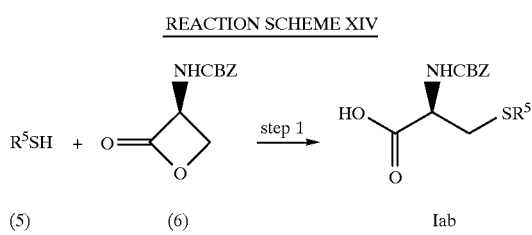

(5)            (6)            Iab

Step 1—Preparation of Compounds of Formula Iab

In general, compounds of Formula Ia where Y is hydroxy, $R^2$ is —$NR^6R^7$, in which $R^6$ is hydrogen and $R^7$ is CBZ, where CBZ represents benzyloxycarbonyl, and $R^1$, $R^3$ and $R^4$ are hydrogen, designated as compounds of Formula Iab, are prepared by treating an anion of a thiol of Formula (5) (preferably prepared in situ, for example, by treatment of Formula (5) with sodium or potassium hydride, preferably potassium hydride, in a polar solvent, preferably N,N-dimethylformamide) with a lactone of Formula (6). The reaction is carried out in a polar solvent, preferably N,N-dimethylformamide, in the temperature range from about 0° C. to 40° C., preferably at about 25° C., for about 5 minutes to 10 hours, preferably about 30 minutes to 6 hours. The sulfide reaction product, a compound of Formula Iab, is isolated by conventional means and preferably used directly in the next step.

Preparation of Compounds of Formula I where $R^2$ is —$NR^6R^7$

Compounds of Formula I where $R^2$ is —$NR^6R^7$, in which $R^6$ is hydrogen and $R^7$ is CBZ, where CBZ represents benzyloxycarbonyl, and $R^1$, $R^3$ and $R^4$ are hydrogen, are prepared from compounds of Formula Iab as shown below in Reaction Scheme XV.

REACTION SCHEME XV

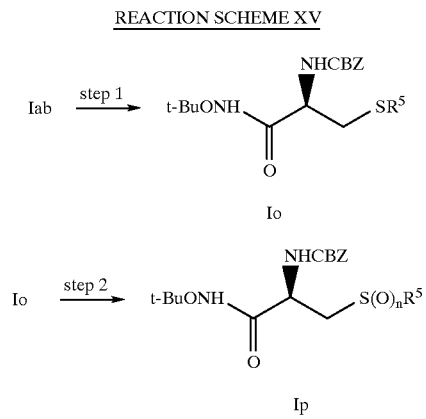

-continued

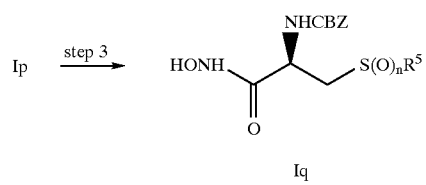

Step 1—Preparation of Compounds of Formula Io

Compounds of Formula I where Y is tert-BuONH—, $R^2$ is —NHCBZ where CBZ represents benzyloxycarbonyl, and $R^1$, $R^3$ and $R^4$ are hydrogen, designated as compounds of Formula Io, are prepared as shown in the same manner as shown in Reaction Scheme VIII, or preferably as shown in Reaction Scheme IX or X.

Step 2—Preparation of Compounds of Formula Ip

Compounds of Formula Ip where n is 2, Y is tert-BuONH—, $R^2$ is —NHCBZ where CBZ represents benzyloxycarbonyl, and $R^1$, $R^3$ and $R^4$ are hydrogen, designated as compounds of the Formula Ip, are prepared in the same manner as shown in Reaction Scheme VIII, or preferably as shown in Reaction Scheme IX or X.

Step 3—Preparation of Compounds of Formula Iq

Compounds of Formula I where n is 2, Y is HONH—, $R^2$ is —NHCBZ where CBZ represents benzyloxycarbonyl, and $R^1$, $R^3$ and $R^4$ are as defined in the Summary of the Invention, designated as compounds of the Formula Iq, are prepared by hydrolyzing a compound of Formula Ip in the same manner as shown above in Reaction Scheme VIII, or preferably as shown in Reaction Scheme IX or X.

Preparation of Compounds of Formula I where $R^2$ is —$NR^6R^7$

Compounds of Formula I where $R^2$ is —$NR^6R^7$, in which $R^6$ and $R^7$ are both hydrogen, and $R^1$, $R^3$ and $R^4$ are hydrogen, are prepared from compounds of Formula Ip as shown below in Reaction Scheme XVI.

REACTION SCHEME XVI

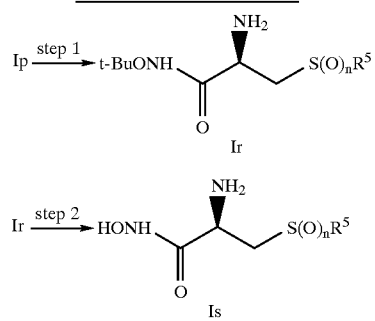

Step 1—Preparation of Compounds of Formula Ir

In general, compounds of Formula I where n is 2, Y is tert-BuONH—, $R^2$ is —$NH_2$, and $R^1$, $R^3$ and $R^4$ are hydrogen, designated as compounds of Formula Ir, are prepared by reducing a compound of Formula Ip using a metal catalyst, preferably palladium on carbon. The reaction is carried out under hydrogen at about 1 atmosphere, in a protic solvent, preferably ethanol, in the temperature range from about 0° C. to 40° C., preferably at about 25° C., for about 4 to 48 hours, preferably about 18 hours. The N-tert-butoxy reaction product, a compound of Formula Ir, is isolated and purified by conventional means.

Step 2—Preparation of Compounds of Formula Is

In general, compounds of Formula I where n is 2, Y is HONH—, $R^2$ is —$NH_2$, and $R^1$, $R^3$ and $R^4$ are hydrogen, designated as compounds of Formula Is, are prepared by reacting a compound of Formula Ir with a strong acid, preferably hydrochloric acid. The reaction is carried out in a sealed tube in an inert solvent, preferably 1,2-dichloroethane, in the temperature range from about −10° C. to 40° C., preferably at about 25° C., for about 4 to 48 hours, preferably about 18 hours. The hydroxyamino reaction product, a compound of Formula Is, is isolated and purified by conventional means, preferably as its hydrochloride salt.
Preparation of Compounds of Formula I where $R^2$ is —$NR^6R^7$ Alternatively, the compound of Formula Ir can be used to produce other compounds of Formula I where $R^6$ and/or $R^7$ are as defined in the Summary of the invention, but not both hydrogen. For example, the preparation of a compound of Formula I where $R^2$ is valine amide is shown below in Reaction Scheme XVII.

REACTION SCHEME XVII

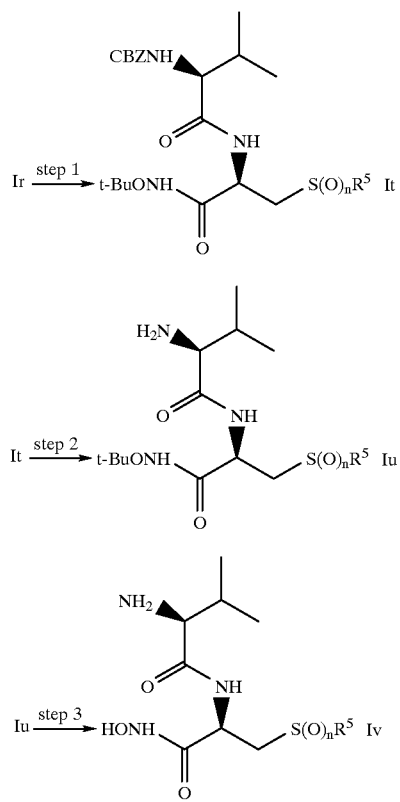

Step 1—Preparation of Compounds of Formula It

In general, compounds of Formula I where n is 2, Y is tert-BuONH—, $R^2$ is 2-(S)-CBZ-valine amide, i.e., where $R^6$ is hydrogen and $R^7$ is 2-(S)-CBZ-3-methyl-1-butanoyl, where CBZ represents benzyloxycarbonyl, and $R^1$, $R^3$ and $R^4$ are hydrogen, designated as compounds of Formula It, are prepared by reacting a compound of Formula Ir with CBZ-(S)-valine in the presence of N-ethyl-N'-(3-dimethylaminopropyl)-carbodiimide and 1-hydroxybenzotriazole and a slight excess of a tertiary amine, preferably triethylamine. The reaction is carried out in an inert solvent, preferably methylene chloride, in the temperature range from about 0° C. to 40° C., preferably at about 25° C., for about 6–48 hours, preferably about 16 hours. The reaction product, a compound of Formula It, is isolated by conventional means, and is preferably used in the next step without further purification.

Step 2—Preparation of Compounds of Formula Iu

In general, compounds of Formula I where n is 2, Y is tert-BuONH—, $R^2$ is 2-(S)-amino-valine amide, i.e., where $R^6$ is hydrogen and $R^7$ is 2-(S)-amino-3-methyl-1-butanoyl, and $R^1$, $R^3$ and $R^4$ are hydrogen, designated as compounds of Formula It, are prepared by reducing a compound of Formula It using a metal catalyst, preferably palladium on carbon. The reaction is carried out under hydrogen at about 1 atmosphere, in a protic solvent, preferably a mixture of methanol and ethanol, in the temperature range from about 0° C. to 40° C., preferably at about 25° C., for about 1 to 8 hours, preferably about 3 hours. The reaction product, a compound of Formula Iu, is isolated and purified by conventional means, preferably chromatography.

Step 3—Preparation of Compounds of Formula Iv

In general, compounds of Formula I where n is 2, Y is HONH—, $R^2$ is 2-(S)-amino-valine amide, i.e., where $R^6$ is hydrogen and $R^7$ is 2-(S)-amino-3-methyl-1-butanoyl, and $R^1$, $R^3$ and $R^4$ are hydrogen, designated as compounds of Formula Iv, are prepared by reacting a compound of Formula Iu with a strong acid, preferably hydrochloric acid. The reaction is carried out in a sealed tube in an inert solvent, preferably 1,2-dichloroethane, in the temperature range from about −20° C. to 40° C., preferably at about 25° C., for about 4 to 48 hours, preferably about 24 hours. The hydroxyamine reaction product, a compound of Formula Iv, is isolated and purified by conventional means, preferably as its hydrochloride salt.

Preparation of Compounds of Formula I where $R^2$ is —$NR^6R^7$

In a manner similar to that shown above, compounds of Formula I where $R^2$ is —$NR^6R^7$, in which $R^6$ and $R^7$ are both methyl, are prepared by reacting a compound of Formula Ir in a polar solvent, preferably N,N-dimethylformamide, with about two equivalents of methyl iodide in the presence of a base, preferably potassium carbonate, then treating the product with hydrochloric acid gas as shown in Step 3 above.

Preparation of Compounds of Formula I where $R^2$ is —$NR^6R^7$

In a manner similar to that shown above, compounds of Formula I where where $R^2$ is —$NR^6R^7$, in which $R^6$ is hydrogen and $R^7$ is —$NHSO_2N(CH_3)_2$, are prepared by reacting a compound of Formula Ir with about one equivalent of dimethylsulfamoyl chloride in an inert solvent, preferably methylene chloride, in the presence of a base, preferably pyridine, then treating the product with hydrochloric acid gas as shown in Step 3 above.

Similarly, the compound of Formula Ir can be used to produce other compounds of Formula I where $R^6$ and/or $R^7$ are as defined in the Summary of the invention, but not both hydrogen, in the same manner as shown in Reaction Scheme XVII above.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

Salts of Compounds of Formula I

Some of the compounds of Formula I may be converted to a corresponding acid addition salt by virtue of the presence of basic nitrogen atoms. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0° to 50° C. The resulting salt precipitates spontaneously or may be brought out of solution with a less polar solvent.

Preferred Processes

In summary, the compounds of the present invention are made by the procedures outlined below:

1. A process for preparing compounds of Formula I where $R^1$ is hydrogen comprises:

reacting a compound of the formula:

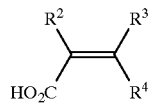

(4)

where $R^2$, $R^3$ and $R^4$ are as defined in the Summary of the Invention, except that $R^2$ cannot be —$NR^6R^7$;
with a compound of the formula $R^5SH$, where $R^5$ is as defined in the Summary of the Invention, in the presence of a secondary base.

2. Alternatively, a process for preparing compounds of Formula I comprises:
reacting a compound of the formula:

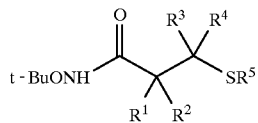

where $R^1$, $R^2$, $R^3$, $R^4$ and $R^5$ are as defined in the Summary of the Invention, with a mild oxidizing agent, for example, sodium periodate.

3. Alternatively, a process for preparing compounds of Formula I comprises:
reacting a compound of the formula:

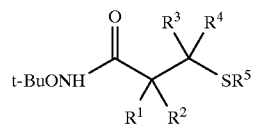

where $R^1$, $R^2$, $R^3$, $R^4$ and $R^5$ are as defined in the Summary of the Invention, with a strong oxidizing agent, for example, OXONE or m-chloroperbenzoic acid.

4. Alternatively, a process for preparing compounds of Formula I where n is 2 comprises:

reacting a compound of the formula:

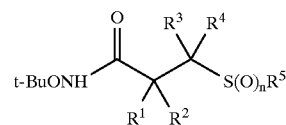

where $R^1$, $R^2$, $R^3$, $R^4$ and $R^5$ are as defined in the Summary of the Invention, with a strong oxidizing agent, for example, OXONE or m-chloroperbenzoic acid.

5. Alternatively, a process for preparing compounds of Formula I comprises:

reacting a compound of the formula:

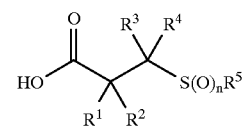

where n, $R^1$, $R^2$, $R^3$, $R^4$ and $R^5$ are as defined in the Summary of the Invention, with O-(tert-butyl) hydroxylamine hydrochloride in the presence of a carbodiimide, for example, N-ethyl-N'-(3-dimethylaminopropyl)carbodiimide hydrochloride, and a tertiary amine.

6. Alternatively, a process for preparing compounds of Formula I comprises:

reacting a compound of the formula:

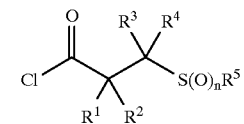

where n, $R^1$, $R^2$, $R^3$, $R^4$ and $R^5$ are as defined in the Summary of the Invention, with hydroxylamine or N,O-bistrimethylsilyl hydroxylamine.

7. Alternatively, a process for preparing compounds of Formula I comprises:

hydrolysing a compound of the formula:

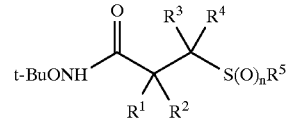

where n, $R^1$, $R^2$, $R^3$, $R^4$ and $R^5$ are as defined in the Summary of the Invention, under acid conditions, for example, with hydrochloric acid or trifluoroacetic acid.

8. Alternatively, a process for preparing compounds of Formula I comprises:

reacting a compound of the formula:

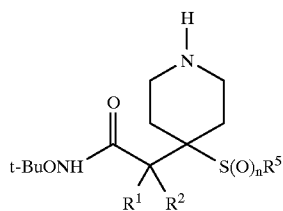

where n, $R^1$, $R^2$ and $R^5$ are as defined in the Summary of the Invention, except that $R^2$ cannot be —$NR^6R^7$;
with a compound of the formula RX, where R is lower alkyl, cycloalkylalkyl, acyl, alkoxycarbonylalkyl, acetamido, picolyl, —$SO_2R^a$, where $R^a$ is lower alkyl or —$NR^bR^c$, where $R^b$ and $R^c$ are independently hydrogen or lower alkyl; and X is chloro, bromo or iodo.

9. Alternatively, a process for preparing compounds of Formula I comprises:
reacting a compound of the formula:

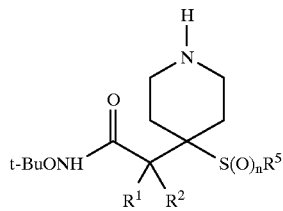

where n, $R^1$, $R^2$ and $R^5$ are as defined in the Summary of the Invention, except that $R^2$ cannot be —$NR^6R^7$;
with acetone under hydrogen in the presence of a catalyst, for example, palladium on carbon, to give the N-isopropyl derivative.

10. Alternatively, a process for preparing compounds of Formula I comprises:
reacting a compound of the formula:

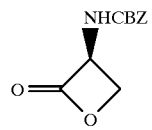

with an anion of a compound of the formula $R^5SH$, where $R^5$ is as defined in the Summary of the Invention.

11. Alternatively, a process for preparing compounds of Formula I comprises:
reacting a compound of the formula:

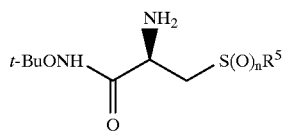

where $R^5$ is as defined in the Summary of the Invention, with an acylating agent, for example CBZ-(S)-valine in the presence of N-ethyl-N'-(3-dimethylaminopropyl)-carbodiimide and 1-hydroxybenzotriazole and a tertiary amine, or an alkylating agent, for example, methyl iodide in the presence of a base or a sulfamoyl halide, such as dimethylsulfamoyl chloride in the presence of a base.

12. Alternatively, a process for preparing compounds of Formula I comprises:
reacting a compound of the formula:

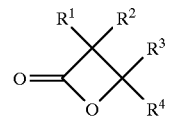

where $R^1$, $R^2$, $R^3$ and $R^4$ are as defined in the Summary of the Invention, except that $R^2$ cannot be —$NR^6R^7$;
with a compound of the formula $R^5SH$, where $R^5$ is as defined in the Summary of the Invention, in the presence of a secondary base.

13. Alternatively, a process for preparing compounds of Formula I comprises:
reacting a compound of the formula:

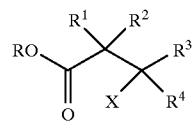

with an anion of a compound of the formula $R^5SH$, where $R^5$ is as defined in the Summary of the Invention.

14. Alternatively, a process for preparing compounds of Formula I comprises:
reacting a compound of the formula:

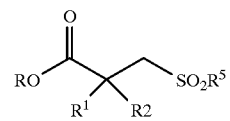

with an alkyl or aralkyl halide in the presence of a hindered base.

15. Alternatively, a process for preparing compounds of Formula I comprises:
reacting a compound of the formula:

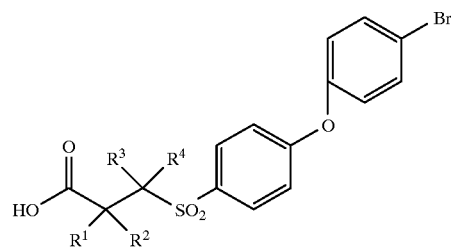

with a compound of the formula $R^{11}B(OH)_2$ or $R^{11}SnMe_3$, where $R^{11}$ is aryl or heteroaryl, in the presence of tetrakis(triphenylphosphine)palladium(0).

Utility, Testing, and Administration

Utility

The compounds of Formula I inhibit mammalian matrix metalloproteases, such as the stromelysins, gelatinases, matrilysin and collagenases, and are therefore useful for treating diseases associated with the MMP-induced excessive degradation of matrix and connective tissue within the mammal, for example, arthritic diseases (rheumatoid arthritis and osteoarthritis), multiple sclerosis, bone resorptive diseases (such as osteoporosis), the enhanced collagen destruction associated with diabetes, chronic obstructive pulmonary disease, cerebral hemorrhaging associated with stroke, periodontal disease, corneal ulceration, ulceration of the skin, tumor invasion and metastasis, and aberrant angiogenesis.

The compounds of Formula I substantially inhibit the release of tumor necrosis factor (TNF) from cells, and are therefore useful for the treatment of conditions mediated by TNF, for example inflammation, fever, cardiovascular effects, hemorrhage, coagulation and acute phase response, cachexia and anorexia, acute infections, shock states, restinosis, aneurysmal disease, graft versus host reactions and autoimmune disease.

The compounds of Formula I also inhibit the release of other biologically active molecules from cells, including soluble receptors (CD30 and receptors for TNF (p55 and p75), IL-6, IL-1 and TSH), adhesion molecules (e.g., L-selection, ICAM-1, fibronectin) and other growth factors and cytokines, including Fas ligand, TGF-α, EGF, HB-EGF, SCF and M-CSF. Inhibition of the release or shedding of such proteins, and are therefore useful for treating a number of disease states, for example rheumatoid arthritis, multiple sclerosis, vascular disease, Type II diabetes, HIV, cachexia, psoriasis, allergy, hepatitis, inflammatory bowel disease, and cancer.

Testing

The ability of the compounds of Formula I to inhibit matrix metalloprotease activity, such as the activity of collagenase-1, -2 and -3, stromelysin-1, gelatinases A and B, and matrilysin may be demonstrated by a variety of in vitro assays known to those of ordinary skill in the art, such as the assay described in the MMP Enzymatic Assay described in *FEBS,* 296, 263 (1992) or modifications thereof. The ability of the compounds of Formula I to inhibit MMP mediated processes in vivo may be tested using the interleukin-1 stimulated cartilage explant assay and cartilage plug implantation assay.

The ability of the compounds of Formula I to inhibit the release of TNF as shown in Examples 45 to 48.

Administration

Administration of the compounds of Formula I or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of Formula I as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of Formula I, or a pharmaceutically acceptable salt thereof, and 99% to 1% by weight of a suitable pharmaceutical excipient. Preferably, the composition will be about 5% to 75% by weight of a compound(s) of Formula I, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of Formula I, or a pharmaceutically acceptable salt thereof, is formed by the incorporation of any of the normally employed excipients, such as for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations, and the like.

Preferably such compositions will take the form of capsule, caplet or tablet and therefore will also contain a diluent such as lactose, sucrose, dicalcium phosphate, and the like; a disintegrant, such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of Formula I, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of Formula I (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences,* 18th Edition, Mack Publishing Company, Easton, Pa. (1990). The composition to be administered will, in any event, contain a therapeutically effective amount of a compound of Formula I or a pharmaceutically acceptable salt thereof, for treatment of a disease-state alleviated by the inhibition of matrix metalloprotease activity in accordance with the teachings of this invention.

The compounds of Formula I or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-state, and the host undergoing therapy. Generally, a therapeutically effective daily dose is from about 0.014 mg to about 14.3 mg/kg of body weight per day of a compound of Formula I or a pharmaceutically acceptable salt thereof; preferably, from about 0.07 mg to about 5 mg/kg of body weight per day; and most preferably, from about 0.14 mg to about 1.4 mg/kg of body weight per day. For example, for administration to a 70 kg person, the dosage range would be from about 1 mg to about 1.0 gram per day of a compound of Formula I or a pharmaceutically acceptable salt thereof, preferably from about 5 mg to about 300 mg per day, and most preferably from about 10 mg to about 100 mg per day.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of Compounds of Formula (1)

A. Preparation of (1) where $R^3$ and $R^4$ when taken together with the Carbon to which they are attached represent N-CBZ-piperidine 1. A solution of benzyl chloroformate (35 ml, 247 mmol) in tetrahydrofuran (70 ml) was added to an ice-cold solution of 4-hydroxypiperidine (25 g, 247 mmol) and triethylamine (45 ml, 321 mmol) in tetrahydrofuran (350 ml). The mixture was stirred overnight at room temperature and the solvent removed under reduced pressure. The residue was partitioned between 5% hydrochloric acid and ethyl acetate, and the organic layer washed with brine, dried over magnesium sulfate, and the solvent removed under reduced pressure to give 4-hydroxy-N-CBZ-piperidine as a pale yellow oil.

2. Celite (66 g) was added to a solution of 4-hydroxy-N-CBZ-piperidine (18 g, 76.5 mmol) in methylene chloride (500 ml), followed by pyridinium chlorochromate (33 g, 153 mmol). The mixture was stirred overnight, and then isopropyl alcohol (12 ml) was added over a period of 3 hours. The reaction mixture was filtered through silica gel and the filter cake was repeatedly rinsed with methylene chloride and ethyl acetate. The combined filtrates were evaporated under reduced pressure. Silica gel chromatography using 50% ethyl acetate/hexane, gave 4-oxo-N-CBZ-piperidine as a yellow oil.

Example 2

Preparation of Compounds of Formula (3)

2A. Preparation of (3) where $R^2$ is Hydrogen, and $R^3$ and $R^4$ when taken together with the Carbon to which they are attached represent N-CBZ-piperidine tert-(Butoxycarbonylmethylene)triphenylphosphorane (28 g, 74.4 mmol) was added to 4-oxo-N-CBZ-piperidine (14.2 g, 61.3 mmol) in benzene (150 ml), and the solution was stirred at reflux overnight. The solution was concentrated, and the residue triturated with hexane (500 ml). Filtration and concentration of the filtrate gave 4-tert-butoxycarbonylmethylene-N-CBZ-piperidine as a colorless oil.

2B. Preparation of (3), varying $R^2$, $R^3$, and $R^4$

Similarly, following the procedures of Example 2A above, but replacing 4-oxo-N-CBZ-piperidine with:

formaldehyde;
acetone;
propionaldehyde;
cyclopentanone;
cyclohexanone;
1,4-cyclohexanedione mono-ethylene ketal;
4-methylcyclohexanone;
phenylacetaldehyde;
4-(biphen-4-yl)butyraldehyde;
cyclopentylacetaldehyde;
tetrahydropyranone; and
tetrahydrothiopyran;

and optionally replacing tert-(butoxycarbonylmethylene) triphenylphosphorane with:

tert-butyl-3-phenylpropionate-2-triphenylphosphorane;
tert-butyl-propionate-2-triphenylphosphorane; and
tert-butyl-3-methylpropionate-2-triphenylphosphorane;

the following compounds of Formula (3) were prepared:

1-(tert-butoxycarbonyl)-1-benzylethene;
1-(tert-butoxycarbonyl)-2,2-dimethylethene;
1-(tert-butoxycarbonyl)-1-methyl-2-ethylethene;
tert-butoxycarbonylmethylenecyclopentane;
tert-butoxycarbonylmethylenecyclohexane;
tert-butoxycarbonylmethylene-4-methylcyclohexane;
1-(tert-butoxycarbonyl)-2-benzylethene;
1-(tert-butoxycarbonyl)-1-isopropyl-2-benzylethene;
1-(tert-butoxycarbonyl)-2-[3-(biphen-4-yl)]propylethene;
1-(tert-butoxycarbonyl)-2-cyclopentylmethylethene;
4-(tert-butoxycarbonylmethylene)-tetrahydropyran; and
4-(tert-butoxycarbonylmethylene)-tetrahydrothiopyran.

2C. Preparation of (3), varying $R^2$, $R^3$, and $R^4$

Similarly, following the procedures of Example 2A above, but optionally replacing 4-oxo-N-CBZ-piperidine with other compounds of Formula (1), and optionally replacing (tert-butoxycarbonylmethylene)triphenyl-phosphorane with other compounds of Formula (2), other compounds of Formula (3) are prepared.

Example 3

Preparation of Compounds of Formula (4)

3A. Preparation of (4) where $R^2$ is Hydrogen, and $R^3$ and $R^4$ when taken together with the Carbon to which they are attached represent N-CBZ-piperidine, a Compound of Formula (4a)

Trifluoroacetic acid (10 ml) was added to 4-tert-butoxycarbonyl-methylene-N-CBZ-piperidine (20 g, 60.3 mmol) in methylene chloride (30 ml) and the solution was stirred at room temperature for 1.5 hours. After evaporation of the solvent, the residue was triturated with diethyl ether to give 4-carboxymethylene-N-CBZ-piperidine as a crystalline white solid.

3B. Preparation of (4) where $R^2$ is Hydrogen, and $R^3$ and $R^4$ when taken together with the Carbon to which they are attached represent Tetrahydropyran, a Compound of Formula (4b)

Methanol (204 ml) was slowly added to a suspension of sodium hydride (5.48 g, 228.2 mmol) in tetrahydrofuran (204 ml) at 0° C. When addition was complete, trimethylphosphonoacetate (34.22 ml, 211.4 mmol) was added to the mixture at such a rate as to maintain the temperature below 12° C. Stirring was continued for a further 10 minutes. To this reaction mixture was added a solution of 2,3,5,6-tetrahydropyran-4-one (16.28 g, 163.0 mmol) in tetrahydrofuran (20 ml), keeping the temperature below 30° C. After the addition was complete, stirring was continued for 30 minutes at room temperature, then methanol (100 ml) and 2M sodium hydroxide (326 ml) was added, and the mixture stirred overnight at room temperature. The resulting solution was concentrated to one half of the original volume, and acidified to pH 1.2 with 6M hydrochloric acid (108 ml). The reaction mixture was partitioned between ethyl acetate and water, the combined organic extracts dried over magnesium sulfate, and solvent removed under reduced pressure to give 4-(carboxymethylene)-2,3,5,6-tetrahydropyran (22.62 g), which was used with no further purification.

3C. Preparation of (4), varying $R^2$, $R^3$, and $R^4$

Similarly, following the procedures of Example 3A above, but replacing 4-(tert-butoxycarbonylmethylene)-N-CBZ-piperidine with other compounds of Formula (3), the following compounds of Formula (4) were prepared:

1-benzyl-1-carboxyethene;

1-carboxy-2,2-dimethylethene;

1-carboxy-2-ethyl-1-methylethene;

carboxymethylenecyclopentane;

carboxymethylenecyclohexane;

carboxymethylene-(4-methylcyclohexane);

4-carboxymethylenecyclohexanone mono-ethylene ketal;

2-benzyl-1-carboxyethene;

2-[3-(biphen-4-yl)propyl]-1-carboxyethene;

2-benzyl-1-carboxy-1-isopropylethene;

1-carboxy-2-cyclopentylmethylethene;

4-carboxymethylene-tetrahydrothiopyran; and 4-carboxymethylene-(tetrahydrothiopyran-1,1-dioxide).

3D. Preparation of (4), varying $R^2$, $R^3$, and $R^4$

Similarly, following the procedures of Example 3A above, but replacing 4-(tert-butoxycarbonylmethylene)-N-CBZ-piperidine with other compounds of Formula (3), other compounds of Formula (4) are prepared, or may be prepared by means well known to those skilled in the art. Alternatively, they are commercially available, for example, 1-cyclopentene carboxylic acid and 1-cyclohexene carboxylic acid are available from Lancaster Synthesis Inc.

Example 4

Preparation of Compounds of Formula (5)

4A. Preparation of (5) where $R^5$ is 4-Phenoxyphenyl

A solution of sodium thiomethoxide (25 g) and 4-bromodiphenyl ether (25 g) in N,N-dimethylformamide (DMF) (150 ml) was refluxed overnight. The mixture was cooled and added to dilute aqueous sodium hydroxide. The water layer was washed with ether to remove by-products and acidified with hydrochloric acid. The product, 4-(phenoxy)thiophenol, was extracted with ether, and the ether layer dried and evaporated to give 4-(phenoxy)thiophenol (19–20 g) as a red oil. This material can be used without further purification.

4B. Alternative Preparation of (5) where $R^5$ is 4-(4-Bromophenoxy)phenyl

A solution of 4-bromodiphenyl ether (50 g, 200.7 mmol) in methylene chloride (118 mL) was cooled to 0° C. and chlorosulfonic acid (14.7 mL, 220.8 mmol) was added dropwise over a 20 minute period. The solution was stirred an additional 10 minutes, warmed to room temperature and stirred an additional 1 hour. To this mixture was added oxalyl chloride (23.6 mL, 270.9 mmol), followed by N,N-dimethylformamide (1.5 mL) as a catalyst, and the mixture refluxed for 2 hours. The mixture was cooled to room temperature, and additional oxalyl chloride (23.6 mL, 270.9 mmol) was added, the mixture refluxed for 3 hours, cooled to room temperature and stirred 12 hours more. The solution was concentrated to an oil, azeotroped several times using methylene chloride and put under high vacuum (1 torr) for several hours until the mixture had completely solidified. This mixture was immediately dissolved in methylene chloride (160 mL) which was added dropwise to a solution of triphenylphosphine (157.0 g, 602 mmol) in methylene chloride (160 mL) containing N,N-dimethylformamide (4 mL, 52.2 mmol). The mixture was stirred 2 hours, diluted with 1M aqueous hydrochloric acid (300 mL) and stirred for 1 hour. The aqueous layer was separated, extracted with methylene chloride (200 mL), and the organic layers were combined, washed with 200 mL of brine, dried ($MgSO_4$) and concentrated in vacuo. The resulting solid was further purified through trituration with 750 mL of hexane. The solid was then dissolved in 750 mL of diethyl ether, extracted with 2M aqueous sodium hydroxide (2×350 mL), and the basic aqueous layer back extracted using diethyl ether (2×400 mL). The aqueous layer was adjusted to pH 2, extracted with diethyl ether (3×200 mL) and the combined organic layers dried ($MgSO_4$) and concentrated to afford 4-(4-bromophenoxy)thiophenol (45.6 g, 81%). $^1$HNMR ($CDCl_3$) δ 3.43 (s, 1H), 6.86 (d, J=8.9 Hz, 2H), 6.89 (d, J=8.6 Hz, 2H), 7.28 (d, J=8.6 Hz, 2H), 7.43 (d, J=8.9 Hz, 2H).

The corresponding 4-chloro and 4-fluoro analogues were obtained in similar fashion from the corresponding commercially available 4-halodiphenylethers, respectively.

4-(4-chlorophenoxy)thiophenol: $^1$HNMR ($CDCl_3$) δ 3.43 (s, 1H), 6.90 ($m_c$, 4H), 7.27 ($m_c$, 4H).

4-(4-fluorophenoxy)thiophenol: $^1$HNMR ($CDCl_3$) δ 3.41 (s, 1H), 6.85 (d, J=8.7 Hz, 2H), 7.00 (m, 4H), 7.26 (d, J=8.7 Hz, 2H).

4-(4-pyridyloxy)thiophenol: $^1$HNMR ($CDCl_3$) δ 7.05 (d, J=9.0 Hz, 2H), 7.29 (d, J=7.3 Hz, 2H), 7.44 (d, J=8.8 Hz, 2H), 8.70 (d, J=7.3 Hz, 2H); EIMS ($M^+$): 203.

4-(5-chloro-2-pyridyloxy)thiophenol: $^1$HNMR ($CDCl_3$) δ 6.87 (d, J=8.5 Hz, 1H), 7.01 (d, J=8.7 Hz, 2H), 7.32 (d, J=8.7 Hz, 2H), 7.63 (d, J=8.6 Hz, 1H), 8.15 (d, J=2.8 Hz, 1H).

Example 5

Preparation of Compounds of Formula (10)

5A. Preparation of a Compound of Formula (8) where $R^1$ and $R^2$ taken together with the Carbon to which they are attached represent Tetrahydropyran, a Compound of Formula (8a)

A solution of 1.5M diisobutylaluminum hydride (DIBAL-H) (419 mL, 629 mmol) in toluene was added to a 3-L Morton flask equipped with a nitrogen gas inlet, mechanical stirrer, low temperature thermometer, 500 mL pressure equalizing funnel, and containing tetrahydropyran-4,4-dicarboxylic acid diethyl ester (70.78 g, 307.4 mmol) in toluene (600 mL) at –40° C., at a rate to maintain an internal temperature no higher than –25° C. The mixture was stirred an additional 10 minutes and anhydrous ethanol (595 mL) was added dropwise over 20 minutes maintaining an internal temperature no higher than –15° C. Solid sodium borohydride (11.6 g, 307.4 mmol) was added in three portions over a 15 minute period, the cooling bath was removed, the mixture allowed to warm to room temperature over 1 hour, and saturated aqueous sodium sulfate (325 mL) added over 15 minutes. The mixture was cooled to –15° C., ethyl acetate (250 mL) was added, and the flocculent white precipitate filtered over a pad of celite. The celite pad was washed with ethyl acetate (7×450 mL), the filtrate washed with brine (200 mL), dried over magnesium sulfate, and concentrated in vacuo. The residue was dissolved in the minimum amount of ethyl acetate, filtered through a sintered glass funnel containing silica gel (40 g), eluting with ethyl acetate, and the filtrate concentrated in vacuo to afford the hydroxyester, 4-(hydroxymethyl)tetrahydropyran-4-carboxylic acid ethyl ester, as a pale yellow oil (48.5 g, 84%).

5B. Alternative Preparation of a Compound of Formula (8) where $R^1$ and $R^2$ taken together with the Carbon to which they are attached represent Tetrahydropyran 1. To a solution of tetrahydropyran-4,4-dicarboxylic acid diethyl ester (400 mg, 1.74 mmol) in N,N- dimethylformamide (4 mL), was added lithium iodide (1.16 g, 8.66 mmol), followed by sodium cyanide (94 mg, 1.91 mmol). The mixture was heated at 130° C. for 7 hours, 140° C. for 25 hours, after which GC analysis indicated the reaction to be >95% complete. The mixture was partitioned between 33% diethyl ether/hexanes (100 mL) and brine (25 mL). The organic layer was washed with additional brine (25 mL), dried (MgSO$_4$) and concentrated in vacuo to afford the tetrahydropyran-4-carboxylic acid ethyl ester (253 mg, 92%). Note: Substitution of 2 equivalents of sodium acetate for 1.1 equivalents of sodium cyanide in this reaction and heating 12 hours longer provides identical results.

2. Lithium diisopropylamide was prepared by the addition of 2.5M N-butyl lithium (30.3 mL, 75.6 mmol) in hexanes to a solution of diisopropylamine (10.6 mL, 75.6 mmmol) in tetrahydrofuran (244 mL) at 0° C. and stirring for 20 minutes. Then a solution of tetrahydropyran-4-carboxylic acid ethyl ester (10 g, 63.2 mmol) in tetrahydrofuran (50 mL) was added to the solution of lithium diisopropylamide over 15 minutes at −78° C. The resulting solution was stirred an additional 50 minutes, and solid paraformaldehyde (10 g) was added in one portion. The mixture was slowly allowed to warm to room temperature over 9 hours, diluted with 2M aqueous hydrochloric acid (100 mL), and filtered over a pad of celite pad which was washed with diethyl ether (2×200 mL). The aqueous layer of the filtrate was washed with additional portions of diethyl ether (2×200 mL). The combined organic layers were washed once with 2M aqueous hydrochloric acid (100 mL), saturated aqueous sodium bicarbonate (100 mL), dried over magnesium sulfate, and concentrated in vacuo to afford a slightly impure product 4-(hydroxymethyl)tetrahydropyran-4-carboxylic acid ethyl ester (11.5 g, 97%), which was taken into the next reaction without further purification. IR (neat) 3433 (br), 1726 cm$^{-1}$; $^1$HNMR (CDCl$_3$) δ 1.30 (t, J=7.1 Hz, 3H), 1.57 (ddd, J=13.8, 10.1, 4.4 Hz, 2H), 2.07 (dm, J=13.8 Hz, 2H), 2.30–2.45 (br s, 1H), 3.56 (ddd, J=11.9, 10.3, 2.7 Hz, 2H), 3.66 (s, 2H), 3.82 (dt, J=11.9, 4.2 Hz, 2H), 4.24 (q, J=7.2 Hz, 2H); $^{13}$CNMR (CDCl$_3$) δ 14.25 (q), 30.54 (t), 46.63 (s), 61.04 (t), 64.79 (t), 69.02 (t), 175.24 (s); HRMS Calcd for C$_9$H$_{16}$O$_4$: 188.1049. Found: 188.1053.

5C. Preparation of a Compound of Formula (8) where R$^1$ and R$^2$ taken together with the Carbon to which they are attached represent Piperidine, a Compound of Formula (8)

Lithium diisopropylamide was prepared by the addition of 1.6M N-butyl lithium (29.1 mL, 46.6 mmol) in hexanes to a solution diisopropylamine (6.5 mL, 46.6 mmmol) in tetrahydrofuran (150 mL) at 0° C. with stirring for 20 minutes at −78° C. Then a solution of neat N-(tert-butoxycarbonyl)-piperidine-4-carboxylic acid ethyl ester (10 g, 38.9 mmol) was added over 5 minutes, and the resulting solution was stirred an additional 50 minutes. Solid paraformaldehyde (13.5 g, 155.4 mmol) was added in one portion, and the mixture slowly allowed to warm to room temperature over 9 hours. The mixture was diluted with 2M aqueous hydrochloric acid (100 mL), filtered over a pad of celite, washed with diethyl ether (2×200 mL). The combined organic layers were washed once with 2M aqueous hydrochloric acid (100 mL), saturated aqueous sodium bicarbonate (100 mL), dried over magnesium sulfate, and concentrated in vacuo. Chromatography on silica gel, and eluting with 50% ethyl acetate/hexanes, yielded slightly impure N-(tert-butoxycarbonyl)-4-(hydroxymethyl)piperidine-4-carboxylic acid ethyl ester (10.57 g, 95%) as a pale yellow oil which was taken immediately into the hydrolysis reaction (LiOH): $^1$H NMR (CDCl$_3$) δ 1.26 (t, J=7.4 Hz, 3H), 1.40–1.53 (m, 2H), 1.46 (s, 9H), 2.00–2.12 (m, 2H), 3.05–3.16 (m, 2H), 3.65 (s, 2H), 3.70–3.83 (m, 2H), 4.23 (q, J=7.2 Hz, 2H).

5D. Preparation of a Compound of Formula (9) where R$^1$ and R$^2$ taken together with the Carbon to which they are attached represent Tetrahydropyran, a Compound of Formula (9a)

Lithium hydroxide monohydrate (16.7 g, 398.5 mmol) was added to a solution of 4-(hydroxymethyl) tetrahydropyran-4-carboxylic acid ethyl ester (25.0 g, 132.8 mmol) in 4.5:1 methanol/water (220 mL). The mixture was heated to reflux for 40 minutes and the methanol removed in vacuo by concentration using a bath temperature no higher than 45° C. The aqueous layer was then extracted into diethyl ether (4×100 mL) and the combined ether layers washed twice with 2M sodium hydroxide (15 mL). The combined aqueous base layers were cooled to 0° C., acidified to pH 3.0 with 8M aqueous hydrochloric acid, saturated with solid sodium chloride and extracted with ethyl acetate (8×250 mL). The combined organic layers were dried over magnesium sulfate, concentrated in vacuo. The white fluffy powder residue was recrystallized from the minimum amount of methylene chloride/hexanes to afford pure 4-(hydroxymethyl)tetrahydropyran-4-carboxylic acid (17.05 g, 80%).

5E. Alternative Preparation of a Compound of Formula (9) where R$^1$ and R$^2$ taken together with the Carbon to which they are attached represent Tetrahydropyran Lithium diisopropylamide was prepared by the addition of 2.45M N-butyl lithium (16.5 mL) in hexanes to a solution diisopropylamine (5.80 mL, 41.4 mmmol) in tetrahydrofuran (40 mL) at 0° C. with stirring for 20 minutes. Then a solution of tetrahydropyran-4-carboxylic acid (2.5 g, 19.2 mmol) in tetrahydrofuran (10 mL) was added to the solution of lithium diisopropylamide over 15 minutes to form a slurry, followed by hexamethylphosphoramide (2 mL). The resulting solution was stirred for 25 minutes, then immediately warmed to room temperature after a stream of gaseous formaldehyde (prepared by heating 4 g of paraformaldehyde at 175–200° C. over 5–10 minutes) was passed through the solution. The slurry was carefully concentrated at ambient temperature, acidified to pH 3 with 8M hydrochloric acid, saturated with solid sodium chloride, and extracted with ethyl acetate (8×100 mL). The combined organic layers were dried over magnesium sulfate, concentrated in vacuo. Chromatography over silica gel (80 g), and eluting with 10% methanol/methylene chloride, yielded 4-(hydroxymethyl) tetrahydropyran-4-carboxylic acid as a white solid (1.80 g, 58%). mp 113.7–115° C.; IR (KBr) 3420 (br), 1724 cm$^{-1}$, $^1$HNMR (DMSO-d$_6$) δ 1.43 (ddd, J=13.5, 11.0, 4.4 Hz, 2H), 1.85 (dm, J=13.4 Hz, 2H), 3.37 (td, J=11.3, 3.0 Hz, 2H), 3.43 (s, 2H), 3.71 (dt, J=11.6, 3.9 Hz, 2H), 4.81 (br, s, 1H); 12.24 (s, 1H); $^{13}$CNMR (DMSO-d$_6$) δ 30.42 (t), 46.38 (s), 64.35 (t), 68.15 (t), 69.02 (t), 176.08 (s); HRMS Calcd. for C$_7$H$_{12}$O$_4$: 160.0735. Found: 160.0731. Anal. Calcd. for C$_7$H$_{12}$O$_3$: C, 52.49; H, 7.55. Found: C, 52.50; H, 7.62.

5F. Preparation of a Compound of Formula (9) where R$^1$ and R$^2$ taken together with the Carbon to which they are attached represent Piperidine, a Compound of Formula (9b)

Lithium hydroxide monohydrate (6.95 g, 165.6 mmol) was added to solution of N-(tert-butoxycarbonyl)-4-(hydroxymethyl)piperidine-4-carboxylic acid ethyl ester (9.52 g, 33.1 mmol) in 2:1 methanol/water (100 mL). The mixture was heated to reflux for 30 minutes, the methanol removed in vacuo by concentration using a bath temperature no higher than 45° C. The aqueous layer was cooled to 0° C., acidified to pH 3.0 using 6M aqueous hydrochloric acid, and extracted with ethyl acetate (4×75 mL). The combined organic layers were dried over magnesium sulfate, and concentrated in vacuo, and recrystallized from dichloromethane/hexanes to afford N-(tert-butoxycarbonyl)-4-(hydroxymethyl)piperidine-4-carboxylic acid (8.59 g, 100%).

5G. Alternative Preparation of a Compound of Formula (9) where $R^1$ and $R^2$ taken together with the Carbon to which they are attached represent Piperidine Lithium diisopropylamide was prepared by the addition of 2.45M N-butyllithium (69 mL, 168.8 mmol) in hexanes to a solution diisopropylamine (24 mL, 171.2 mmmol) in tetrahydrofuran (40 mL) at 0° C. with stirring for 20 minutes. Then a solution of N-(tert-butoxycarbonyl)piperidine-4-carboxylic acid (18 g, 78.5 mmol) in tetrahydrofuran (35 mL) was added to the solution of lithium diisopropylamide over 15 minutes to form a slurry, followed by hexamethylphosphoramide (2 mL). The resulting solution was stirred for 25 minutes, then stream of gaseous formaldehyde (prepared by heating paraformaldehyde (16.4 g, 189 mmol) at 175–200° C. over 5–10 minutes) was passed through the solution, which was allowed to immediately warm to room temperature. The slurry was concentrated at ambient temperature, acidified to pH 4 with 6M hydrochloric acid, saturated with solid sodium chloride, and extracted with ethyl acetate (8×100 mL). The combined organic layers were dried over magnesium sulfate, concentrated in vacuo. Chromatography over silica gel, and eluting with 1% methanol/methylene chloride, afforded N-(tert-butoxycarbonyl)-4-(hydroxymethyl)piperidine-4-carboxylic acid as a white solid (4 g, 20%). mp 156.6–157.3° C.; $^1$HNMR (DMSO-$d_6$) δ 1.25–1.37 (m, 2H), 1.38 (s, 9H), 1.85 (dm, J=13.7 Hz, 2H), 2.78–2.94 (br m, 2H), 3.41 (s, 1H), 3.70 (dm, J=12.8 Hz, 2H), 4.87 (br s, 1H), 12.34 (s, 1H); Anal. Calcd. for $C_{12}H_{21}NO_5$: C, 55.58; H, 8.16; N, 5.40. Found: C, 55.72; H, 8.10; N, 5.53.

5H. Preparation of (10) where $R^1$ and $R^2$ taken together with the Carbon to which they are attached represent Tetrahydropyran, a Compound of Formula (10a)

Trifluoromethanesulfonic anhydride (11.1 mL, 66.2 mmol), followed by triethylamine (17.8 mL, 127.4 mmol) was added to a slurry of 4-(hydroxymethyl)tetrahydropyran-4-carboxylic acid (10.20 g, 63.68 mmol) in anhydrous diethyl ether cooled to 0° C. (115 mL). The biphasic solution was stirred for 20 hours, warmed to room temperature, stirred an additional 2 hours. The layers were separated by decantation, and the lower layer diluted with 2% aqueous sodium bicarbonate solution (50 mL) and extracted with methylene chloride (4×200 mL). The combined organic extracts were washed with additional 2% aqueous sodium bicarbonate (100 mL), dried over magnesium sulfate, and concentrated in vacuo to afford 2,7-dioxaspiro[3.5]nonane-1-one as a pale yellow oil (10.8 g). IR (KBr) 1821 cm$^{-1}$; $^1$HNMR (CD$_3$Cl$_3$) δ 1.92 (ddd, J=13.4, 8.1, 4.0 Hz, 2H), 2.10 (dddd, J=13.4, 6.1,3.4, 0.8 Hz, 2H), 3.70 (ddd, J=11.8, 6.3, 3.9 Hz, 2H), 3.92 (ddd, J=11.8, 7.9, 3.4 Hz, 2H), 4.15 (s, 2H); $^{13}$CNMR (CD$_3$Cl$_3$) δ 30.78 (t), 55.78 (s), 64,46 (t), 71.50 (t), 173.42 (s), MS(EI) m/e=142. MS(CI) M+=H m/e=143, M++HNH$_4$ m/e=160.

5I. Preparation of a Compound of Formula (10) where $R^1$ and $R^2$ taken together with the Carbon to which they are attached represent Piperidine, a Compound of Formula (10b)

Trifluoromethanesulfonic anhydride (2.60 mL, 15.39 mmol), followed by triethylamine (4.30 mL, 30.78 mmol) was added to a slurry of N-(tert-butoxycarbonyl)-4-hydroxymethylpiperidine-4-carboxylic acid (3.80 g, 14.65 mmol) in anhydrous diethyl ether (27 mL) cooled to 0° C. The biphasic solution was stirred for 23 hours, warmed to room temperature, stirred an addition 1 hour, and the upper diethyl ether layer separated by decantation. The lower was extracted with additional portions of diethyl ether (2×100 mL), and the combined organic extracts washed with aqueous sodium bicarbonate solution (2×50 mL), dried over magnesium sulfate, and concentrated in vacuo to afford 7-(butoxycarbonyl)-2-oxa-7-azaspiro[3.5]nonan-1-one as a pale yellow oil (2.88 g, 82%). $^1$HNMR (CDCl$_3$) δ 1.48 (s, 9H), 1.79–1.89 (m, 2H), 2.02–2.10 (m, 2H), 3.48–3.66 (m, 4H), 4.13 (s, 2H).

Example 6

Preparation of a Compound of Formula (13)

6A. Preparation of (13) where $R^1$ and $R^2$ taken together with the Carbon to which they are attached represent Tetrahydropyran, and X is Iodo Lithium diisopropylamide was prepared by the addition of 2.5M N-butyl lithium (5.6 mL, 13.9 mmol) in hexanes to a solution of diisopropylamine (1.95 mL, 13.9 mmmol) in tetrahydrofuran (30 mL) at 0° C. with stirring for 20 minutes. Then a solution of tetrahydropyran-4-carboxylic acid ethyl ester (2 g, 12.7 mmol) in tetrahydrofuran (8 mL) was added to the solution of lithium diisopropylamide at a temperature of −78° C. over 15 minutes. The resulting solution was stirred an additional 50 minutes, and diiodomethane (1.14 mL, 14.2 mmol) was added. The resulting mixture was stirred an additional 50 minutes, warmed to room temperature over 30 minutes, then recooled to 0° C. The mixture was diluted with 1M aqueous hydrochloric acid (25 ml), extracted with diethyl ether (2×100 mL), and washed with additional portions of diethyl ether (2×50 mL). The combined organic layers were washed once with 1M aqueous hydrochloric acid (100 mL), saturated aqueous sodium bisulfite (100 mL), saturated aqueous sodium bicarbonate (100 mL), and dried over magnesium sulfate, and concentrated in vacuo. The residue was filtered over a plug of silica gel, eluting successively with hexanes and ethyl acetate, removing excess alkylating agent with the hexane wash, to afford pure 4-(iodomethyl)tetrahydropyran-4-carboxylic acid ethyl ester as a pale yellow oil which was taken directly into the next reaction without further purification (3.20 g, 85%). IR (KBr) 1732 cm$^{-1}$; $^1$HNMR (CDCl$_3$) 1.31 (q, J=7.3 Hz, 3H), 1.56 (ddd, J=14.6, 10.9, 4.5, 2H), 2.17 (ddd, J=14.6, 5.7, 3.3, 2H), 3.31 (s, 2H), 3.51 (ddd, J=11.7, 11.1, 2.5 Hz, 2H), 3.51 (td, J=11.7, 4.3 Hz, 2H), 4.24 (q, J=7.1 Hz, 2H); $^{13}$CNMR (CDCl$_3$) δ 14.33 (q), 15.04 (t), 34.70 (t), 45.26 (s), 61.34 (t), 65.22 (t), 172.89 (s); EIHRMS Calcd. for $C_9H_{15}IO_3$ (M$^+$): 298.0066. Found: 298.0066. Anal. Calcd. for $C_9H_{15}IO_3$: C, 36.26; H, 5.07. Found: C, 36.56; H, 5.09.

6B. Preparation of (13) where $R^1$ and $R^2$ taken together with the Carbon to which they are attached represent Tetrahydropyran, and Varying X Similarly, replacing diiodomethane with dibromomethane or bromochloromethane, the following compounds of Formula (13) were prepared:

4-(bromomethyl)tetrahydropyran-4-carboxylic acid ethyl ester: IR (neat) 1732 cm$^{-1}$; $^1$HNMR (CDCl$_3$) 1.30 (q, J=7.1 Hz, 3H), 1.59 (ddd, J=14.6, 10.9, 4.5, 2H), 2.17 (dm, J=14.7, 2H), 3.48 (s, 2H), 3.53 (dt, J=11.9, 4.5 Hz, 2H), 3.84 (dt, J=11.9, 4.5 Hz, 2H), 4.23 (q, J=7.1 Hz, 2H); $^{13}$CNR (CDCl$_3$) δ 14.27 (q), 33.17 (t), 40.16 (t), 46.05 (s), 61.29 (t), 64.97 (t), 172.91 (s); CIMS (M$^+$+H): 251, (M$^+$+NH$_4$+) 268.

4-(chloromethyl)tetrahydropyran-4-carboxylic acid ethyl ester: IR (neat) 1734 cm$^{-1}$; $^1$HNMR (CDCl$_3$) 1.30 (q, J=7.1 Hz, 3H), 1.59 (ddd, J=14.6, 10.9, 4.5, 2H), 2.16 (dm, J=14.7, 2H), 3.53 (dt, J=11.9, 4.5 Hz, 2H), 3.61 (s, 2H), 3.84 (dt, J=11.7, 4.3 Hz, 2H), 4.24 (q, J=7.1 Hz, 2H); $^{13}$CNMR (CDCl$_3$) δ 14.24 (q), 32.14 (t), 46.69 (s), 51.40 (t), 61.29 (t), 64.85 (t), 173.01 (s); CIMS (M$^+$+H): 207. Anal. Calcd. for C$_9$H$_{15}$ClO$_3$: C, 52.31; H, 7.32. Found: C, 52.51; H, 7.30.

6C. Alternative Preparation of a Compound of Formula (13) where R$^1$ and R$^2$ taken together with the Carbon to which they are attached represent Tetrahydropyran, and X is p-Tosyl To a solution of tetrahydropyran-4-carboxylic acid ethyl ester (820 mg, 4.356 mmol) in pyridine (10 mL) at 0° C., was added p-toluenesulfonyl chloride (997 mg, 5.23 mmol), and the mixture allowed to warm to room temperature over 1 hour period. The mixture was stirred 36 hours and partitioned between methylene chloride (150 mL) and 3N aqueous hydrochloric acid (50 mL). The organic layer was washed with 25 mL of saturated aqueous sodium bicarbonate, dried (MgSO$_4$), concentrated and the residue chromatographed over 45 g of silica gel, eluting with 30% ethyl acetate/hexanes, to afford the tosylate as a white solid (1.03 g, 69%). mp 87.7–88.6° C.; IR (KBr) 1717 cm$^{-1}$; $^1$NMR (CDCl$_3$) δ 1.21 (q, J=17.1 Hz, 3H), 1.52 (ddd, J=13.4, 10.6, 4.1 Hz, 2H), 2.00 (dm, J=13.4 Hz, 2H), 2.46 (s, 3H), 3.49 (ddd, J=11.7, 10.6, 2.5 Hz, 2H), 3.76 (dt, J=11.9, 4.1 Hz, 2H), 4.03 (s, 2H), 4.13 (q, J=7.1 Hz, 2H), 7.35; $^{13}$C NMR (CDCl$_3$) δ 14.10 (q), 21.67 (q), 30.43 (t), 44.93 (s), 61.37 (t), 64.43 (t), 74.65 (t), 127.95 (d), 129.89 (d), 132.67 (s), 145.05 (s), 172.57 (s); HRMS Calcd for C$_{16}$H$_{22}$O$_6$: 343.1215. Found: 343.1217. Anal. Calcd. for C$_{16}$H$_{22}$O$_6$: C, 56.12; H, 6.48. Found: C, 56.22; H, 6.46.

Example 7

Preparation of Compounds of Formula Ia

7A. Preparation of Ia where R$^1$ and R$^2$ are Hydrogen, R$^3$ and R$^4$ when taken together with the Carbon to which they are attached represent Piperidine, and R$^5$ is Diphenylether, from a Compound of Formula (4)

1. 4-Phenoxythiophenol (7.4 g, 36.3 mmol), 4-carboxymethylene-N-CBZ-piperidine (10 g, 36.3 mmol) and piperidine (1.8 ml, 36.3 mmol) were stirred overnight at 100–110° C. in a sealed flask. After cooling, the crude reaction mixture was partitioned between ethyl acetate and 1N hydrochloric acid, the organic layer was washed with brine, dried over magnesium sulfate, filtered, and concentrated in vacuo to give a yellow solid. The solid was triturated in 1:1 (v/v) ethyl ether/hexane (500 ml) to give 2-[4-(4-phenoxyphenylthio)-N-CBZ-piperidin-4-yl]-acetic acid as a white solid.

2. A solution of 2-[4-(4-phenoxyphenylthio)-N-CBZ-piperidin-4-yl)]-acetic acid (150 mg, 0.29 mmole) in dry 1,2 dichloroethane (3 ml) under nitrogen was cooled to –10° C. and saturated with hydrochloric acid gas for 15 minutes. The reaction vessel was then sealed and the solution stirred for two days at 25° C. The tube was cooled to –10° C. prior to opening to release gaseous hydrochloric acid, and then allowed to warm to 25° C. The solvent was removed in vacuo and the product triturated with ethyl acetate to give 2-[4-(4-phenoxyphenylthio)-piperidin-4-yl)]-acetic acid hydrochloride as a white powder. $^1$HNMR (CD$_3$OD): 7.93 (d,2H); 7.45 (t,2H); 7.27 (t,1H), 7.14 (t,4H); 3.52 (m,2H); 3.25 (m,2H); 2.70 (s,2H), 2.35 (m,4H).

7B. Preparation of Ia where R$^1$ and R$^2$ are Hydrogen, R$^3$ and R$^4$ when taken together with the Carbon to which they are attached represent Cyclopentyl, and R$^5$ is Diphenylether, from a Compound of Formula (4)

A mixture of cyclopentylideneacetic acid (2 mmol) and p-(phenoxy)-thiophenol (2 mmol) was heated at 110° C. under nitrogen in the presence of piperidine (100 μL) for 24 hours. The residue was dissolved in ethyl acetate and washed with dilute hydrochloric acid. The organic layer was separated, dried and evaporated under reduced pressure to give crude 2-[-(4-phenoxyphenylthio)-cyclopent-1-yl]-acetic acid, which can be used in the next reaction without further purification.

7C. Preparation of Ia where R$^1$, R$^2$ and R$^3$ are Hydrogen, R$^4$ is Benzyl, and R$^5$ is 4-Bromophenyl A mixture of E-2-benzylacrylic acid (1 g) and p-bromothiophenol (1.12 g) were stirred overnight at 110° C. in the presence of piperidine (300 μL). The residue was partitioned between ethyl acetate and dilute hydrochloric acid. The organic layer was separated, dried and evaporated under reduced pressure to give 3-benzyl-3-(4-bromophenylthio)-propionic acid (Iaa), which was used in the next reaction with no further purification.

7D. Preparation of Ia where R$^1$ and R$^2$ when taken together with the Carbon to which they are attached represent Tetrahydropyran, R$^3$ and R$^4$ are Hydrogen, and R$^5$ is 4-(4-Chlorophenoxy)phenyl, from a Compound of Formula (10)

2,7-dioxa-spiro[3.5]nonane-1-one (10.8 g), obtained as described in Example 5H, was immediately dissolved in N,N-dimethylformamide (95 mL) and slowly added to a solution containing the sodium salt of 4-(4-chlorophenoxy) thiophenol (generated by the addition of sodium hydride powder (2.14 g, 89.2 mmol) to a solution of 4-(4-chlorophenoxy)thiophenol (15.83 g, 66.8 mmol) in N,N-dimethylformamide (19 mL) at 0° C. and stirring for 30 minutes) over a 10–15 minute period, and then stirred an additional 15 minutes. The resulting slurry was heated to 40° C., stirred for 5 minutes, tert-butanol (2 mL) was added, and the mixture cooled to room temperature over 20 minutes. The majority of the N,N-dimethylformamide was removed in vacuo, the pH adjusted to 9.2, the resultant slurry diluted with 30% diethyl ether-hexanes (120 mL) and filtered. The filter cake was washed with additional portions of ether (3×70 mL), acidified to pH 3.5 with 2N aqueous hydrochloric acid, and extracted into methylene chloride (4×350 mL). The combined organic layers were dried over magnesium sulfate, concentrated in vacuo. The solid residue was recrystallized from the minimum amount of methylene chloride-hexanes to afford pure 4-[4-(4-chlorophenoxy) phenylthiomethyl]tetrahydropyran-4-carboxylic acid as a white crystalline solid (19.50 g). mp 140.6–141.9° C.; IR (Ker) 3429 (br), 1732 cm$^{-1}$; $^1$HNMR (DMSO-d$_6$) δ 1.54 (ddd, J=14.2, 10.0, 4.2 Hz, 2H), 1.95 (dm, J=14.2 Hz, 2H), 3.19 (s, 2H), 3.56 (ddd, J=11.8, 10.0, 4.2 Hz, 2H), 3.70 (dt, J=11.8, 4.2 Hz, 2H), 6.98 (d, J=8.8 Hz, 2H), 7.02 (d, J=8.9 Hz, 2H), 7.02 (d, J=8.9 Hz, 2H), 7.42 (d, J=9.0 Hz, 4H), 12.66 (s, 1H); $^{13}$CNMR (DMSO-d$_6$) δ 33.06 (t), 43.56 (t), 45.03 (s), 64.13 (t), 119.43 (d), 120.11 (d), 110.43 (d), 127.35 (s), 129.80 (d), 131.09 (s), 131.59 (d), 154.90 (s), 155.50 (s), 175.25 (s); HRMS Cald. for C$_{19}$H$_{19}$SO$_4$Cl: 378.0693. Found: 378.0685. Anal. Calcd. for C$_{19}$H$_{19}$SO$_4$Cl.0.25 H$_2$O: C,59.53; H, 513. Found: C, 59.53; H, 5.07.

Similarly, replacing 4-(4-chlorophenoxy)thiophenol with 4-(4-bromophenoxy)thiophenol and 4-(4-fluorophenoxy) thiophenol, the following compounds were prepared:

4-[4-(4-bromophenoxy)phenylthiomethyl] tetrahydropyran-$^4$-carboxylic acid: mp 143.7–144.5° C.; IR (Ker) 3434 (br), 1732 cm$^{-1}$; $^1$H NMR (DMSO-d$_6$) δ 1.54 (ddd, J=13.8, 10.1, 4.3 Hz, 2H), 1.94 (dm, J=13.5 Hz, 2H), 3.19 (s, 2H), 3.37 (ddd, J=11.8, 10.1, 2.5 Hz, 2H), 3.70 (dt, J=11.8 Hz, 4.0 Hz, 2H), 6.96 (d, J=9.2 Hz, 2H), 6.98 (d, J=8.8 Hz, 2H), 7.41 (d, J=8.8 Hz, 2H), 7.55 (d, J=9.0 Hz, 2H), 12.68 (s, 1H); $^{13}$C NMR (DMSO-d$_6$) δ 33.04 (t), 43.34 (t), 45.00 (s), 64.10 (t), 115.14 (s), 119.59 (d), 120.53 (d), 131.15 (s), 131.51 (d), 132.77 (s), 154.71 (s), 156.06 (s), 175.28 (s); EIMS (M$^+$): 424. Anal. Calcd. for C$_{19}$H$_{19}$SO$_4$Br: C, 53.91; H, 4.52. Found: C, 53.53; H, 4.54;

4-[4-[4-(4-fluorophenoxy)phenylthiomethyl] tetrahydropyran-4-carboxylic acid: mp 143.0–143.4° C.; IR (KBr) 3436 (br), 1721 cm$^{-1}$; $^1$H NMR (DMSO-d$_6$) δ 1.54 (ddd, J=13.5, 10.1, 4.0 Hz, 2H), 1.94 (dm, J=13.5 Hz, 2H), 3.17 (s, 2H), 3.38 (td, J=11.8, 2.5 Hz, 2H), 3.70 (dt, J=11.8 Hz, 4.0 Hz, 2H), 6.93 (d, J=8.8 Hz, 2H), 7.05 (dd, J=9.2. 4.6 Hz, 2H), 7.21 (dd, J=9.1, 8.4 Hz, 2H), 7.40 (d, J=8.8 Hz, 2H), 12.65 (s, 1H); $^{13}$C NMR (CDCl$_3$) δ 33.05 (t), 43.65 (t), 45.49 (s), 64.12 (t), 116.53 (dd, J$_{C-F}$=23.2 Hz), 118.71 (d), 120.63 (dd, J$_{C-F}$=8.5 Hz), 130.31 (s), 131.69 (d), 152.38 (s), 155.85 (s), 158.29 (d, J$_{C-F}$=239.9 Hz), 175.28 (s); EIMS (M$^+$): 362. Anal. Calcd. for C$_{19}$H$_{19}$SO$_4$F: C, 62.97; H, 5.28. Found: C, 62.79; H, 5.26.

7E. Alternative Preparation of Ia where R$^1$ and R$^2$ are both Methyl, R$^3$ and R$^4$ are Hydrogen, and R$^5$ is 4-(4-Chlorophenoxy)phenyl Sodium hydride powder (0.86 g, 35.8 mmol) was added to a mixture of 4-(4-chlorophenoxy)thiophenol (3.55 g, 15 mmol) in N,N-dimethylformamide (12 mL) at 0° C. The mixture was warmed to room temperature over 5 minutes, stirred for an additional 20 minutes, and solid chloropivalic acid (1.64 g, 12.0 mmol) was added in one portion. This mixture was heated to 80° C. for 18 hours, cooled to room temperature, and water (1 mL) added. The residue was partitioned between methylene chloride (50 mL) and 2N hydrochloric acid (25 mL). The aqueous layer was separated and washed with additional methylene chloride (2×25 mL). The combined organic extracts were dried over magnesium sulfate, concentrated in vacuo. Chromatography over silica gel, and eluting with 5% methanol/methylene chloride, gave slightly impure 3-[4-(4-chlorophenoxy)phenylthio]-2,2-dimethyl propionic acid (4 g, 99%). This material was recrystallized from the minimum amount of diethyl ether/hexanes to afford analytically pure acid as a white solid (3.20 g, 80%). mp 84.4–84.9° C.; IR (KBr) 3433 (br), 1732 cm$^{-1}$; $^1$HNMR (DMSO-d$_6$) δ 1.19 (s, 6H), 3.14 (s, 2H), 6.97 (d, J=8.7 Hz, 2H), 7.01 (d, J=8.9, 2H), 7.40 (d, J=8.8 Hz, 2H), 12.36 (br s, 1H). EIMS(M+): 378. Anal. Calcd. for C$_{17}$H$_{17}$SO$_3$Cl: C, 60.62; H, 5.09. Found: C, 60.31; H, 4.96.

7F. Preparation of Ia where R$^1$ and R$^2$ when taken together with the Carbon to which they are attached represent N-BOC-Piperidine, R$^3$ and R$^4$ are Hydrogen, and R$^5$ is 4-(4-Chlorophenoxy)phenyl, from a Compound of Formula (10b)

7-(tert-Butoxycarbonyl)-2-oxa-7-azaspiro[3.5]nonan-1-one obtained in Example 5I above, was immediately dissolved in N,N-dimethylformamide (4 mL), slowly added to a solution containing the sodium salt of 4-(4-chlorophenoxy)thiophenol (generated by the addition of sodium hydride power (340 mg, 14.17 mmol) to a solution of 4-(4-chlorophenoxy)thiophenol (3.00 g, 12.7 mmol) in N,N-dimethylformamide (19 mL), at 0° C. and stirred for 30 minutes) over a 10–15 minute period, and was stirred an additional 15 minutes. The resulting slurry was heated to 80° C., stirred for 5 minutes, tert-butanol (2 mL) added, and the mixture cooled to room temperature over 20 minutes. The majority of the N,N-dimethylformamide was removed in vacuo, the pH adjusted to 3.5 using 2M aqueous hydrochloric acid and extracted into ethyl acetate (4×150 mL). The combined organic layers were dried over magnesium sulfate, concentrated in vacuo and the residue chromatographed over silica gel, eluting with 1% to 10% methanol/methylene chloride, to afford the piperidine acid, 4-[4-(4-chlorophenoxy)phenylthiomethyl]-N-(tert-butoxycarbonyl)-piperidin-4-yl carboxylic acid as a pale yellow oil (5 g, 89%). $^1$HNMR (OH not observed; CDCl$_3$) δ 1.37 (s, 9H), 1.55 (m$_c$, 2H), 2.10 (m$_c$, 2H), 3.05 (m$_c$, 2H), 3.06 (s, 2H), 3.72 (m$_c$, 2H), 6.81 (d, J=8.8 Hz, 2H), 6.85 (d, J=8.9 Hz, 2H), 7.21 (d, J=8.9 Hz, 2H), 7.30 (d, J=8.7 Hz, 4H).

7G. Preparation of Ia where R$^1$ and R$^2$ when taken together with the Carbon to which they are attached represent Tetrahydronyran, R$^3$ and R$^4$ are Hydrogen, R$^5$ is 4-(4-Chlorophenoxy)phenyl, from a Compound of Formula Ia where R is Ethyl To a solution of 4-[4-(4-chlorophenoxy) phenylthiomethyl]tetrahydropyran-4-carboxylic acid ethyl ester (70 mg, 0.17 mmol) in ethanol (2 mL) containing two drops of water, was added potassium hydroxide (58.3 mg, 1.04 mmol). The mixture was refluxed for 13 hours, cooled to room temperature, acidified to pH 4, and extracted with ethyl acetate (4×50 mL). The combined organic layers were dried over magnesium sulfate, and concentrated to afford 4-[4-(4-chlorophenoxy)phenylthiomethyl]-tetrahydropyran-4-carboxylic acid (66 mg, 100%), which is spectroscopically identical to that isolated from the prior procedure of Example 7D.

7H. Preparation of Ia where R$^1$ and R$^2$ when taken together with the Carbon to which they are attached represent Tetrahydropyran, R$^3$ and R$^4$ are Hydrogen, R$^5$ is 4-(4-Bromophenoxy)phenyl, from a Compound of Formula Ia where R is Ethyl Similarly, following the procedure of Example 7G above, 4-[4-(4-bromophenoxy)phenylthiomethyl]-tetrahydropyran-4-carboxylic acid and 4-[4-(4-fluorophenoxy) phenylthiomethyl]-tetrahydropyran-4-carboxylic acid were prepared.

7I. Preparation of Ia where R$^1$ and R$^2$ when taken together with the Carbon to which they are attached represent Tetrahydropyran, R$^3$ and R$^4$ are Hydrogen, R$^5$ is 4-(4-Chlorophenoxy)phenyl, and R is Methyl, from the Corresponding Carboxylic Acid To a solution of 4-[4-(4-chlorophenoxy) phenylthiomethyl]tetrahydropyran-4-carboxylic acid (580 mg, 1.53 mmol) and N,N-dimethylformamide catalyst (22 μL) in methylene chloride (15 mL) at 0° C. was added oxalyl chloride (0.33 mL, 3.83 mmol) dropwise over 10 minutes. The mixture was warmed to room temperature over 1 hour, the partial slurry stirred an additional 12 hours, and concentrated in vacuo until the theoretical mass of the acid chloride was obtained. The residue was suspended intetrahydrofuran (7.5 mL), and methanol (0.19 mL, 4.59 mmol), followed by triethylamine (0.64 mL, 4.59 mmol) was added. The mixture was heated to reflux for 14 hours, concentrated, and the resulting residue partitioned between methylene chloride (150 mL) and 1M aqueous hydrochloric acid (50 mL). The aqueous layer was back extracted with additional portions of methylene chloride (2×30 mL), the combined extracts dried over magnesium sulfate, and concentrated to afford crude 4-[4-(4-chlorophenoxy)phenylthiomethyl]-tetrahydropyran-4-carboxylic acid methyl ester, which was taken directly into the next reaction without further purification. $^1$HNMR (CDCl$_3$) δ 1.62. (m, 2H), 2.15 (dm, J=13.6 Hz, 2H), 3.13 (s, 2H), 3.47 (td, J=11.9, 2.4 Hz, 2H), 3.59 (s, 3H), 3.81 (dt, J=12.0, 4.1 Hz, 2H), 6.92 (d, J=8.9 Hz, 2H), 7.29 (d, J=8.8 Hz, 2H), 7.36 (d, J=8.8 Hz, 2H).

7J. Preparation of Ia where R$^1$ and R$^2$ taken together with the Carbon to which they are attached represent Tetrahydropyran, R$^3$ and R$^4$ are Hydrogen, R$^5$ is 4-(4-Chlorophenoxy)phenyl, and R is Ethyl, from a Compound of Formula (13)

4-(Iodomethyl)tetrahydropyran-4-carboxylic acid ethyl ester (300 mg, 1 mmol) was added to a solution containing the sodium salt of 4-(4-chlorophenoxy)thiophenol (generated by the addition of sodium hydride powder (36 mg, 1.5 mmol) to a solution of 4-(4-chlorophenoxy) thiophenol (262 mg, 1.1 mmol) in N,N-dimethylformamide (2 mL) at 0° C. and stirring for 30 minutes). The mixture was warmed to room temperature over 5 minutes, stirred for an additional 20 minutes, cooled to room temperature, and 1M aqueous hydrochloric acid (5 mL) added. The mixture was then partitioned between ethyl acetate (100 mL) and 2M hydrochloric acid (25 mL). The aqueous layer was separated and washed with additional ethyl acetate (2×50 mL). The organic extracts were combined, washed with 1M sodium hydroxide (2×30 mL), dried over magnesium sulfate, concentrated in vacuo. Chromatography over silica gel, and eluting with 20% ethylacetate/hexanes, yielded pure 4-[4-(4-chlorophenoxy)phenylthiomethyl]-tetrahydropyran-4-carboxylic acid ethyl ester (370 mg, 91%), followed by impure 4-[4-(4-chlorophenoxy)phenylthiomethyl] tetrahydropyran-4-carboxylic acid ethyl ester (40 mg). IR (KBr) 1728 cm$^{-1}$; $^1$HNMR (CDCl$_3$) 1.23 (q, J=7.1 Hz, 3H), 1.56 (ddd, J=14.6, 10.9, 4.4, 2H), 1.63 (ddd, J=14.6, 5.7, 3.3, 2H), 3.13 (s, 2H), 3.51 (ddd, J=11.8, 11.1, 2.4 Hz, 2H), 3.80 (dt, J=11.8, 4.1 Hz, 2H), 4,07 (q, J=7.1 Hz, 2H), 6.91 (d, J=8.9 Hz, 2H), 6.92 (d, J=8.9 Hz, 2H), 7.29 (d, J=9.0 Hz, 2H), 7.39 (d, J=8.9 Hz, 2H); $^{13}$C NMR (CDCl$_3$) δ 14.20 (q), 33.72 (t), 45.72 (t), 46.07 (s), 60.92 (t), 65.06 (t), 119.29 (d), 120.20 (d), 128.43 (s), 129.85 (d), 130.57 (s), 133.05 (s), 155.40 (s), 156.21 (s), 174.02 (s); EIHRMS Calcd. for C$_{21}$H$_{23}$SO$_4$Cl (M$^+$): 406.1006. Found: 406.1008. Anal. Calcd. for C$_{21}$H$_{23}$SO$_4$Cl: C, 61.98; H, 5.70. Found: C, 61.86; H, 5.68.

7K. Preparation of Ia where R$^1$ and R$^2$ when taken together with the Carbon to which they are attached represent Tetrahydropyran, R$^3$ and R$^4$ are Hydrogen, R$^5$ is 4-(4-Bromophenoxy)phenyl, and R is Ethyl, from a Compound of Formula (13)

Similarly, replacing 4-(4-chlorophenoxy)thiophenol with 4-(4-bromophenoxy)thiophenol, and following the procedures of Example 7J above, 4-[4-(4-bromophenoxy) phenylthiomethyl]tetrahydropyran-4-carboxylic acid ethyl ester was prepared (2.10 g, 93%). IR (KBr) 1728 cm$^{-1}$; $^1$HNMR (CDCl$_3$) δ 1.22 (q, J=7.1 Hz, 3H), 1.60 (ddd, J=14.6, 10.9, 4.5, 2H), 2.14 (ddd, J=14.6, 5.7, 3.3, 2H), 3.13 (s, 2H), 3.81 (ddd, J=11.8, 11.1, 2.4 Hz, 2H), 4.07 (q, J=7.1 Hz, 2H), 6.87 (d, J=9.0 Hz, 2H), 6.92 (d, J=8.8 Hz, 2H), 7.37 (d, J=8.8 Hz, 2H), 7.43 (d, J=9.0 Hz, 2H); $^{13}$CNMR (CDCl$_3$) δ 14.20 (q), 33.71 (t), 45.69 (t), 46.05 (s), 60.92 (t), 65.05 (t), 116.06 (s), 119.40 (d), 120.59 (d), 130.69 (s), 132.81 (d), 133.03 (s), 156.04 (s), 156.16 (s), 174.01 (s); EIHRMS Calcd. for C$_{21}$H$_{23}$SO$_4$Br (M$^+$): 450.0500. Found: 450.0505. Anal. Calcd. for C$_{21}$H$_{23}$SO$_4$Cl: C, 55.88; H, 5.14. Found: C, 55.52; H, 5.09.

Similar reactions were carried out, starting from compounds of Formula (13) where X is iodo, bromo, and chloro, and moderate to good yields were obtained in all cases.

7L. Preparation of Ia, varying R$^1$, R$^2$, R$^3$, R$^4$, and R$^5$

Similarly, optionally replacing 4-carboxymethylene-N-CBZ-piperidine with other N-protected compounds of Formula (4) and following the procedures of Example 7A (1) and (2) above, or optionally replacing cyclopentylideneacetic acid with other compounds of Formula (4) and following the procedures of Example 7B above, and optionally replacing p-phenoxythiophenol with other compounds of Formula (5), the following compounds of Formula Ia were prepared:

2-[4-(4-methoxyphenylthio)-N-CBZ-piperidin-4-yl-]-acetic acid;

2-[4-(4-methoxyphenylthio)-piperidin-4-yl)]-acetic acid;

2-benzyl-3-(3-methoxyphenylthio)-propionic acid;

2-benzyl-3-(4-methoxyphenylthio)-propionic acid;

3-benzyl-3-(4-methoxyphenylthio)-propionic acid;

3,3-dimethyl-3-[(4-chlorophenoxy)phenylthio]-propionic acid;

2-{4-[4-(4-fluorophenoxy)phenylthio]-piperidin-4-yl}-acetic acid;

2-{4-[4-(4-fluorophenoxy)phenylthio]-N-CBZ-piperidin-4-yl}-acetic acid;

3-benzyl-3-[(4-phenylthiophenyl)thio]-propionic acid;

3-benzyl-3-(phenylthio)-propionic acid;

3-benzyl-3-(4-phenoxphenylthio)-propionic acid;

3-benzyl-3-[(4-biphenyl)thio]-propionic acid;

3-benzyl-3-(2-naphthylthio)-propionic acid;

3-benzyl-3-(4-methoxystyrylphenylthio)-propionic acid;

3-cyclopentylmethyl-3-(4-methoxyphenylthio)-propionic acid;

3-cyclopentylmethyl-2-isopropyl-3-(4-methoxyphenylthio)-propionic acid;

3-ethyl-2-methyl-3-(4-methoxyphenylthio)-propionic acid;

3,3-dimethyl-(4-methoxyphenylthio)-propionic acid;

2-[1-(4-methoxyphenylthio)-cyclopent-1-yl]-acetic acid;

2-[4-(4-methoxyphenylthio)-cyclohexanone-4-yl]-acetic acid ethylene ketal;

2-[1-(4-methoxyphenylthio)-(4-methylcyclohex-1-yl]-acetic acid;

2-[1-(4-phenoxyphenylthio)-cyclohex-1-yl]-acetic acid;

2-[4-(4-phenoxyphenylthio)-tetrahydropyran-4-yl]-acetic acid;

{4-[4-(4-benzo[b]thiophen-2-yl-phenoxy)phenylthio)-tetrahydropyran-4-yl]-acetic acid;

2-{4-[4-(phenylmethyl)phenylthio]-tetrahydropyran-4-yl}-acetic acid;

2-{4-[4-(4-fluorophenoxy)phenylthio]-tetrahydropyran-4-yl}-acetic acid;

2-{4-[4-(4-chlorophenoxy)phenylthio]-tetrahydropyran-4-yl}-acetic acid: mp 138.5–138.8° C.; $^1$HNMR (CDCl$_3$, OH not seen) 6 1.73 (d, J=14.7, 2H), 1.91 (ddd, J=14.7, 10.1, 4.3 Hz, 2H), 2.58 (s, 2H), 3.76 (dt, J=11.8, 4.1 Hz, 2H), 4.02 (dt, J=11.8, 2.6 Hz, 2H), 6.94 (d, J=8.8 Hz, 2H), 6.98 (d, J=8.9 Hz, 2H), 7.33 (d, J=8.9 Hz, 2H), 7.53 (d, J=8.8 Hz, 4H); FABMS (M$^+$): 379.2. Anal. Calcd. for C$_{19}$H$_{19}$SO$_4$Cl: C, 60.23; H, 5.05. Found: C, 60.39; H, 5.01;

2-{4-[4-(4-chlorophenoxy)phenylthiol-tetrahydropyran-4-yl}-acetic acid;

2-{4-[4-(4-bromophenoxy)phenylthiol-tetrahydropyran-4-yl}-acetic acid;

2-[4-(4-phenoxyphenylthio)-tetrahydrothiopyran-1,1-dioxide-4-yl]-acetic acid;

trans-2-(4-methoxyphenylthio)-cyclopentanecarboxylic acid; and 2-(4-methoxyphenylthio)-cyclohexanecarboxylic acid.

7M. Preparation of Ia, varying R$^1$, R$^2$, R$^3$, R$^4$, and R$^5$

Similarly, optionally replacing 2,7-dioxa-spiro[3.5] nonane-1-one with other compounds of Formula (10) and following the procedures of Example 7D above, and optionally replacing 4-(4-chlorophenoxy)thiophenol with other compounds of Formula (5), the following compounds of Formula Ia were prepared:

4-[4-(4-fluorophenoxy)phenylthiomethyl] tetrahydropyran-4-carboxylic acid;

4-[4-(4-bromophenoxy)phenylthiomethyl] tetrahydropyran-4-carboxylic acid;

3-(4-benzoylphenylthio)-2,2-dimethyl propionic acid;

3-[4-(4-chlorophenoxy)phenylthio]-2,2-dimethyl propionic acid;

4-[(4-phenoxypyrid-4-yl)thiomethyl]tetrahydropyran-4-carboxylic acid: $^1$HNMR (OH not observed; CDCl$_3$) δ 1.65 (m$_c$, 2H), 2.16 (dm, J=14.2 Hz, 2H), 3.20 (s, 2H), 3.57 (tm, J=11.4 Hz, 2H), 3.84 (dm, J=12.0 Hz, 2H), 6.87 (d, J=6.2 Hz, 2H), 7.00 (d, J=8.6 Hz, 2H), 7.47 (d, J=8.9 Hz, 2H), 8.43 (d, J=6.0 Hz, 2H).

7N. Preparation of Ia, varying R$^1$, R$^2$, R$^3$, R$^4$, and R$^5$

Similarly, following the procedures of Example 7 above, other compounds of Formula Ia are prepared.

Example 8

Preparation of Compounds of Formula Iba

8A. Preparation of Iba where R$^1$ and R$^2$ when taken together with the Carbon to which they are attached represent Tetrahydropyran, R$^3$ and R$^4$ are Hydrogen, and R$^5$ is 4-(4-Chlorophenoxy)phenyl Oxalyl chloride (37.5 mL, 429.5 mmol) was added dropwise over 10 minutes to a suspension of 4-[4-(4-chlorophenoxy)phenylthiomethyl]-tetrahydropyran-4-carboxylic acid (65.1 g, 171.8 mmol) and N,N-dimethylformamide catalyst (2 mL) in methylene chloride (1 liter) at 0° C. The mixture was warmed to room temperature over 1 hour and the resultant partial slurry stirred an additional 20 hours, concentrated under reduced pressure until the theoretical mass of the acid chloride was obtained. This mixture was dissolved in methylene chloride (600 mL), cooled to 0° C., and N,O-bis(trimethylsilyl)hydroxylamine (109.1 mL, 510.45 mmol) added dropwise over 10 minutes. The mixture was immediately warmed to room temperature, stirred 3 hours, and recooled to 0° C. Aqueous 2.4M hydrochloric acid solution (400 mL, 960 mmol) was added to the solution, causing precipitation of the hydroxamic acid product within several minutes after the addition. The slurry was stirred an additional 30 minutes and filtered. The filter cake was washed with water (3×30 mL) and 50% diethyl ether-hexanes (2×25 mL) and dried at 70° C. to afford 4-[4-(4-chlorophenoxy)phenylthiomethyl]-tetrahydropyran-4-(N-hydroxycarboxamide) (61.8 g, 92%). mp 146.6–148.0° C.; IR (KBr) 3426 (br), 1636 cm$^{-1}$; $^1$HNMR (DMSO-d$_6$) δ 1.54 (ddd, J=13.8, 10.2, 4.0 Hz, 2H), 2.00 (dm, J=13.8 Hz, 2H), 3.16 (s, 2H), 3.39 (m, 2H), 3.66 (dt, J=11.7, 3.8 Hz, 2H), 6.98 (d, J=8.8 Hz, 2H), 7.02 (d, J=9.0 Hz, 2H), 7.40 (d, J=8.8 Hz, 2H), 7.41 (d, J=8.9 Hz, 2H), 8.78 (s, 1H), 10.63 (s, 1H); $^{13}$CNMR (CDCl$_3$) δ 32.79 (t), 43.60 (s), 43.70 (t), 63.93 (t), 119.56 (d), 120.07 (d), 127.19 (s), 129.85 (d), 131.24 (d), 131.34 (s), 154.62 (s), 155.59 (s), 169.69 (s); FABHRMS Calcd. for C$_{19}$H$_{21}$NSO$_4$Cl (M$^+$+H): 394.0880. Found: 378.0872. Anal. Calcd. for C$_{19}$H$_{20}$NSO$_4$Cl: C, 57.94; H, 5.12; N, 3.56. Found: C, 57.98; H, 5.04; N, 3.68.

8B. Alternative Preparation of Iba where R$^1$ and R$^2$ when taken together with the Carbon to which they are attached represent Tetrahydropyran, R$^3$ and R$^4$ are Hydrogen, and R$^5$ is 4-(4-Chlorophenoxy)phenyl Oxalyl chloride (37.5 mL, 429.5 mmol) was added dropwise over 10 minutes to a solution of 4-[4-(4-chlorophenoxy)phenylthiomethyl]-tetrahydropyran-4-carboxylic acid (65.1 g, 171.8 mmol) and N,N-dimethylformamide catalyst (2 mL) in methylene chloride (1 liter) at 0° C. The mixture was warmed to room temperature over 1 hour, and the resultant partial slurry stirred an additional 20 hours and concentrated in vacuo until the theoretical mass of the acid chloride was obtained. A solution of the acid chloride mixture (650 mg, 1.68 mmol) in methylene chloride (3.4 mL) was added dropwise over 2 minutes to a solution of 50% aqueous hydroxylamine (556 mg) in 2:1 tetrahydrofuran/tert-butanol (5.1 mL). The mixture was stirred 1.5 hours and concentrated until approximately 1 mL of aqueous solution was remaining. The slurry was filtered, washed with 1:1 diethyl ether-hexanes (3×15 mL) and the solid dried overnite at 70° C. in a vacuum oven, to afford 4-[4-(4-chlorophenoxy)phenylthiomethyl]-tetrahydropyran-4-(N-hydroxycarboxamide) (584 mg, 91%). mp 146.6–148.0° C.; IR (K3r) 3426 (br), 1636 cm$^{-1}$; $^1$HNMR (DMSO-d$_6$) δ 1.54 (ddd, J=13.8, 10.2, 4.0 Hz, 2H), 2.00 (dm, J=13.8 Hz, 2H), 3.16 (s, 2H), 3.39 (m, 2H), 3.66 (dt, J=11.7, 3.8 Hz, 2H), 6.98 (d, J=8.8 Hz, 2H), 7.02 (d, J=9.0 Hz, 2H), 7.40 (d, J=8.8 Hz, 2H), 7.41 (d, J=8.9 Hz, 2H), 8.78 (s, 1H), 10.63 (s, 1H); $^{13}$C NMR (CDCl$_3$) δ 32.79 (t), 43.60 (s), 43.70 (t), 63.93 (t), 119.56 (d), 120.07 (d), 127.19 (s), 129.85 (d), 131.24 (d), 131.34 (s), 154.62 (s), 155.59 (s), 169.69 (s); FABHRMS Calcd. for C$_{19}$H$_{21}$NSO$_4$Cl (M$^+$+H): 394.0880. Found: 378.0872. Anal. Calcd. for C$_{19}$H$_{20}$NSO$_4$Cl: C, 57.94; H, 5.12; N, 3.56. Found: C, 57.98; H, 5.04; N, 3.68.

8C. Preparation of Iba, varying R$^1$, R$^2$, R$^3$, R$^4$, and R$^5$

Similarly, replacing 4-[4-(4-chlorophenoxy) phenylthiomethyl]tetrahydropyran-4-carboxylic acid with other compounds of Formula Ia and following the procedures of Example 8A above, the following compounds of Formula Iba were prepared:

4-[4-(4-fluorophenoxy)phenylthiomethyl] tetrahydropyran-4-(N-hydroxycarboxamide): mp 146.2–146.5° C.; IR (KBr) 3431 (br), 1628 cm$^{-1}$; $^1$HNMR (CDCl$_3$; NH and OH not observed) δ 1.35 (ddd, J=13.8, 10.2, 4.0 Hz, 2H), 1.83 (dm, J=13.8 Hz, 2H), 2.85 (s, 2H), 3.23 (m, 2H), 3.46 (dt, J=11.9, 3.9 Hz, 2H), 6.58 (d, J=8.8 Hz, 2H), 6.57 (d, J=8.8 Hz, 2H), 6.65–6.78 (m, 4H), 7.06 (d, J=8.8 Hz, 2H); $^{13}$C NMR (CDCl$_3$) δ 32.99 (t), 44.27 (s), 45.49 (t), 64.63 (t), 116.28 (dd, J$_{C-F}$=23.2 Hz), 118.64 (d), 120.49 (dd, J$_{C-F}$=8.5 Hz), 130.41 (s), 132.49 (d), 152.46 (s), 156.49 (s), 160.29 (d, J$_{C-F}$=241.9 Hz), 170.23 (s); FABMS (M$^+$+H): 378. Anal. Calcd. for C$_{19}$H$_{20}$NSO$_4$F: C, 60.46; H, 5.34; N, 3.71. Found: C, 60.08; H, 5.29; N, 3.65.

4-[4-(4-bromophenoxy)phenylthiomethyl] tetrahydropyran-4-N-hydroxycarboxamide: mp 153.1–154.0° C.; IR (KBr) 3434 (br), 1634 cm$^{-1}$; 1HNMR (CDCl$_3$; NH and OH not observed) δ 1.68 (ddd, J=14.0, 10.0, 4.0 Hz, 2H), 2.13 (dm, J=14.0 Hz, 2H), 3.15 (s, 2H), 3.55 (ddd, J=12.0, 10.2, 2.5 Hz, 2H), 3.76 (dt, J=12.0 Hz, 4.1 Hz, 2H), 6.87 (d, J=9.0 Hz, 2H), 6.90 (d, J=8.8 Hz, 2H), 7.37 (d, J=8.8 Hz, 2H), 7.43 (d, J=9.0 Hz, 2H); $^{13}$CNMR (CDCl$_3$) δ 33.01 (t), 44.32 (s), 45.40 (t), 64.65 (t), 115.95 (s), 119.50 (d), 120.53 (d), 130.67 (s), 132.76 (d), 132.80 (d), 155.92 (s), 156.16 (s), 170.60 (s); FABMS (M$^+$+H): 438. Anal. Calcd. for C$_{19}$H$_{20}$NSO$_4$Br: C, 52.06; H, 4.60; N, 3.20. Found: C, 51.84; H, 4.52; N, 3.54.

3-(4-benzoylphenylthio)-2,2-dimethyl-N-hydroxypropionamide;

3-[4-(4-chlorophenoxy)phenylthio]-2,2-dimethyl-N-hydroxypropionamide: mp 114.7–115.3° C.; $^1$HNMR (CDCl$_3$) δ 1.30 (s, 6H), 3.14 (s, 2H), 6.90 (d, J=8.8 Hz, 2H), 6.92 (d, J=8.8 Hz, 2H), 7.29 (d, J=8.9 Hz, 2H), 7.37 (d, J=8.8 Hz, 1H); FABHRMS Calcd. for C$_{17}$H$_{18}$NSO$_3$Cl (M$^+$+H): 352.0772. Found: 352.0774. Anal. Calcd. for C$_{17}$H$_{18}$NSO$_3$Cl: C, 58.03; H, 5.16; N, 3.98. Found: C, 57.85; H, 5.10; N, 4.12.

3,3-dimethyl-3-[(4-chlorophenoxy)phenylthio]-N-hydroxypropionamide;

{4-[4-(4-benzo[b]thiophen-2-yl-phenoxy)phenylthio)-tetrahydropyran-4-yl]-N-hydroxyacetamide;

2-{4-[4-(phenylmethyl)phenylthio]-tetrahydropyran-4-yl}-N-hydroxyacetamide;

2-{4-[4-(4-chlorophenoxy)phenylthio]-tetrahydropyran-4-yl}-N-hydroxyacetamide; and 2-{4-[4-(4-bromophenoxy)phenylthiol-tetrahydropyran-4-yl}-N-hydroxyacetamide.

8D. Preparation of Iba, varying $R^1$, $R^2$, $R^3$, $R^4$, and $R^5$

Similarly, replacing 4-[4-(4-chlorophenoxy)phenylthiomethyl]tetrahydropyran-4-carboxylic acid with other compounds of Formula Ia and following the procedures of Example 8A above, other compounds of Formula Iba are prepared, for example:

4-(4-phenoxyphenylthiomethyl)tetrahydropyran-4-(N-hydroxycarboxamide);

4-[4-(4-fluorophenoxy)phenylthiomethyl]tetrahydropyran-4-(N-hydroxycarboxamide);

4-[4-(4-chlorophenoxy)phenylthiomethyl]piperidine-4-(N-hydroxycarboxamide);

4-[4-(4-chlorophenoxy)phenylthiomethyl]-1-methylpiperidine-4-(N-hydroxycarboxamide);

4-[4-(4-chlorophenoxy)phenylthiomethyl]-1-(cyclopropylmethyl)piperidine-4-(N-hydroxycarboxamide);

4-[4-(4-chlorophenoxy)phenylthiomethyl]-1-acetylpiperidine-4-(N-hydroxycarboxamide);

4-[4-(4-chlorophenoxy)phenylthiomethyl]-1-(3-pyridyl)piperidine-4-(N-hydroxycarboxamide);

4-[4-(4-chlorophenoxy)phenylthiomethyl]-1-(3-pyridoyl)piperidine-4-(N-hydroxycarboxamide);

2-[4-(4-methoxyphenylthio)-N-CBZ-piperidin-4-yl-]-N-hydroxyacetamide;

2-[4-(4-methoxyphenylthio)-piperidin-4-yl)]-N-hydroxyacetamide;

2-benzyl-3-(3-methoxyphenylthio)-N-hydroxypropionamide;

2-benzyl-3-(4-methoxyphenylthio)-N-hydroxypropionamide;

3-benzyl-3-(4-methoxyphenylthio)-N-hydroxypropionamide;

2-{4-[4-(4-fluorophenoxy)phenylthiol-piperidin-4-yl}-N-hydroxyacetamide;

2-{4-[4-(4-fluorophenoxy)phenylthio]-N-CBZ-piperidin-4-yl}-N-hydroxyacetamide;

3-benzyl-3-[(4-phenylthiophenyl)thio]-N-hydroxypropion- amide;

3-benzyl-3-(phenylthio)-N-hydroxypropionamide;

3-benzyl-3-(4-phenoxphenylthio)-N-hydroxypropionamide;

3-benzyl-3-[(4-biphenyl)thiol-N-hydroxypropionamide;

3-benzyl-3-(2-naphthylthio)-N-hydroxypropionamide;

3-benzyl-3-(4-methoxystyrylphenylthio)-N-hydroxypropionamide;

3-cyclopentylmethyl-3-(4-methoxyphenylthio)-N-hydroxypropionamide;

3-cyclopentylmethyl-2-isopropyl-3-(4-methoxyphenylthio)-N-hydroxypropionamide;

3-ethyl-2-methyl-3-(4-methoxyphenylthio)-N-hydroxypropionamide;

3,3-dimethyl-(4-methoxyphenylthio)-N-hydroxypropionamide;

2-[1-(4-methoxyphenylthio)-cyclopent-1-yl]-N-hydroxyacetamide;

2-[4-(4-methoxyphenylthio)-cyclohexanone-4-yl]-N-hydroxyacetamide ethylene ketal;

2-[1-(4-methoxyphenylthio)-(4-methylcyclohex-1-yl]-N-hydroxyacetamide;

2-[1-(4-phenoxyphenylthio)-cyclohex-1-yl]-N-hydroxyacetamide;

2-[4-(4-phenoxyphenylthio)-tetrahydropyran-4-yl]-N-hydroxyacetamide;

2-{4-[4-(4-fluorophenoxy)phenylthiol-tetrahydropyran-4-yl}-N-hydroxyacetamide;

2-[4-(4-phenoxyphenylthio)-tetrahydrothiopyran-1,1-dioxide-4-yl]-N-hydroxyacetamide;

trans-2-(4-methoxyphenylthio)-cyclopentanecarboxylic acid; and 2-(4-methoxyphenylthio)-cyclohexanecarboxylic acid.

Example 9

Preparation of Compounds of Formula Ib

9A. Preparation of Ib where $R^1$ and $R^2$ are Hydrogen, $R^3$ and $R^4$ when taken together with the Carbon to which they are attached are Cyclopentyl, and $R^5$ is 4-Phenoxyphenyl The 2-[1-(4-phenoxyphenylthio)-cyclopent-1-yl]-acetic acid obtained in Example 5 was dissolved in methylene chloride (8 ml) and treated with 4-dimethylaminopyridine (180 mg), O-(tert-butyl) hydroxylamine hydrochloride (360 mg), triethylamine (540 µL), pyridine (400 µL), and 1-(3-dimethylaminopropyl)-3-ethylcarbodiimide hydrochloride (750 mg). After stirring overnight the reaction mixture was partitioned between ethyl acetate and water, the organic layer separated, and the solvent removed under reduced pressure. Preparative TLC of the residue and elution with 2:1 hexane/ethyl acetate gave N-(tert-butoxy)-2-[1-(4-phenoxyphenylthio)cyclopent-1-yl]-acetamide (270 mg) as a white foam, which can be used in the next reaction without further purification.

9B. Preparation of Ib where $R^1$ and $R^2$ are Hydrogen, $R^3$ and $R^4$ when taken together with the Carbon to which they are attached are Tetrahydropyran, and $R^5$ is 4-Phenoxyphenyl O-(tert-Butyl)hydroxylamine hydrochloride (9.57 g), 4-methylmorpholine (15.64 ml), hydroxybenzotriazole (6.87 g), and 1-(3-dimethylaminopropyl)-3-ethylcarbodiimide hydrochloride (19.5 g) was added to a solution of 2-[4-(4-phenoxyphenylthio)-tetrahydropyran-4-yl]acetic acid (17.5 g) in methylene chloride (200 ml). After stirring for 3 hours at room temperature, 0.5 M hydrochloric acid (200 ml) was added to the mixture, and the mixture extracted with methylene chloride. The solvent was removed from the combined extracts under reduced pressure. Silica gel chromatography of the residue and elution with 35%–80% ethyl acetate/hexane gave N-tert-butoxy-2-[4-(4-phenoxyphenylthio)-tetrahydropyran-4-yl]-acetamide (15.3 g) as an oil, which can be used in the next reaction without further purification.

9C. Preparation of Ib where $R^3$ and $R^4$ are Hydrogen, $R^1$ and $R^2$ when taken together with the Carbon to which they are attached are N-BOC-Piperidine, and $R^5$ is 4-(4-Chlorophenoxy)phenyl 4-Methylmorpholine (2.60 mL, 23.68 mmol) was added dropwise to a solution of 2-{4-[4-(4-chlorophenoxy)phenylthiomethyl]-N-BOC-piperidin-4-yl}-carboxylic acid obtained in Example 6 (2.83 g, 5.92 mmol), O-(tert-butyl) hydroxylamine hydrochloride (2.23 g, 17.76 mmol), and 1-(3-dimethylaminopropyl)-3-ethylcarbodiimide hydrochloride (2.27 g, 11.84 mmol) in anhydrous methylene chloride (25 ml) cooled to 0° C. After the resulting mixture was allowed to warm to room temperature over 1 hour and stirred for an additional 12 hours, the mixture was partitioned between diethyl ether/1 N aqueous hydrochloric acid (300 mL). The acid layer was back extracted using diethyl ether (2×100 mL), and the combined ether extracts dried over magnesium sulfate and concentrated. Chromatography over silica gel, and eluting with 25% ethyl acetate/hexanes, gave N-(tert-butoxy)-2-{4-[4-(4-chlorophenoxy) phenylthiomethyl]-N-BOC-piperidin-4-yl}-carboxamide (2.88 g, 89%). $^1$HNMR (CDCl$_3$) δ 1.31 (s, 9H), 1.45 (s, 9H), 1.58 (m$_c$, 2H), 2.10 (br d, J=14.2 Hz, 2H), 3.13 (s, 2H), 3.19 (m$_c$, 2H), 3.73 (m$_c$, 2H), 6.93 (d, J=8.8 Hz, 2H), 6.95 (d, J=8.9 Hz, 2H), 7.30 (d, J=8.9 Hz, 2H), 7.38 (d, J=8.7 Hz, 2H), 8.15 (br s, 1H).

9D. Preparation of Ib, varying R$^1$, R$^2$, R$^3$, R$^4$, and R$^5$

Similarly, following the procedures of Example 9A above, but replacing 2-[1-(4-phenoxyphenylthio)-cyclopent-1-yl]-acetic acid with other compounds of Formula Ia, the following compounds of Formula Ib were prepared:

N-tert-butoxy-2-[4-(4-phenoxyphenylthio)-N-CBZ-piperidin-4-yl)]-acetamide;

N-tert-butoxy-2-[4-(4-methoxyphenylthio)-N-CBZ-piperidin-4-yl)]-acetamide;

N-tert-butoxy-2-{4-[4-(4-fluorophenoxy)phenylthio]-N-CBZ-piperidin-4-yl}-acetamide;

N-tert-butoxy-2-{4-[4-(4-fluorophenoxy)phenylthio]-piperidin-4-yl}-acetamide;

N-tert-butoxy-2-[4-(4-phenoxyphenylthio)-piperidin-4-yl)]-acetamide;

N-tert-butoxy-2-[4-(3-methoxyphenylthio)-piperidin-4-yl)]-acetamide;

N-tert-butoxy-2-[4-(4-methoxyphenylthio)-piperidin-4-yl)]-acetamide;

N-tert-butoxy-2-benzyl-3-(phenylthio)-propionamide;

N-tert-butoxy-3-benzyl-3-(phenylthio)-propionamide;

N-tert-butoxy-3-benzyl-3-(4-methoxyphenylthio)-propionamide;

N-tert-butoxy-3-benzyl-3-[(4-phenylthiophenyl)thiol-propionamide;

N-tert-butoxy-3-benzyl-3-(4-phenoxyphenylthio)-propionamide;

N-tert-butoxy-3-benzyl-3-[(4-biphenyl)thio]-propionamide;

N-tert-butoxy-3-benzyl-3-(2-naphthylthio)-propionamide;

N-tert-butoxy-3-benzyl-3-(4-methoxystyrylphenylthio)-propionamide;

N-tert-butoxy-3-cyclopentylmethyl-3-(4-methoxyphenylthio)-propionamide;

N-tert-butoxy-3-cyclopentylmethyl-2-isopropyl-3-(4-methoxyphenylthio)-propionamide;

N-tert-butoxy-3-ethyl-2-methyl-3-(4-methoxyphenylthio)-propionamide;

N-tert-butoxy-3,3-dimethyl-(4-methoxyphenylthio)-propionamide;

N-tert-butoxy-2-[1-(4-methoxyphenylthio)-cyclopent-1-yl]-acetamide;

N-tert-butoxy-2-[1-(4-methoxyphenylthio)-(4-methylcyclohex-1-yl]-acetamide;

N-tert-butoxy-2-[4-(4-phenoxyphenylthio)-cyclohexanone-4-yl]-acetamide ethylene ketal;

N-tert-butoxy-2-[1-(4-phenoxyphenylthio)-cyclohex-1-yl]-acetamide;

N-tert-butoxy-2-[4-(4-methoxyphenylthio)-N-CBZ-piperidin-4-yl)]-acetamide;

N-tert-butoxy-2-[4-(4-methoxyphenylthio)-piperidin-4-yl)]-acetamide

N-tert-butoxy-2-{4-[4-(4-fluorophenoxy)phenylthio]-tetrahydropyran-4-yl}-acetamide;

N-tert-butoxy-2-{4-[4-(4-chlorophenoxy)phenylthio]-tetrahydropyran-4-yl}-acetamide;

N-tert-butoxy-2-[4-(4-phenoxyphenylthio)-tetrahydrothiopyran-1,1-dioxide-4-yl]-acetamide;

N-tert-butoxy-4-[4-(4-pyridyloxy)phenylthiomethyl]-tetrahydropyran-carboxamide: $^1$HNMR (CDCl$_3$) δ 1.31 (s, 9H), 1.70 (m$_c$, 2H), 2.14 (dm, J=11.8 Hz, 2H), 3.21 (s, 2H), 3.63 (M., 2H), 3.82 (m$_c$, 2H), 6.84 (d, J=6.4 Hz, 2H), 7.03 (d, J=8.6 Hz, 2H), 7.44 (d, J=8.4 Hz, 2H), 8.20 (s, 1H), 8.48 (d, J=5.8 Hz, 2H).

N-tert-butoxy-4-[4-(5-chloro-2-pyridyloxy)phenylthiomethyl]-tetrahydropyran-carboxamide: mp 100.5–102.7° C.; IR (KBr) 3438 (br), 1657 cm$^{-1}$; $^1$HNMR (DMSO-d$_6$) 1.19 (s, 9H), 1.57 (ddd, J=13.5, 10.1, 4.0 Hz, 2H), 2.05 (dm, J=13.5 Hz, 2H), 3.34 (s, 2H), 3.42 (m., 2H), 3.65 (dm, J=11.6 Hz, 2H), 7.09 (d, J=8.8 Hz, 2H), 7.10 (d, J=8.8 Hz, 2H), 7.41 (d, J=8.7 Hz, 2H), 7.95 (dd, J=8.8, 2.7 Hz, 1H), 8.19 (d, J=2.7 Hz, 1H), 10.37 (s, 1H); $^{13}$CNMR (DMSO-d$_6$) δ 26.66 (q), 33.03 (t), 43.20 (t), 44.25 (s), 64.10 (t), 80.78 (s), 113.00 (d), 121.88 (d), 124.88 (s), 130.43 (d), 132.67 (s), 139.93 (d), 145.51 (d), 151.89 (s), 161.58 (s), 171.64 (s); FABHRMS Calcd. for C$_{22}$H$_{28}$N$_2$SO$_4$Cl (M$^+$+H): 451.1458. Found: 451.1461. Anal. Calcd. for C$_{22}$H$_{27}$N$_2$SO$_4$Cl: C, 58.59; H, 6.03; N, 6.21. Found: C, 58.70; H, 6.05; N, 6.43.

N-tert-butoxy-3-[4-(5-chloro-2-pyridyloxy)phenylthio]-2,2-dimethyl-N-hydroxypropionamide: mp 90.8–91.9° C.; IR (KBr) 3438 (br), 1651 cm$^{-1}$; $^1$HNMR (DMSO-d$_6$) δ 1.18 (s, 9H), 1.21 (s, 6H), 3.20 (s, 2H), 7.08 (m., 3H), 7.40 (d, J=8.7 Hz, 2H), 7.93 (dd, J=8.7, 2.7 Hz, 1H), 8.17 (d, J=2.7 Hz, 1H), 10.17 (s, 1H); $^{13}$C NMR (DMSO-d$_6$) δ 24.67 (q), 26.48 (q), 42.54 (s), 44.31 (t), 80.62 (s), 112.95 (d), 121.79 (d), 125.28 (s), 130.32 (d), 133.31 (s), 139.86 (d), 145.48 (d), 151.77 (s), 161.58 (s), 173.77 (s); FABHRMS Calcd for C$_{20}$H$_{26}$N$_2$SO$_3$Cl (M$^+$+H): 409.1353. Found: 409.1354. Anal. Calcd. for C$_{20}$H$_{25}$N$_2$SO$_3$Cl: C, 58.74; H, 6.16; N, 6.85. Found: C, 58.91; H, 6.13; N, 7.07.

N-tert-butoxy-2-(4-methoxyphenylmercapto)-cyclohexanecarboxamide; and

N-tert-butoxy-trans-2-(4-methoxyphenylmercapto)-cyclopentanecarboxamide.

9E. Preparation of Ib, varying R$^2$, R$^3$, R$^4$, and R$^5$

Similarly, following the procedures of Example 9A above, but replacing 2-[1-(4-phenoxyphenylthio)-cyclopent-1-yl]-acetic acid with other compounds of Formula Ia, other compounds of Formula Ib are prepared.

Example 10

Preparation of Compounds of Formula Id

10A. Preparation of Id where n is 0, R$^1$ and R$^2$ are Hydrogen, R$^3$ and R$^4$ when taken together with the Carbon to which they are attached are Cyclopentyl, and R$^5$ is 4-Phenoxyphenyl The N-tert-butoxy-2-[1-(4-phenoxyphenylthio)-cyclopent-1-yl]-acetamide was dissolved in trifluoroacetic acid (6 ml) and allowed to stand for 24 hours. The acid was evaporated off under reduced pressure and the product purified by preparative TLC, eluting with 6.5% methanol/methylene chloride gave N-hydroxy-2-[1-(4-phenoxyphenylthio)-cyclopent-1-yl]-acetamide (100 mg).

10B. Preparation of Id where n is 0, varying R$^1$, R$^2$, R$^3$, R$^4$, and R$^5$ Similarly, following the procedures of Example 10A above, but replacing N-tert-butoxy-2-[1-(4-phenoxyphenylthio)-cyclopent-1-yl]-acetamide with other compounds of Formula Ib, the following compounds of Formula Id where n is 0 are prepared:

N-hydroxy-2-(4-(4-phenoxyphenylthio)-N-CBZ-piperidin-4-yl)]-acetamide;

N-hydroxy-2-[4-(4-methoxyphenylthio)-N-CBZ-piperidin-4-yl)]-acetamide;

2-{4-[4-(4-fluorophenoxy)phenylthio]-N-CBZ-piperidin-4-yl}-N-hydroxy-acetamide;

2-{4-[4-(4-fluorophenoxy)phenylthio]-piperidin-4-yl}-N-hydroxy-acetamide;

3-benzyl-N-hydroxy-3-(3-methoxyphenylthio)-propionamide;

N-hydroxy-2-[4-(4-phenoxyphenylthio)-piperidin-4-yl)]-acetamide;

N-hydroxy-2-[4-(4-methoxyphenylthio)-piperidin-4-yl)]-acetamide;

2-benzyl-N-hydroxy-3-(phenylthio)-propionamide;

3-benzyl-N-hydroxy-3-(phenylthio)-propionamide;

3-benzyl-N-hydroxy-3-(4-methoxyphenylthio)-propionamide;

3-benzyl-N-hydroxy-3-[(4-phenylthiophenyl)thio]-propionamide;

3-benzyl-N-hydroxy-3-[(4-phenoxyphenylthio)-propionamide;

3-benzyl-N-hydroxy-3-[(4-biphenyl)p thio-propionamide;

3-benzyl-N-hydroxy-3-[(2-naphthylthio)-propionamide;

3-benzyl-N-hydroxy-3-(4-methoxystyrylphenylthio)-propionamide;

3-cyclopentylmethyl-N-hydroxy-3-(4-methoxyphenylthio)-propionamide;

3-cyclopentylmethyl-N-hydroxy-2-isopropyl-3-(4-methoxyphenylthio)-propionamide;

3-ethyl-N-hydroxy-2-methyl-3-(4-methoxyphenylthio)-propionamide;

3,3-dimethyl-N-hydroxy-(4-methoxyphenylthio)-propionamide;

N-hydroxy-2-[1-(4-methoxyphenylthio)-cyclopent-1-yl]-acetamide;

N-hydroxy-2-[1-(4-methoxyphenylthio)-(4-methylcyclohex-1-yl]-acetamide;

N-hydroxy-2-[1-(4-phenoxyphenylthio)-cyclohex-1-yl]-acetamide;

N-hydroxy-2-[4-(4-methoxyphenylthio)-N-CBZ-piperidin-4-yl]-acetamide;

N-hydroxy-2-[4-(4-methoxyphenylthio)-piperidin-4-yl)]-acetamide;

N-hydroxy-2-[4-(4-phenoxyphenylthio)-tetrahydropyran-4-yl]-acetamide;

2-{4-[4-(4-chlorophenoxy)-phenylthio]-tetrahydropyran-4-yl}-N-hydroxy-acetamide;

2-{4-[4-(4-fluorophenoxy)phenylthio]-tetrahydropyran-4-yl}-N-hydroxy-acetamide, m.p. 50–55° C.; and N-hydroxy-2-[4-(4-phenoxyphenylthio)-tetrahydrothiopyran-1,1-dioxide-4-yl]-acetamide.

10C. Preparation of Id where n is 0, varying $R^1$, $R^2$, $R^3$, $R^4$, and $R^5$ Similarly, following the procedures of Example 10A above, but replacing N-tert-butoxy-2-[1-(4-phenoxyphenylthio)-cyclopent-1-yl]-acetamide with other compounds of Formula Ib, other compounds of Formula Id where n is 0 are prepared.

Example 11

Preparation of Compounds of Formula Id

11A. Preparation of Id where n is 1, $R^1$ and $R^2$ are Hydrogen, $R^3$ and $R^4$ when taken together with the Carbon to which they are attached are Cyclopentyl, and $R^5$ is 4-Phenoxyphenyl A solution of N-hydroxy-2-[1-(4-phenoxyphenylthio)-cyclopent-1-yl]-acetamide (45 mg) in acetone (4 ml) was treated with sodium periodate (260 mg) in water (2 ml). Over the course of 24 hours, two additional portions of sodium periodate (260 mg) were added. After complete disappearance of starting material the solution was diluted with methylene chloride, filtered, dried, and the solvent evaporated under reduced pressure. Preparative TLC on silica gel and elution with 10% methanol/methylene chloride gave N-hydroxy-2-[1-(4-phenoxyphenylsulfinyl)-cyclopent-1-yl]-acetamide (15 mg), PMR (CDCl3) 7.64 (d,2H), 7.44 (t,2H), 7.30–7.05 (m,5H), 2.97 (d,1H), 2.53 (d,1H), 2.15–1.65 (m,8H).

11B. Preparation of Id where n is 1, $R^1$ and $R^2$ are Hydrogen, $R^3$ and $R^4$ when taken together with the Carbon to which they are attached are Tetrahydropyran-4-yl, and $R^5$ is 4-(4-Fluorophenoxy)phenyl 2-{4-[4-(4-Fluorophenoxy)phenylthio]-tetrahydropyran-4-yl}-N-hydroxyacetamide (500 mg) was dissolved in methanol (25 ml). OXONE (400 mg) in water (5 ml) was added. After stirring for 30 minutes, the mixture was partitioned between methylene chloride and water. Preparative TLC on silica gel and elution with 10% methanol/methylene chloride gave 2-{4-[4-(4-fluorophenoxy)phenylsulfinyl]-tetrahydropyran-4-yl}-N-hydroxyacetamide (402 mg, m.p. 120° C.).

11C. Preparation of Id where n is 1, varying $R^1$, $R^2$, $R^3$, $R^4$, and $R^5$ Similarly, following the procedures of Example 11A or 11B above, but replacing N-hydroxy-2-[1-(4-phenoxyphenylthio)-cyclopent-1-yl]-acetamide with other compounds of Formula Id where n is 0, other compounds of Formula Id where n is 1 are prepared, for example;

N-hydroxy-2-[4-(4-phenoxyphenylsulfinyl)-N-CBZ-piperidin-4-yl)]-acetamide;

N-hydroxy-2-[4-(4-phenoxyphenylsulfinyl)-piperidin-4-yl)]-acetamide;

N-hydroxy-2-[4-(4-methoxyphenylsulfinyl)-N-CBZ-piperidin-4-yl)]-acetamide;

2-{4-[4-(4-fluorophenoxy)phenylsulfinyl]-piperidin-4-yl}-N-hydroxyacetamide;

N-hydroxy-2-[4-(4-methoxyphenylsulfinyl)-piperidin-4-yl)]-acetamide;

2-benzyl-N-hydroxy-3-(4-methoxyphenylsulfinyl)-propionamide;

3-benzyl-N-hydroxy-3-(3-methoxyphenylsulfinyl)-propionamide;

3-benzyl-N-hydroxy-3-(4-methoxyphenylsulfinyl)-propionamide;

3-benzyl-N-hydroxy-3-[(4-phenylthiophenyl)sulfinyl]-propionamide;

3-benzyl-N-hydroxy-3-(4-phenoxyphenylsulfinyl)-propionamide;

3-benzyl-N-hydroxy-3-[(4-biphenyl)sulfinyl]-propionamide;

3-benzyl-N-hydroxy-3-(2-naphthylsulfinyl)-propionamide;

3-benzyl-N-hydroxy-3-(4-methoxystyrylphenylsulfinyl)-propionamide;

3-cyclopentylmethyl-N-hydroxy-3-(4-methoxyphenylsulfinyl)-propionamide;

3-cyclopentylmethyl-N-hydroxy-2-isopropyl-3-(4-methoxyphenylsulfinyl)-propionamide;

3-ethyl-N-hydroxy-2-methyl-3-(4-methoxyphenylsulfinyl)-propionamide;

3,3-dimethyl-N-hydroxy-(4-methoxyphenylsulfinyl)-propionamide;

N-hydroxy-2-[1-(4-methoxyphenylsulfinyl)-cyclopent-1-yl]-acetamide;

N-hydroxy-2-[1-(4-methoxyphenylsulfinyl)-(4-methylcyclohex-1-yl]-acetamide;

N-hydroxy-2-[1-(4-phenoxyphenylsulfinyl)-cyclohex-1-yl]-acetamide;

N-hydroxy-2-[4-(4-methoxyphenylsulfinyl)-N-CBZ-piperidin-4-yl)]-acetamide; and

N-hydroxy-2-[4-(4-methoxyphenylsulfinyl)-piperidin-4-yl)]-acetamide-N-hydroxy-2-[4-(4-phenoxyphenylsulfinyl)-tetrahydropyran-4-yl]-acetamide;

4-[4-(4-chlorophenoxy)phenylsulfinylmethyl]-tetrahydropyran-4-(N-hydroxycarboxamide): mp 141.3–142.1° C.; IR (KBr) 3436 (br), 1649 cm$^{-1}$; $^1$H NMR (DMSO-d$_6$) δ 1.67 (dm, J=13.9 Hz, 1H), 1.79 (dm, J=13.9 Hz, 1H), 40 1.97 (dm, J=13.9 Hz, 1H), 2.24 (dm, J=13.9 Hz, 1H), 2.97 (d, J=13.7 Hz, 1H), 3.07 (d, J=13.7 Hz, 1H), 3.33–3.54 (m,, 2H), 3.69 (m., 2H), 7.12 (d, J=8.9 Hz, 2H), 7.21 (d, J=8.8 Hz, 2H), 7.48 (d, J=8.9 Hz, 2H), 7.66 (d, J=8.8 Hz, 2H), 8.87 (br s, 1H), 10.76 (s, 1H), $^{13}$CNMR (DMSO-d$_6$) δ 32.43 (t), 33.71 (t), 42.69 (s), 63.65 (t), 67.12 (t), 118.90 (d), 121.07 (d), 126.11 (d), 128.19 (s), 130.07 (d), 139.51 (s), 154.62 (s), 158.72 (s), 169.68 (s); FABHRMS Calcd. for C$_{19}$H$_{21}$NSO$_5$Cl (M$^+$+H): 410.0829 Found: 426.0825. Anal. Calcd. for C$_{19}$H$_{20}$NSO$_5$Cl: C, 55.68; H, 4.92; N, 3.42. Found: C, 55.70; H, 4.93; N, 3.64.

2-{4-[4-(4-chlorophenoxy)-phenylsulfinyl]-tetrahydropyran-4-yl}-N-hydroxyacetamide; and N-hydroxy-2-[4-(4-phenoxyphenylsulfinyl)-tetrahydrothiopyran-1,1-dioxide-4-yl]-acetamide.

Example 12

Preparation of Compounds of Formula Id

12A. Preparation of Id where n is 2, R$^1$ and R$^2$ are Hydrogen, R$^3$ and R$^4$ when taken together with the Carbon to which they are attached are Cyclopentyl, and R$^5$ is 4-Phenoxyphenyl A solution of N-hydroxy-2-[1-(4-phenoxyphenylthio)-cyclopent-1-yl]-acetamide (45 mg) in methanol (4 ml) was treated with a solution of OXONE (260 mg) in water (2 ml). The mixture was stirred for 1 hour, then partitioned between methylene chloride and water. The organic layer was separated, and the solvent removed under reduced pressure. Preparative TLC on silica gel and elution with 10% methanol/methylene chloride gave N-hydroxy-2-[1-(4-phenoxyphenylsulfonyl)-cyclopent-1-yl]-acetamide (20 mg), m/e=393 (MNH$_4^+$, CIMS).

12B. Preparation of Id where n is 2, R$^1$ and R$^2$ when taken together with the Carbon to which they are attached represent Tetrahydropyran, R$^3$ and R$^4$ are Hydrogen, and R$^5$ is 4-(4-Chlorophenoxy)phenyl To a mechanically stirred suspension of 4-[4-(4-chlorophenoxy)-phenylthiomethyl]tetrahydropyran-4-(N-hydroxycarboxamide) (59.8 g, 151.8 mmol) in 20% tetrahydrofuran-methanol (1570 mL) cooled to 5° C. was added dropwise a solution of OXONE (152 g, 247 mmol) in water (1 liter), maintaining an internal temperature of 15–20° C. The mixture was stirred for 5.5 hours, and the mixture then partitioned between 30% ethyl acetate/water (3 liters). The aqueous layer was washed with ethyl acetate (2×300 mL), the combined ethyl acetate layers dried over magnesium sulfate, concentrated under reduced pressure, and the residue crystallized from the minimum amount of methylene chloride/hexanes, to afford analytically pure 4-[4-(4-chlorophenoxy)phenylsulfonylmethyl]-tetrahydropyran-4-(N-hydroxycarboxamide) as a white powder (54.2 g, 84%). mp 147.7–148.9° C.; IR (KBr) 3429 (br), 1636 cm$^{-1}$; $^1$HNMR (DMSO-d$_6$) δ 1.70 (dm, J=13.9, 2H), 1.96 (dm, J=13.9 Hz, 2H), 3.38–3.48 (m, 2H), 3.58–3.68 (m, 2H), 3.58–3.68 (m, 2H), 3.66 (s, 2H), 7.19 (d, J=8.9 Hz, 2H), 7.19 (d, J=8.9 Hz, 2H), 7.52 (d, J=8.9 Hz, 2H), 7.85 (d, J=8.9 Hz, 2H), 8.68 (d, J=2.0 Hz, 1H), 10.54 (d, J=2.0 Hz, 1H), $^{13}$CNMR (DMSO-d$_6$) δ 32.83 (t), 41.70 (s), 61.02 (t), 63.19 (t), 118.01 (d), 121.71 (d), 128.73 (s), 130.08 (d), 130.19 (d), 135.20 (s), 153.83 (s), 160.86 (s), 168.96 (s); FABHRMS Calcd. for C$_{19}$H$_{20}$NSO$_6$Cl: 426.0778. Found: 426.0774. Anal. Calcd. for C$_{19}$H$_{20}$NSO$_6$Cl: C, 53.59; H, 4.73; N, 3.29. Found: C, 53.58; H, 4.70; N, 3.40.

12C. Preparation of Id where n is 2, R$^1$ and R$^2$ when taken together with the Carbon to which they are attached represent Tetrahydropyran, R$^3$ is hydrogen, R$^4$ is Benzyl, and R$^5$ is 4-(4-Chlorophenoxy)phenyl To a solution of 3-benzyl-4-[4-(4-chlorophenoxy)-phenylsulfonylmethyl]-tetrahydropyran-4-carboxylic acid (316 mg, 0.63 mmol) and N,N-dimethylformamide catalyst (10 µL) in methylene chloride (6 mL) at 0° C. was added oxalyl chloride (200 µL, 2.20 mmol) dropwise over 10 minutes. The mixture was warmed to room temperature over 1 hour, the partial slurry stirred an additional 8 hours, and concentrated in vacuo until the theoretical mass of the acid chloride was obtained. This mixture was dissolved in methylene chloride (8 mL), cooled to 0° C., and a neat solution of N,O-bis(trimethylsilyl)hydroxylamine (0.56 g, 3.15 mmol) added dropwise over 5 minutes. The mixture was immediately warmed to room temperature, stirred for 48 hours, and recooled to 0° C. To this solution was added aqueous 1M hydrochloric acid (5 mL, 150 mmol), and the solution stirred for an additional 30 minutes, partitioned between ethyl acetae (150 mL) and brine (50 mL). The organic layer was dried over magnesium sulfate, concentrated in vacuo, chromatographed over silica gel, eluted with 4% methanol/methylene chloride) to afford 280 mg (86%) of 3-benzyl-4-[4-(4-chlorophenoxy)phenylsulfonylmethyl]-tetrahydropyran-4-(N-hydroxycarbamide) hydroxamic acid. mp 108–113° C.; IR (KBr) 3422 (br), 1653 cm$^{-1}$; $^1$HNMR (CDCl$_3$) δ 1.76–1.86 (m, 1H), 2.08–2.27 (m, 2H), 2.34 (dm, J=13.8 Hz, 1H), 2.91 (dd, J=16.5, 7.2 Hz, 1H), 3.17 (dd, J=16.4, 4.0 Hz, 1H), 3.19–3.23 (tm, J=9.0 Hz, 1H), 3.43 (td, J=11.9, 2.4 Hz, 2H), 6.65–6.72 (m, 2H), 6.76 (d, J=8.9 Hz, 2H), 6.88 (d, J=8.8 Hz, 2H), 6.98–7.04 (m, 3H), 7.30 (d, J=8.9 Hz, 2H), 7.49 (d, J=8.8 Hz, 2H); $^{13}$CNMR (CDCl$_3$) δ 31.76 (t), 34.23 (t), 47.30 (s), 64.07 (t), 64.66 (t), 72.68 (d), 117.50 (d), 121.64 (d), 126.47 (d), 127.96 (d), 128.53 (d), 130.31 (d), 130.69 (d), 132.91 (s), 137.83 (s), 153.34 (s), 162.12 (s), 171.30 (s); FABMS (M$^+$+H): 516; Anal. Calcd. for C$_{26}$H$_{26}$NSO$_6$Cl: C, 60.52; H, 5.08; N, 2.71. Found: C, 60.45; H, 5.10; N, 2.55.

12D. Preparation of Id where n is 2, varying R$^1$, R$^2$, R$^3$, R$^4$, and R$^5$ Similarly, following the procedures of Example 12C above, but replacing 4-[4-(4-chlorophenoxy)phenylthiomethyl]-tetrahydropyran-4-1(N-hydroxycarboxamide) with other compounds of Formula Iba, the following compounds of Formula Id where n is 2 were prepared:

4-[4-(4-fluorophenoxy)phenylsulfonylmethyl]tetrahydropyran-4-(N-hydroxycarboxamide): mp 153.1–153.9° C.; IR (KBr) 3434 (br), 1636 cm$^{-1}$; $^1$HNMR (CDCl$_3$) δ 1.87 (ddd, J=13.6, 8.8, 4.0 Hz, 2H), 2.22 (dm, J=13.6 Hz, 2H), 3.52–3.78 (m, 4H), 7.00–7.16 (m, 6H), 7.84 (d, J=8.9 Hz, 2H); $^1$CNMR (CDCl$_3$) δ 33.12 (t), 42.19 (s), 62.52 (t), 63.96 (t), 116.88 (dd, J$_{C-F}$=21.3 Hz), 117.30 (d), 121.97 (dd, J$_{C-F}$=8.4 Hz), 130.18 (s), 134.21 (d), 150.66 (d, J$_{C-F}$=2.6 Hz), 159.73 (d, J$_{C-F}$=243.8 Hz), 162.61 (s), 169.73 (s); FABMS (M$^+$+H): 410. Anal. Calcd for C$_{19}$H$_{20}$NSO$_6$F: C, 55.74; H, 4.92; N, 3.42. Found: C, 55.45; H, 4.91; N, 3.38.

4-[4-(4-bromophenoxy)phenylsulfonylmethyl] tetrahydropyran-4-(N-hydroxycarboxamide): mp 150.1–151.0° C.; IR (KBr) 3432 (br), 1636 cm$^{-1}$; $^1$HNMR (CDCl$_3$; NH and OH not observed) δ 1.87 (ddd, J=13.6, 8.7, 3.9 Hz, 2H), 2.12 (dm, J=13.6 Hz, 2H), 3.52 (s, 2H), 3.62–3.80 (m, 4H), 6.97 (d, J=8.8 Hz, 2H), 7.06 (d, J=8.8 Hz, 2H), 7.52 (d, J=8.8 Hz, 2H), 7.85 (d, J=8.8 Hz, 2H); $^{13}$CNMR (CDCl$_3$) δ 33.10 (t), 42.16 (s), 62.49 (t), 63.93 (t), 117.66 (s), 117.83 (d), 121.93 (d), 130.20 (d), 133.17 (d), 134.61 (s), 154.13 (s), 161.79 (s), 169.53 (s); FABHRMS Calcd. for C$_{19}$N$_{20}$NSO$_6$Br: (M$^+$+H): 470.0273. Found: 470.0268. Anal. Calcd. for C$_{19}$H$_{20}$NSO$_6$Br: C, 48.51; H, 4.28; N, 2.98. Found: C, 48.29; H, 4.02; N, 2.94.

3-(4-benzoylphenylsulfonyl)-2,2-dimethyl-N-hydroxypropionamide;

3-[4-(4-chlorophenoxy)phenylsulfonyl]-2,2-dimethyl-N-hydroxyropionamide: mp 154.9–156.1° C.; $^1$HNMR (CDCl$_3$) δ 1.45 (s, 6H), 3.48 (s, 2H), 7.02 (d, J=8.9 Hz, 2H), 7.04 (d, J=8.9 Hz, 2H), 7.38 (d, J=8.9 Hz, 2H), 7.85 (d, J=8.9 Hz, 2H); FABMS (M++H): 384.0. Anal. Calcd. for C$_{17}$H$_{18}$NSO$_5$Cl: C, 53.19; H, 4.73; N, 3.65. Found: C, 52.98; H, 4.69; N, 3.73.

4-(phenoxyphenylsulfonylmethyl)-tetrahydropyran-4-(N-hydroxycarboxamide): mp 141.8–142.9° C.; IR (KBr) 3432 (br), 1636 cm$^{-1}$; $^1$H NMR (DMSO-d$_6$) δ 1.74 (ddd, J=13.8, 10.0, 3.9 Hz, 2H), 1.98 (dm, J=13.8 Hz, 2H), 3.45 (m$_c$, 2H), 3.64 (m$_c$, 2H), 3.65 (s, 2H), 7.15 (d, J=8.8 Hz, 2H), 7.26 (d, J=7.5 Hz, 2H), 7.47 (t, J=7.5 Hz, 1H), 7.85 (d, J=8.8 Hz, 2H), 8.68 (s, 1H), 10.52 (s, 1H); $^{13}$C NMR (DMSO-d$_6$) δ 32.87 (t), 41.76 (s), 61.19 (t), 63.28 (t), 117.71 (d), 119.99 (d), 124.91 (d), 130.04 (d), 130.34 (d), 134.85 (s), 154.85 (s), 161.39 (s), 168.97 (s); FABHRMS Calcd. for C$_{19}$H$_{22}$NSO$_6$ (M$^+$+H): 392.1168. Found: 392.1162. Anal. Calcd. for C$_{19}$H$_{21}$NSO$_6$·0.5H$_2$O: C, 56.99; H, 5.54; N, 3.50. Found: C, 57.06; H, 5.35; N, 3.93.

4-[4-(4-thiophen-2-yl)phenoxyphenylsulfonylmethyl]-tetrahydropyran-4-(N-hydroxycarboxamide): mp 172.2–176.5° C.; IR (KBr) 3428 (br), 1636 cm$^{-1}$; $^1$H NMR (DMSO-d$_6$) δ 1.72 (.dm, J=14.5 Hz, 2H), 1.99 (dm, J=14.5 Hz, 2H), 3.46 (m$_c$, 2H), 3.65 (m$_c$, 2H), 3.66 (s, 2H), 7.14 (dd, J=4.9, 3.6 Hz,1H), 7.19 (d, J=8.7 Hz, 2H), 7.20 (d, J=8.9 Hz, 2H), 7.48 (dd, J=3.6, 1.2 Hz, 1H), 7.52 (dd, J=4.9, 1.2 Hz, 1H), 7.73 (d, J=8.8 Hz, 2H), 7.86 (d, J=8.8 Hz, 2H), 8.68 (s, 1H), 12.58 (s, 1H); $^{13}$CNMR (DMSO-d$_6$) δ 32.89 (t), 41.78 (s), 61.20 (t), 63.28 (t), 117.88 (d), 120.55 (d), 123.66 (d), 125.56 (d), 127.34 (d), 128.45 (d), 130.07 (d), 130.62 (s), 135.04 (s), 142.45 (s), 154.30 (s), 161.16 (s), 169.03 (s); FABHRMS Calcd. for C$_{23}$H$_{24}$NS$_2$O$_6$(M$^+$+H): 474.1045. Found: 474.1050. Anal. Calcd. for C$_{23}$H$_{23}$NS$_2$O$_6$: C, 58.33; H, 4.90; N, 3.00. Found: C, 58.18; H, 4.84; N, 3.19.

4-[4-(4-thiophen-3-yl)phenoxyphenylsulfonylmethyl]-tetrahydropyran-4-(N-hydroxycarboxamide): mp 183.5–184.4° C.; IR (KBr) 3432 (br), 1636 cm$^{-1}$; $^1$H NMR (DMSO-d$_6$) δ 1.72 (m,, 2H), 1.98 (m$_c$, 2H), 3.48 (m$_c$, 2H), 3.65 (m,, 4H), 7.18 (m$_c$, 4H), 7.55 (dd, J=5.1 Hz, 1H), 7.62 (d, J=4.9, 3.7 Hz, 2H), 7.80 (d, J=8.6 Hz, 2H), 7.86 (m$_c$, 3H), 8.69 (s, 1H), 10.58 (s, 1H); $^{13}$C NMR (DMSO-d$_6$) δ 32.88 (t), 41.79 (s), 61.19 (t), 63.28 (t), 117.71 (d), 120.42 (d), 120.81 (d), 126.09 (d), 127.10 (d), 127.97 (d), 130.06 (d), 132.10 (s), 134.89 (s), 140.54 (s), 153.86 (s), 168.85 (s); FABHRMS Calcd. for C$_{23}$H$_{24}$NS$_2$O$_6$ (M$^+$+H): 474.1045. Found: 474.1049. Anal. Calcd. for C$_{23}$H$_{23}$NS$_2$O$_6$·0.75H$_2$O: C, 56.72; H, 5.07; N, 2.88. Found: C, 56.74; H, 4.78; N, 3.22.

3,3-dimethyl-3-[(4-chlorophenoxy)phenylsulfonyl]-7N-hydroxypropionamide;

{4-[4-(4-benzo[b]thiophen-2-yl-phenoxy)phenylsulfonyl)-tetrahydropyran-4-yl]-N-hydroxyacetamide;

2-{4-[4-(phenylmethyl)phenylsulfonyl]-tetrahydropyran-4-yl}-N-hydroxyacetamide;

2-{4-[4-(4-chlorophenoxy)phenylsulfonyl]-tetrahydropyran-4-yl}-1N-hydroxyacetamide; and 2-{4-(4-(4-bromophenoxy)phenylsulfonyl]-tetrahydropyran-4-yl}-N-hydroxyacetamide.

12E. Preparation of Id where n is 2, varying R$^1$, R$^2$, R$^3$, R$^4$, and R$^5$ Similarly, following the procedures of Example 12A or 12B above, but replacing N-hydroxy-2-[1-(4-phenoxyphenylthio)-cyclopent-1-yl]-acetamide with other compounds of Formula Id where n is 0, the following compounds of Formula Id where n is 2 are prepared, for example;

4-(4-phenoxyphenylsulfonylmethyl)tetrahydropyran-4-(N-hydroxycarboxamide);

4-[4-(4-fluorophenoxy)phenylsulfonylmethyl] tetrahydropyran-4-(N-hydroxycarboxamide);

4-[4-(4-chlorophenoxy)phenylsulfonylmethyl]piperidine-4-(N-hydroxycarboxamide);

4-[4-(4-chlorophenoxy)phenylsulfonylmethyl]-1-methylpiperidine-4-(N-hydroxycarboxamide);

4-[4-(4-chlorophenoxy)phenylsulfonylmethyl]-1-cyclopropylmethylpiperidine-4-(N-hydroxycarboxamide);

4-[4-(4-chlorophenoxy)phenylsulfonylmethyl]-1-acetylpiperidine-4-l(N-hydroxycarboxamide);

4-[4-(4-chlorophenoxy)phenylsulfonylmethyll-1-(3-pyridyl)piperidine-4-(N-hydroxycarboxamide);

4-[4-(4-chlorophenoxy)phenylsulfonylmethyl]-1-(3-pyridoyl)piperidine-4-(N-hydroxycarboxamide);

N-hydroxy-2-[4-(4-phenoxyphenylsulfonyl)-N-CBZ-piperidin-4-yl)]-acetamide;

N-hydroxy-2-[4-(4-methoxyphenylsulfonyl)-N-CBZ-piperidin-4-yl)]-acetamide;

2-{4-[4-(4-fluorophenoxy)phenylsulfonyl]-N-CBZ-piperidin-4-yl}-N-hydroxyacetamide;

2-{4-[4-(4-fluorophenoxy)phenylsulfonyl]-piperidin-4-yl}-N-hydroxyacetamide;

N-hydroxy-2-[4-(4-methoxyphenylsulfonyl)-piperidin-4-yl)]-acetamide;

N-hydroxy-2-[4-(4-phenoxyphenylsulfonyl)-piperidin-4-yl)]-acetamide;

2-benzyl-N-hydroxy-3-(4-methoxyphenylsulfonyl)-propionamide;

3-benzyl-N-hydroxy-3-(3-methoxyphenylsulfonyl)-propionamide;

3-benzyl-N-hydroxy-3-(4-methoxyphenylsulfonyl)-propionamide;

3-benzyll-N-hydroxy-3-[(4-phenylthiophenyl)sulfonyl]-propionamide;

3-benzyl-N-hydroxy-3-(phenylsulfonyl)-propionamide;

3-benzyl-N-hydroxy-3-(4-phenoxyphenylsulfonyl)-propionamide;

3-benzyl-3-[(4-biphenyl)sulfonyl]-N-hydroxypropionamide;

3-benzyl-N-hydroxy-3-(2-naphthylsulfonyl)-propionamide;

3-benzyl-N-hydroxy-3-(4-methoxystyrylphenylsulfonyl)-propionamide;

3-(cyclopentylmethyl)-N-hydroxy-3-(4-methoxyphenylsulfonyl)-propionamide;

3-(cyclopentylmethyl)-N-hydroxy-2-isopropyl-3-(4-methoxyphenylsulfonyl)-propionamide;

3-ethyl -N-hydroxy-3-(4-methoxyphenylsulfonyl)-2-methylpropionamide;

3,3-dimethyl-N-hydroxy-(4-methoxyphenylsulfonyl)-propionamide;

N-hydroxy-2-[1-(4-methoxyphenylsulfonyl)-cyclopent-1-yl]-acetamide;

N-hydroxy-2-[1-(4-methoxyphenylsulfonyl)-(4-methylcyclohex-1-yl]-acetamide;

N-hydroxy-2-[1-(4-phenoxyphenylsulfonyl)-cyclohex-1-yl]-acetamide;

N-hydroxy-2-[4-(4-phenoxyphenylsulfonyl)-tetrahydropyran-4-yl]-acetamide;

2-{4-[4-(4-chlorophenoxy)phenylsulfonyl]-tetrahydropyran-4-yl}-N-hydroxyacetamide;

2-{4-[4-(4-fluorophenoxy)phenylsulfonyl]-tetrahydropyran-4-yl}-N-hydroxyacetamide; and N-hydroxy-2-[4-(4-phenoxyphenylsulfonyl)-tetrahydrothiopyran-1,1-dioxide-4-yl]-acetamide.

12F. Preparation of Id where n is 2, varying $R^1$, $R^2$, $R^3$, $R^4$, and $R^5$ Similarly, following the procedures of Example 12A above, but replacing N-hydroxy-2-[1-(4-phenoxyphenylthio)-cyclopent-1-yl]-acetamide with other compounds of Formula Id where n is 0, other compounds of Formula Id where n is 2 are prepared.

Example 13

Preparation of Compounds of Formula I where Y is tert-BuONH—

13A. Preparation of Ic where n is 2, $R^1$ and $R^2$ are Hydrogen, $R^3$ and $R^4$ when taken together with the Carbon to which they are attached are Tetrahydropyran, and R5 is 4-Phenoxyphenyl To a cooled solution of N-tert-butoxy-2-[4-(4-phenoxyphenylthio)-tetrahydropyran-4-yl]-acetamide (14.1 g, 33.9 mmol) in methanol (340 ml) was added a solution of OXONE (33.9 g) in water (170 ml). The reaction mixture was stirred for 5 hours at room temperature, concentrated to half the original volume under reduced pressure, and the residue then partitioned between ethyl acetate and water. The solvent was removed from the ethyl acetate extracts under reduced pressure. The residue chromatographed on silica gel, eluting with 10% methanol/methylene chloride, to give N-tert-butoxy-2-(4-(4-phenoxyphenylsulfonyl)-tetrahydropyran-4-yl]-acetamide as a white foam.

13B. Preparation of Ic where n is 2, $R^3$ and R4 are Hydrogen, $R^1$ and $R^2$ when taken together with the Carbon to which they are attached are N-BOC-Piperidine, and $R^5$ is 4-(4-Chlorophenoxy)phenyl To a solution of N-tert-butoxy-2-[4-(4-phenoxyphenylthiomethyl)-N-BOC-piperidin-4-yl]-carboxamide (4.96 g, 9.03 mmol) in anhydrous methylene chloride (70 mL) cooled to 0° C., was added 60% 3-chloroperoxybenzoic acid (4.96 g). After the resulting mixture was allowed to warm to room temperature over 30 minutes and stirred for 5 minutes, 13.6M aqueous methyl sulfide (1 mL, 13.62 mmol) was added in one portion. The mixture was stirred 10 minutes, partitioned with saturated aqueous sodium bicarbonate (2×50 mL), dried over magnesium sulfate, and concentrated in vacuo. Chromatography over silica gel, and eluting with 25% ethyl acetate/hexanes, gave N-tert-butoxy-2-[4-(4-phenoxyphenylsulfonylmethyl)-N-BOC-piperidin-4-yl]-carboxamide as a white foam (4.70 g, 90%). $^1$HNMR (CDCl$_3$) δ 1.31 (s, 9H), 1.46 (s, 9H), 1.59 (m$_c$, 2H), 2.18 (m$_c$, 2H), 3.42 (m$_c$, 2H), 3.45 (s, 2H), 3.62 (m$_c$, 2H), 7.01 (d, J=8.9 Hz, 2H), 7.04 (d, J=8.8 Hz, 2H), 7.38 (d, J=8.8 Hz, 2H), 7.84 (d, J=8.8 Hz, 2H), 8.44 (br s, 1H).

13C. Preparation of Ic where n is 2 and Y is tert-BuONH—, varying $R^1$, $R^2$, $R^3$, $R^4$, and $R^5$ Similarly, following the procedures of Example 13B above, but replacing N-tert-butoxy-2-[4-(4-phenoxyphenylthiomethyl)-N-BOC-piperidin-4-yl]-carboxamide with other compounds of Formula Ib, the following compound of Formula Ic where n is 2 and Y is tert-BuONH— was prepared:

N-tert-butoxy-4-[4-(4-pyridyloxy)phenylsulfonylmethyl]-tetrahydropyran-carboxamide: IR (KBr) 3434, 1684 cm$^{-1}$; $^1$HNMR (CDCl$_3$) δ 1.33 (s, 9H), 2.01 (m$_c$, 2H), 2.24 (m$_c$, 2H), 3.55 (s, 2H), 3.79 (m$_c$, 4H), 6.93 (d, J=6.3 Hz, 2H), 7.22 (d, J=8.8 Hz, 2H), 7.96 (d, J=8.8 Hz, 2H), 8.38 (s, 1H), 8.57 (d, J=6.3 Hz, 2H); FABHRMS Calcd. for $C_{22}H_{28}N_2SO_6$ ($M^+$+H) 449.1746. Found: 449.1757.

N-tert-butoxy-4-[4-(5-chloro-2-pyridyloxy)phenylsulfonylmethyl]-tetrahydropyran-carboxamide: mp (broad) 100.8–135.8° C.; IR (KBr) 3436 (br), 1684 cm$^{-1}$; $^1$HNMR (DMSO-d$_6$) δ 1.20 (s, 9H), 1.72 (m$_c$, 2H), 2.03 (m$_c$, 2H), 3.48 (m$_c$, 2H), 3.67 (m$_c$, 2H), 3.76 (s, 2H), 7.23 (dd, J=8.8, 0.5 Hz, 1H), 7.41 (d, J=8.8 Hz, 2H), 7.91 (d, J=8.8 Hz, 2H), 8.03 (dd, J=8.8, 2.7 Hz, is 1H), 8.25 (dd, J=2.7, 0.5 Hz, 1H), 8.30 (s, 1H), 10.32 (s, 1H); $^{13}$CNMR (DMSO-d$_6$) δ 26.66 (q), 33.09 (t), 42.37 (s), 61.03 (t), 63.36 (t), 80.64 (s), 113.89 (d), 121.38 (d), 126.33 (s), 129.53 (d), 137.00 (s), 140.34 (d), 145.74 (d), 157.87 (s), 160.66 (s), 171.25 (s); FABHRMS Calcd. for $C_{22}H_{28}N_2SO_6Cl$ ($M^+$+H): 483.1357. Found: 483.1354. Anal. Calcd. for $C_{22}H_{27}N_2SO_6Cl$: C, 54.71; H, 5.63; N, 5.80. Found: C, 54.46; H, 5.60; N, 5.98.

N-tert-butoxy-3-[4-(5-chloro-2-pyridyloxy)phenylsulfonyl]-2,2-dimethyl-propionamide: mp (broad) 64.5–70.5° C.; $^1$HNMR (DMSO-d$_6$) δ 1.19 (s, 9H), 1.29 (s, 6H), 3.65 (s, 2H), 7.24 (d, J=8.7 Hz, 1H), 7.41 (d, J=8.8 Hz, 2H), 7.91 (d, J=8.8 Hz, 2H), 8.04 (dd, J=8.8, 2.7 Hz, 1H), 8.26 (d, J=2.7 Hz, 1H), 10.17 (s, 1H); $^{13}$C NMR (DMSO-d6) 6 25.01 (q), 26.47 (q), 40.74 (s), 63.03 (t), 80.79 (s), 113.91 (d), 121.38 (d), 126.32 (s), 129.35 (d), 130.66 (s), 140.36 (d), 145.75 (d), 157.72 (s), 160.68 (s), 173.14 (s); FABHRMS Calcd. for $C_{20}H_{26}N_2SO_5Cl$ ($M^+$+H): 441.1251. Found:

441.1248. Anal. Calcd. for $C_{20}H_{25}N_2SO_5Cl$: C, 54.48; H, 5.71; N, 6.35. Found: C, 54.37; H, 5.69; N, 6.57.

13D. Preparation of Ic where n is 2 and Y is tert-BuONH—, varying $R^1$, $R^2$, $R^3$, $R^4$, and $R^5$ Similarly, following the procedures of Example 13A above, but replacing N-tert-butoxy-2-(4-(4-phenoxyphenylthio)-tetrahydropyran-4-yl]-acetamide with other compounds of Formula Ib, the following compounds of Formula Ic where n is 2 and Y is tert-BuONH— were prepared;

N-tert-butoxy-2-[4-(4-phenoxyphenylsulfonyl)-N-CBZ-piperidin-4-yl)]-acetamide;

N-tert-butoxy-2-[4-(4-methoxyphenylsulfonyl)-N-CBZ-piperidin-4-yl)]-acetamide;

N-tert-butoxy-2-(4-[4-(4-fluorophenoxy)phenylsulfonyl]-piperidin-4-yl}-acetamide;

N-tert-butoxy-2-[4-(4-methoxyphenylsulfonyl)-piperidin-4-yl)]-acetamide;

N-tert-butoxy-2-[4-(4-phenoxyphenylsulfonyl)-piperidin-4-yl)]-acetamide;

2-benzyl-N-tert-butoxy-3-(4-methoxyphenylsulfonyl)-propionamide;

3-benzyl-N-tert-butoxy-3-(3-methoxyphenylsulfonyl)-propionamide;

3-benzyl-N-tert-butoxy-3-(4-methoxyphenylsulfonyl)-propionamide;

3-benzyl-N-tert-butoxy-3-[(4-phenylthiophenyl)sulfonyl]-propionamide;

3-benzyl-N-tert-butoxy-3-(phenylsulfonyl)-propionamide;

3-benzyl-N-tert-butoxy-3-(4-phenoxyphenylsulfonyl)-propionamide;
3-benzyl-N-tert-butoxy-3-[(4-biphenyl)sulfonyl]-propionamide;
3-benzyl-N-tert-butoxy-3-(2-naphthylsulfonyl)-propionamide;
3-benzyl-N-tert-butoxy-3-(4-methoxystyrylphenylsulfonyl)-propionamide;
N-tert-butoxy-3-(cyclopentylmethyl)-3-(4-methoxyphenylsulfonyl)-propionamide;
N-tert-butoxy-3-(cyclopentylmethyl)-2-isopropyl-3-(4-methoxyphenylsulfonyl)-propionamide;
N-tert-butoxy-3-ethyl-2-methyl-3-(4-methoxyphenylsulfonyl)-propionamide;
N-tert-butoxy-3,3-dimethyl-(4-methoxyphenylsulfonyl)-propionamide;
N-tert-butoxy-2-[1-(4-methoxyphenylsulfonyl)-cyclopent-1-yl]-acetamide;
N-tert-butoxy-2-[1-(4-methoxyphenylsulfonyl)-(4-methylcyclohex-1-yl]-acetamide;
N-tert-butoxy-2-(4-(4-phenoxyphenylsulfonyl)-cyclohexanone-4-yl]-acetamide ethylene ketal;
N-tert-butoxy-2-[1-(4-phenoxyphenylsulfonyl)-cyclohex-1-yl]-acetamide;
N-tert-butoxy-2-[4-(4-phenoxyphenylsulfonyl)-tetrahydropyran-4-yl]-acetamide;
N-tert-butoxy-2-{4-[4-(4-chlorophenoxy)phenylsulfonyl]-tetrahydropyran-4-yl}-acetamide;
N-tert-butoxy-2-{4-[4-(4-fluorophenoxy)phenylsulfonyl]-tetrahydropyran-4-yl}-acetamide;
N-tert-butoxy-2-[4-(4-phenoxyphenylsulfonyl)-tetrahydrothiopyran-1,1-dioxide-4-yl]-acetamide;
N-tert-butoxy-2-(4-methoxyphenylsulfonyl)-cyclohexanecarboxamide; and
N-tert-butoxy-trans-2-(4-methoxyphenylsulfonyl)-cyclopentanecarboxamide.

13E. Preparation of Ic where n is 2, varying $R^1$, $R^2$, $R^3$, $R^4$, and $R^5$ Similarly, following the procedures of Example 13A above, but replacing N-tert-butoxy-2-[4-(4-phenoxyphenylthio)-N-CBZ-piperidin-4-yl)]-acetamide with other compounds of Formula Ib, other compounds of Formula Ic where n is 2 and Y is tert-BuONH— are prepared.

Example 14

Preparation of Compounds of Formula Ic where Y is tert-BuONH—

14A. Preparation of Ic where n is 2, $R^1$ and $R^2$ are Hydrogen, $R^3$ and $R^4$ when taken together with the Carbon to which they are attached are Piperidine, and $R^5$ is 4-Phenoxyphenyl To a solution of N-tert-butoxy-2-[4-(4-phenoxyphenylsulfonyl)-N-CBZ-piperidin-4-yl)]-acetamide (1.2 g, 2.1 mmol) in ethanol (21 ml) was added 10% palladium on carbon (1 g) and ammonium formate (6.7 g), and the mixture refluxed for 1 hour. The mixture was filtered through Celite, the filter cake washed with ethanol (150 ml) followed by 10% methanol in methylene chloride (150 ml). Solvent was removed from the filtrate under reduced pressure and the residue was dissolved in hot ethyl acetate. Filtration, concentration of the filtrate, followed by silica gel chromatography and elution with 10% methanol/methylene chloride gave N-tert-butoxy-2-[4-(4-phenoxyphenylsulfonyl)-piperidin-4-yl)]-acetamide as a colorless oil.

14B. Preparation of Ic where n is 2, varying $R^1$, $R^2$, $R^3$, $R^4$, and $R^5$ Similarly, following the procedures of Example 14A above, but replacing N-tert-butoxy-2-(4-(4-phenoxyphenylsulfonyl)-N-CBZ-piperidin-4-yl)]-acetamide with other N-CBZ protected compounds of Formula I, other compounds of Formula I where n is 2 and Y is tert-BuONH— are prepared.

Example 15

Preparation of Compounds of Formula Id where Y is HONH—

15A. Preparation of Id where n is 2, $R^1$ and $R^2$ are Hydrogen, $R^3$ and $R^4$ when taken together with the Carbon to which they are attached are Piperidine, and $R^5$ is 4-Phenoxyphenyl A solution of N-tert-butoxy-2-[4-(4-phenoxyphenylsulfonyl)-piperid-4-yl)]-acetamide (27 mg, 0.05 mmol) in dichloroethane (2 ml) was cooled to −20° C., and saturated with hydrochloric acid gas for 30 minutes. The reaction vessel was then sealed and the solution stirred for two days at 25° C. Solvent was removed from the reaction mixture under reduced pressure, and the residue dissolved in 50% methanol in methylene chloride. Addition of hexane precipitated N-hydroxy-2-[4-(4-phenoxyphenylsulfonyl)-piperidin-4-yl)]-acetamide, m/e=391 (MH$^+$, FAB).

15B. Preparation of Id where n is 2, varying $R^1$, $R^2$, $R^3$, $R^4$, and $R^5$ Similarly, following the procedures of Example 15A above, but replacing N-tert-butoxy-2-[4-(4-phenoxyphenylsulfonyl)-piperidin-4-yl)]-acetamide with other compounds of Formula Ic where Y is tert-BuONH—, the following compounds of Formula Id where n is 2 and Y is HONH— were prepared:

N-hydroxy-2-[4-(4-phenoxyphenylsulfonyl)-N-CBZ-piperidin-4-yl)]-acetamide, m/e=525 (MH$^+$);

N-hydroxy-2-(4-(4-methoxyphenylsulfonyl)-N-CBZ-piperidin-4-yl)]-acetamide, m/e=463 (M$^+$, FAB);

2-{4-[4-(4-fluorophenoxy)phenylsulfonyl]-piperidin-4-yl}-N-hydroxyacetamide, m.p. 196–197° C.;

2-{4-[4-(4-chlorophenoxy)phenylsulfonyl]-piperidin-4-yl}-N-hydroxyacetamide, m.p. 200–201° C.;

2-{4-[4-(4-chlorophenoxy)phenylsulfonyl]-tetrahydropyran-4-yl}-N-hydroxyacetamide: mp 135.7–136.1 ° C.; $^1$HNMR (CDCl$_3$) δ 1.60 (m$_c$, 2H), 1.83 (m$_c$, 2H), 3.00 (s, 2H), 3.66 (m$_c$, 2H), 3.88 (m,, 2H), 7.06 (d, J=8.8 Hz, 2H), 7.09 (d, J=8.8 Hz, 2H), 7.42 (d, J=8.9 Hz, 2H), 7.79 (d, J=8.9 Hz, 2H), 7.25 (s, 1H), 9.49 (s, 1H); FABHRMS Calcd. for C$_{19}$H$_{20}$NSO$_6$Cl (M$^+$+H): 426.0778. Found: 426.0775. Anal. Calcd. for C$_{19}$H$_{20}$NSO$_6$Cl: C, 53.59; H, 4.73; N, 3.29. Found: C, 53.30; H, 4.67; N, 3.35.

2-[4-(4-cyclohexyloxyphenylsulfonyl]-tetrahydropyran-4-yl}-N-hydroxyacetamide: m.p. 77–78° C.;

N-hydroxy-2-[4-(4-methoxyphenylsulfonyl)-piperidin-4-yl)]-acetamide, m/e=329 (MH$^+$);

N-hydroxy-2-[4-(4-phenoxyphenylsulfonyl)-piperidin-4-yl)]-acetamide, m/e=391 (MH$^+$);

2-benzyll-N-hydroxy-3-(4-methoxyphenylsulfonyl)-propionamide, m/e=350.2 (MH$^+$);

3-benzyl-N-hydroxy-3-(3-methoxyphenylsulfonyl)-propionamide, m/e=350.2 (MH$^+$);

3-benzyl-N-hydroxy-3-(4-methoxyphenylsulfonyl)-propionamide, m/e=350.2 (MH$^+$);

3-benzyl-N-hydroxy-3-[(4-phenylthiophenyl)sulfonyl]-propionamide, m/e=427 (MH$^+$);

3-benzyl-N-hydroxy-3-(phenylsulfonyl)-propionamide, m/e=320 (MH$^+$);

3-benzyll-N-hydroxy-3-(4-phenoxyphenylsulfonyl)-propionamide, m/e=412.2 (MH$^+$);

3-benzyl-N-hydroxy-3-[(4-biphenyl)sulfonyl]-propionamide; m/e=395 (MH$^+$);

3-benzyl-N-hydroxy-3-(2-naphthylsulfonyl)-propionamide, m/e=370.1 (MH$^+$);

3-benzyl-N-hydroxy-3-[(4-methoxystyrylphenylsulfonyl]-propionamide, m/e=452.2 (MH$^+$);

3-(cyclopentylmethyl)-N-hydroxy-3-(4-methoxyphenyl-sulfonyl)-propionamide, m/e=342 (MH$^+$);

3-(cyclopentylmethyl)-N-hydroxy-2-isopropyl-3-(4-methoxyphenylsulfonyl)-propionamide;

3-ethyl-N-hydroxy-2-methyl-3-(4-methoxyphenyl-sulfonyl)-propionamide, m/e=301 (MH$^+$);

3,3-dimethyl-3-(4-methoxyphenylsulfonyl)-N-hydroxypropionamide, elemental analysis: $C_1H_1N$;

N-hydroxy-2-[4-(4-methoxyphenylsulfonyl)-cyclopent-1-yl]-acetamide, m/e=313 (MH$^+$);

N-hydroxy-2-[4-(4-methoxyphenylsulfonyl)-(4-methylcyclohex-1-yl]-acetamide, m/e=341 (MH$^+$);

N-hydroxy-2-[4-(4-phenoxyphenylsulfonyl)-cyclohex-1-yl]-acetamide, m/e=389 (MH$^+$);

N-hydroxy-2-[4-(4-phenoxyphenylsulfonyl)-tetrahydropyran-4-yl]-acetamide, m.p. 88.5–90° C., m/e=391 (MH$^+$);

2-{4-[4-(4-chlorophenoxy)phenylsulfonyl]-tetrahydropyran-4-yl}-N-hydroxyacetamide;

2-{4-[4-(4-fluorophenoxy)phenylsulfonyl]-tetrahydropyran-4-yl}-N-hydroxyacetamide, m.p. 91–95° C.;

N-hydroxy-2-[4-(4-phenoxyphenylsulfonyl)-tetrahydrothiopyran-1,1-dioxide-4-yl]-acetamide, m/e=440.1 (MH$^+$);

N-hydroxy-trans-2-(4-methoxyphenylsulfonyl)-cyclopentanecarboxamide, m/e=313 (MH$^+$);

N-hydroxy-trans-2-(4-methoxyphenylsulfonyl)-cyclohexanecarboxamide, m/e=327 (MH$^+$); and 2-benzyl-N-hydroxy-trans-2-(4-methoxyphenylsulfonyl)-cyclopentanecarboxamide, m/e=390 (MH$^+$, FABMS).

15C. Preparation of Id where n is 2, varying $R^1$, $R^2$, $R^3$, $R^4$, and $R^5$ Similarly, following the procedures of Example 15A above, but replacing N-tert-butoxy-2-[4-(4-phenoxyphenylsulfonyl)-piperidin-4-yl)]-acetamide with other compounds of Formula Ic where Y is tert-BuONH—, other compounds of Formula Id where n is 2 and Y is HONH— are prepared, for example:

2-{4-[4-(4-fluorophenoxy)phenylsulfonyl]-N-CBZ-piperidin-4-yl}-N-hydroxyacetamide;

2-{1-methyl-4-[4-(4-chlorophenoxy)-phenylsulfonyl]-piperidin-4-yl}-N-hydroxyacetamide;

N-hydroxy-2-{1-methyl-4-[4-(4-fluorophenoxy)-phenylsulfonyl]-piperidin-4-yl}-acetamide; and 2-{4-[4-(4-bromophenoxy)-phenylsulfonyl]-tetrahydropyran-4-yl}-N-hydroxyacetamide.

15D. Preparation of Id where n is 2, $R^1$ and $R^2$ are Hydrogen, $R^3$ and $R^4$ when taken together with the Carbon to which they are attached are Cyclohexanone, and $R^5$ is 4-Phenoxyphenyl Following the procedure outlined in Example 15A, N-hydroxy-2-[4-(4-phenoxyphenylsulfonyl)-cyclohexanone-4-yl]-acetamide ethylene ketal (400 mg) was prepared from the corresponding N-tert-butoxy precursor. The above product was dissolved in a 1:1 mixture of acetone and 1M hydrochloric acid (40 ml) and stirred at room temperature for 18 hours. The reaction was concentrated under reduced pressure and extracted with ethyl acetate. Silica gel chromatography using 10% methanol/methylene chloride gave 2-[4-(4-phenoxyphenylsulfonyl)cyclohexanone-4-yl]-N-hydroxyacetamide as a white solid: m.p. 106° C. (dec), m/e=404 (MH$^+$, FABMS).

15E. Preparation of Id where n is 2, $R^3$ and $R^4$ are Hydrogen, $R^1$ and $R^2$ when taken together with the Carbon to which they are attached are Piperidine, and $R^5$ is 4-(4-Chlorophenoxy)phenyl To a sealed tube containing the free base N-tert-butoxy-2-{4-[4-(4-phenoxy)phenylsulfonylmethyl]-piperidin-4-yl}-carboxamide (780 mg, 1.62 mmol) in 1,2-dichloroethane (35 mL) at –30° C., was bubbled in gaseous hydrochloric acid until the saturation point was reached. The reaction vessel was then sealed and the solution stirred for two days. After the vessel was recooled to –30° C. and opened, a stream of nitrogen gas bubbled through the solution, which was then warmed to room temperature. The mixture was concentrated to afford 2-{4-[4-(4-chlorophenoxy)phenylsulfonylmethyl]-piperidin-4-yl}-N-hydroxycarboxamide (747 mg, 100%). mp 166.7–176.2° C.; $^1$HNMR (CD$_3$OD) δ 2.39 (m$_c$, 2H), 3.12 (m$_c$, 2H), 3.36 (m$_c$, 2H), 3.63 (s, 2H), 7.12 (d, J=8.9 Hz, 2H), 7.15 (d, J=8.9 Hz, 2H), 7.44 (d, J=9.0 Hz, 2H), 7.89 (d, J=8.9 Hz, 2H); FABMS (M$^+$+H): 425.0; Anal. Calcd. for $C_{19}H_{21}N_2SO_5Cl·HCl·1.5 H_2O$: C, 46.73; H, 4.33; N, 5.74. Found: C, 46.83; H, 4.66; N, 5.71.

15F. Preparation of Id where n is 2, varying $R^1$, $R^2$, $R^3$, $R^4$, and $R^5$ Similarly, following the procedures of Example 15E above, but replacing N-tert-butoxy-2-{4-[4-(4-chlorophenoxy)phenylsulfonylmethyl]-piperidin-4-yl)}-carboxamide with other compounds of Formula Ic where Y is tert-BuONH—, other compounds of Formula Id where n is 2 and Y is HONH— were prepared, for example:

2-{4-[4-(4-chlorophenoxy)phenylsulfonylmethyl]-1-(cyclopropylmethyl)piperidin-4-yl}-N-hydroxycarboxamide hydrochloride (1.30 g, 84%). mp 120.5–124.0° C.; IR (KBr) 3429 (br), 1582 cm$^{-1}$; $^1$HNMR (CD$_3$OD) δ 0.40–0.50 (m, 2H), 0.73–0.81 (m, 2H), 1.12 (m$_c$, 1H), 2.18 (m$_c$, 2H), 2.41 (d, J=14.8 Hz, 2H), 2.63 (d, J=14.3 Hz, 2H), 3.03 (m$_c$, 2H), 3.10 (m$_c$, 2H) 3.60 (m$_c$, 3H), 7.13 (m$_c$, 4H), 7.43 (d, J=8.7 Hz, 2H), 7.89 (d, J=8.8 Hz, 2H), 7.93 (d, J=8.8 Hz, 2H); FABMS (M$^+$+H): 479.1. Anal. Calcd. for $C_{23}H_{27}N_2SO_5Cl·HCl·H_2O$: C, 51.77; H, 5.09; N, 5.25. Found: C, 51.90; H, 5.53; N, 5.26.

2-{4-[4-(4-chlorophenoxy)phenylsulfonylmethyl]-N-hydroxy-1-nicotinoylmethylpiperidin-4-yl}-carboxamide hydrochloride (590 mg, 89%). mp 160.5° C. (effervescence); IR (KBr) 3426 (br), 1638 cm$^{-1}$; $^1$HNMR (CD$_3$OD) δ 1.97 (m., 2H), 2.25 (m$_c$, 2H), 3.55 (m., 4H), 3.64 (s, 2H), 7.10 (d, J=8.9 Hz, 2H), 7.13 (d, J=8.7 Hz, 2H), 7.43 (d, J=8.6 Hz, 2H), 8.12 (m$_c$, 1H), 8.61 (d, J=7.9 Hz, 2H), 8.92 (d, J=5.5 Hz, 2H), 8.98 (br s, 1H); FABMS (M$^+$+H): 530.0. Anal. Calcd. for $C_{25}H_{29}N_3SO_6Cl·HCl·0.5H_2O$: C, 51.38; H, 4.14; N, 7.19. Found: C, 51.80; H, 4.46; N, 7.25.

2-{4-[4-(4-chlorophenoxy)phenylsulfonylmethyl]-N-hydroxy-1-methansulfonylpiperidin-4-yl}-carboxamide hydrochloride (682 mg, 69%). mp 107.3–112.3° C.; $^1$HNMR (CDCl$_3$) δ 1.95 (m$_c$, 2H), 2.40 (m$_c$, 2H), 2.79 (s, 3H), 3.12 (m$_c$, 2H), 3.42 (s, 2H), 3.51 (m., 2H), 7.01 (d, J=8.9 Hz, 2H), 7.07 (d, J=8.9 Hz, 2H), 7.39 (d, J=8.9 Hz, 2H), 7.83 (d, J=8.9 Hz, 2H); FABMS (M$^+$+H): 503.2. Anal. Calcd. for $C_{20}H_{23}N_2S_2O_7Cl$: C, 47.76; H, 4.61; N, 5.57. Found: C, 47.32; H, 4.56; N, 5.52.

4-[4-(4-pyridyloxy)phenylsulfonylmethyl]-tetrahydropyran-4-(N-hydroxycarboxamide) hydrochloride: mp 188–197° C.; IR (KBr) 3431, 1638 cm$^{-1}$; $^1$HNMR (DMSO-d$_6$) δ 1.73 (m$_c$, 2H), 2.01 (dm, J=14.7 Hz, 2H), 3.43 (m$_c$, 2H), 3.65 (m$_c$, 2H), 3.78 (s, 2H), 7.56 (m$_c$, 4H), 8.02 (d, J=8.7 Hz, 2H), 8.82 (d, J=6.6 Hz, 2H), 10.64 (s, 1H); $^{13}$CNMR (DMSO-d$_6$) δ 33.01 (t), 39.78 (t), 61.13 (s), 63.26

(t), 114.48 (d), 121.81 (d), 130.87 (d), 138.41 (s), 144.92 (d), 156.14 (s), 168.4 (s), 168.8 (s); Anal. Calcd. for $C_{18}H_{21}N_2SO_6Cl\cdot HCl\cdot 0.6\ H_2O$: C, 49.17; H, 5.09; N, 6.37. Found: C, 49.16; H, 5.03; N, 6.27.

4-[4-(5-chloro-2-pyridyloxy)phenylsulfonylmethyl]-tetrahydropyran-4-(N-hydroxycarboxamide): mp 141.9–142.7° C.; IR (KBr) 3432, 1636 cm$^{-1}$; $^1$HNMR (DMSO-d$_6$) δ 1.73 (m$_c$, 2H), 2.01 (dm, J=14.7 Hz, 2H), 3.33 (s, 2H), 3.46 (m$_c$, 2H), 3.64 (m$_c$, 2H), 7.23 (dd, J=8.7, 0.4 Hz, 2H), 7.40 (d, J=8.8 Hz, 2H), 7.92 (d, J=8.8 Hz, 2H), 8.03 (d, J=8.7, 2.7 Hz, 2H), 8.26 (dd, J=2.7, 0.4 Hz, 1H), 8.69 (s, 1H), 10.62 (s, 1H); $^{13}$CNMR (DMSO-d$_6$) δ 32.89 (t), 41.81 (s), 60.96 (t), 63.26 (t), 113.88 (d), 121.32 (d), 126.31 (s), 129.58 (d), 136.93 (s), 140.33 (s), 145.74 (d), 157.82 (s), 160.69 (s), 169.02 (s); FABHRMS Calcd. for $C_{18}H_{19}N_2SO_6Cl$ (M$^+$+H): 427.0731. Found: 427.0726. Anal. Calcd. for $C_{18}H_{19}N_2SO_6Cl\cdot 0.5H_2O$: C, 49.49; H, 4.61; N, 6.41. Found: C, 49.54; H, 4.35; N, 6.47.

3-[4-(5-chloro-2-pyridyloxy)phenylsulfonyl]-2,2-dimethyl-N-hydroxypropionamide: mp 115.8–116.6° C.; IR (KBr) 3412 (br), 1644 cm$^{-1}$; $^1$HNMR (CD$_3$OD) δ 1.38 (s, 6H), 3.58 (s, 2H), 7.13 (d, J=8.7 Hz, 1H), 7.34 (d, J=8.8 Hz, 2H), 7.89 (dd, J=8.7, 2.7 Hz, 2H), 7.95 (d, J=8.8 Hz, 1H), 8.15 (d, J=2.5 Hz, 1H); $^{13}$C NMR (CD$_3$OD) δ 25.55 (q), 41.76 (s), 65.06 (t), 114.91 (d), 122.35 (d), 128.40 (s), 130.98 (d), 138.21 (s), 141.44 (d), 146.88 (d), 159.89 (s), 162.32 (s), 174.51 (s); FABHRMS Calcd. for $C_{16}H_{18}N_2SO_5Cl$ (M$^+$+H): 385.0625. Found: 383.0625. Anal. Calcd. for $C_{16}H_{17}N_2SO5Cl$: C, 49.94; H, 4.48; N, 7.28. Found: C, 49.58; H, 4.42; N, 7.30.

15G. Preparation of Id where n is 2, $R^3$ and $R^4$ are Hydrogen, $R^1$ and $R^2$ when taken together with the Carbon to which they are attached are 1-Picolylpiperidine, and $R^5$ is 4-(4-Chlorophenoxy)phenyl A solution containing N-tert-butoxy-2-{4-[4-(4-chlorophenoxy)phenylsulfonylmethyl]-1-picolylpiperidin-4-yl}-carboxamide (324 mg, 0.566 mmol) in trifluoroacetic acid (5 mL) was heated to 30° C. for 1.5 hours, cooled to room temperature, and concentrated in vacuo. The residue was dissolved in ethyl acetate (100 mL), washed with saturated sodium bicarbonate (2×30 mL), dried over magnesium sulfate, and concentrated in vacuo. Chromatography over silica gel, eluting with 6% methanol/methylene chloride, yielded 2-{4-[4-(4-chlorophenoxy)phenylsulfonylmethyl]-1-picolylpiperidin-4-yl}-N-hydroxycarboxamide hydrochloride: mp 222.5–223.9° C.; IR (KBr) 3436 (br), 1645 cm$^{-1}$; $^1$HNMR (DMSO-d$_6$) δ 2.15 (m$_c$, 3H), 2.40 (m$_c$, 2H), 3.32 (m$_c$, 2H), 3.57 (m$_c$, 2H), 3.97 (m$_c$, 2H), 4.44 (m$_c$, 2H), 4.51 (m$_c$, 2H), 7.19 (m$_c$, 4H), 7.50 (d, J=8.8 Hz, 2H), 7.87 (m$_c$, 3H), 8.49 (m$_c$, 1H), 8.85 (m$_c$, 1H), 8.99 (br s, 1H); FABMS (M$^+$+H): 516.1. Anal. Calcd. for $C_{29}H_{34}N_3SO_5Cl\cdot 2HCl\cdot 0.5\ H_2O$: C, 50.22; H, 4.89; N, 7.03. Found: C, 50.17; H, 4.65; N, 7.00.

Example 16

Preparation of Compounds of Formula Ih

16A. Preparation of Ie where $R^1$, $R^2$ and $R^3$ are Hydrogen, and $R^4$ is Benzyl To a cooled solution of 3-benzyl-3-(4-bromophenylthio)-propionic acid in methanol (50 ml) was added a solution of OXONE (8 g) in water (50 ml). The reaction mixture was stirred for 2 hours at room temperature, and then partitioned between methylene chloride and water. The solvent was removed from the organic layer under reduced pressure, to give 3-benzyl-3-(4-bromophenylsulfonyl)-propionic acid, as a crystalline solid.

16B. Preparation of If where $R^1$, $R^2$ and $R^3$ are Hydrogen, and $R^4$ is Benzyl 1. A solution of 3-(4-bromophenyl)sulfonyl-4-benzylpropionic acid (200 mg, 0.52 mmol), phenylboronic acid (127 mg, 1.04 mmol), and tetrakis(triphenylphospine) palladium(O) (24 mg, 0.021 mmol) in a 1:1 mixture of ethanol and benzene (5 ml) was heated to reflux temperature with stirring. A solution of 2M sodium carbonate (1 ml) was added to the reaction mixture, and stirring continued at reflux for approximately 2 hours. The mixture was cooled and then partitioned between ethyl acetate and water. The solvent layer was washed with brine, dried over magnesium sulfate, filtered, and solvent removed under reduced pressure. The residue was chromatographed, eluting with 7% methanol/methylene chloride, to yield 3-(4-biphenyl) sulfonyl-4-benzylpropionic acid. 1HNMR (CDCl$_3$): 7.75 ppm (m, 14H); 3.42 ppm (dd, 1H); 2.82 ppm (dd, 1H); 2.77 ppm (dd, 1H); 2.51 ppm (dd, 1H).

16C. Preparation of Ih where $R^1$, $R^2$, and $R^3$ are Hydrogen and $R^4$ is Benzyl The 3-(4-biphenyl)sulfonyl-4-benzylpropionic acid, prepared as shown above, was then converted to 3-(4-biphenyl) sulfonyl-4-benzyl-N-hydroxypropionamide, m.p. 65° C. (shrinks with decomposition) as described in Examples 10A.

16D. Preparation of Ifb where $R^1$ and $R^2$ Together with the Carbon to which they are attached represent Tetrahydropyran-4-yl, $R^3$ and $R^4$ are Hydrogen, $R^5$ is 4-(Thiophen-2-yl)phenoxyphenyl 1. To a mechanically stirred suspension of 4-[4-(4-bromophenoxy)phenylthiomethyl]-tetrahydropyran-4-carboxylic acid (5.50 g, 13.0 mmol) in 20% tetrahydrofuran/methanol (135 mL) cooled to 15° C., was added a solution of OXONE (13.0 g, 21.2 mmol) in water (86 mL) dropwise, maintaining an internal temperature of 15–20° C. The mixture was stirred for 12 hours and dissolved in 40% ethyl acetate/water (1200 mL). The layers were partitioned, and the water layer back extracted using ethyl acetate (2×300 mL). The combined ethyl acetate layers were dried (MgSO$_4$), concentrated, and the residue crystallized from the minimum amount of methylene chloride/hexanes to afford 4-[4-(4-bromophenoxy)phenylsulfonylmethyl]-tetrahydropyran-4-carboxylic acid as a white powder, which was used without further purification (5.00 g, 84%).

2. To a solution of 4-[4-(4-bromophenoxy) phenylsulfonylmethyl]-tetrahydropyran-4-carboxylic acid (1.10 g, 2.42 mmol) of in N,N-dimethylformamide (15 mL) was added tetrakis(triphenylphosphine)palladium(O) (108 mg), 2-thiophene boronic acid (857 mg, 6.70 mmol), followed by 2M aqueous sodium carbonate (2.7 mL, 5.4 mmol). The reaction was heated to reflux for 10 hours, cooled to room temperature, and the mixture partitioned between methylene chloride (100 mL) and 1N aqueous hydrochloric acid (20 mL). The aqueous layer was back extracted with methylene chloride (100 mL), and the combined organic layers dried (MgSO$_4$), the residue chromatographed over 100 g of silica gel (eluted with methylene chloride to 10% methanol/methylene chloride), and the resulting foam crystallized from the minimum amount of methylene chloride/hexanes to afford 4-[4-(4-(thiophen-2-yl)phenoxy)phenylsulfonylmethyl]-tetrahydropyran-4-carboxylic acid (1.04 g, 94%). mp 181.2–193.3° C.; IR (KBr) 3432 (br), 1718.9 cm$^{-1}$; $^1$H NMR (DMSO-d$_6$) δ 1.67 (ddd, J=13.8, 9.4, 4.0 Hz, 2H), 1.95 (dm, J=13.8 Hz, 2H), 3.47 (m$_c$, 2H), 3.67 (m$_c$, 2H), 3.68 (s, 2H), 7.14 (dd, J=4.9, 3.6 Hz, 1H), 7.20 (d, J=8.8 Hz, 2H), 7.22 (d, J=8.9 Hz, 2H), 7.50 (dd, J=3.6, 1.2 Hz, 1H), 7.54 (dd, J=4.9, 1.2 Hz, 1H), 7.74 (d, J=8.8 Hz, 2H), 7.87 (d, J=8.8 Hz, 2H), 12.80 (s, 1H);

$^{13}$CNMR (DMSO-d$_6$) δ 32.92 (t), 42.25 (s), 61.73 (t), 63.26 (t), 117.82 (d), 123.75 (d), 125.66 (d), 127.39 (d), 128.50 (d), 130.08 (d), 130.74 (s), 134.90 (s), 142.42 (s), 154.13 (s), 161.33 (s), 174.39 (s); FABHRMS Calcd. for C$_{23}$H$_{24}$S$_2$O$_6$ (M$^+$+H): 459.0936. Found: 459.0936. Anal. Calcd. for C$_{23}$H$_{23}$S$_2$O$_6$: C, 60.24; H, 4.83. Found: C, 60.57; H, 4.90.

16E. Preparation of Ifb where R$^1$ and R$^2$ Together with the Carbon to which they are attached represent Tetrahydropyran-4-yl, R$^3$ and R$^4$ are Hydrogen, R$^5$ is 4-(Thiophen-3-yl)phenoxyphenyl Similarly, following the above procedure, other compounds of Formula Ifb, were prepared, for example replacing 2-thiophene boronic acid with 3-thiophene boronic acid, 4-[4-(4-(thiophen-3-yl)phenoxy)phenylsulfonylmethyl]-tetrahydropyran-4 -carboxylic acid was prepared: mp 206.6–212.4° C.; IR (KBr) 3430 (br), 1719 cm$^{-1}$; $^1$HNMR (DMSO-d$_6$) δ 1.67 (m$_c$, 2H), 1.95 (m$_c$, 2H), 3.47 (m$_c$, 2H), 3.66 (m$_c$, 2H), 3.67 (s, 2H), 7.20 (m$_c$, 4H), 7.56 (dd, J=5.0, 1.4 Hz, 1H), 7.64 (d, J=5.0, 2.9 Hz, 2H), 7.81 (d, J=8.7 Hz, 2H), 7.87 (m$_c$, 2H), 7.96 (s, 1H), 12.77 (s, 1H); $^{13}$CNMR (DMSO-d$_6$) δ 32.92 (t), 40.38 (s), 61.19 (t), 63.26 (t), 117.66 (d), 120.54 (d), 120.87 (d), 126.04 (d), 127.07 (d), 127.96 (d), 130.02 (d), 132.00 (s), 134.66 (s), 140.45 (s), 160.80 (s), 174.32 (s); FABHRMS Calcd. for C$_{23}$H$_{23}$S$_2$O$_6$ (M$^+$+H): 459.0936. Found: 459.0934. Anal. Calcd. for C$_{23}$H$_{22}$S$_2$O$_6$.0.5H$_2$O: C, 59.08; H, 4.96. Found: C, 58.82; H, 4.69.

16F. Catalytic Reduction of 4-[4-(4-bromophenoxy)-phenylsulfonylmethyl]-tetrahydropyran-4-carboxylic acid A solution of 660 mg (1.45 mmol) of 4-[4-(4-bromophenoxy)phenylsulfonylmethyl]-tetrahydropyran-4 -carboxylic acid in 80% ethanol/tetrahydropyran (40 mL) was hydrogenated at atmospheric pressure for 14 hours using palladium on carbon catalyst, filtered over a celite pad washing with methylene chloride and concentrated in vacuo to afford 4-[4-phenoxyphenylsulfonylmethyl]-tetrahydropyran-4-carboxylic acid as a light orange solid (546 mg, 100%), which was taken directly into the next reaction without further purification: mp 162.5–165.3° C.; IR (KBr) 3431 (br), 1727 cm$^{-1}$; $^1$HNMR (DMSO-d$_6$) δ 1.67 (ddd, J=14.1, 10.0, 4.0 Hz, 2H), 1.95 (dm, J=14.1 Hz, 2H), 3.47 (m$_c$, 2H), 3.65 (m$_c$, 2H), 3.66 (s, 2H), 7.15 (d, J=8.8 Hz, 2H), 7.27 (t, J=7.4 Hz, 1H), 7.45 (t, J=7.5 Hz, 2H), 7.86 (d, J=7.9 Hz, 2H), 12.74 (s, 1H); $^{13}$C NMR (DMSO-d$_6$) δ 32.88 (t), 42.26 (s), 61.75 (t), 63.26 (t), 117.64 (d), 120.11 (d), 125.03 (d), 130.04 (d), 130.39 (s), 134.69 (s), 154.69 (s), 161.53 (s), 174.39 (s); FABHRMS Calcd for C$_{19}$H$_{21}$SO$_6$ (M$^+$+H): 377.1059. Found: 378.1064. Anal. Calcd. for C$_{19}$H$_{20}$SO$_6$.0.75H$_2$O: C, 58.52; H, 5.56. Found: C, 58.54; H, 5.19.

Example 17

Preparation of Compounds of Formula Ij

17A. Preparation of Ii where R$^1$, R$^2$ and R$^3$ are Hydrogen, and R$^4$ is Benzyl Thiophenol (80 mg) was stirred for 45 min with potassium hydride (40 mg) in N,N-dimethylformamide (1 ml) to produce a homogeneous solution of potassium thiophenolate. To this mixture was added 3-benzyl-3-(4-bromophenylsulfonyl)-propionic acid (100 mg) dissolved in N,N-dimethylformamide (1 ml) at room temperature. After stirring for 16 hours at 75° C. the mixture was partitioned between aqueous citric acid and water, giving a product which was purified by preparative TLC to afford 3-benzyl-3-(4-phenylthiophenylsulfonyl)-propionic acid (30 mg).

17B. Preparation of Ii where R$^1$, R$^2$ and R$^3$ are Hydrogen, and R$^4$ is Benzyl The 3-benzyl-3-(4-phenylthiophenylsulfonyl)-propionic acid, prepared as shown above, was then converted to 3-benzyl-3-(4-phenylthiophenylsulfonyl)-N-hydroxypropionamide as described in Example 10A.

Example 18

Preparation of Compounds of Formula Ik

18A. Preparation of Ik where R$^1$, R$^2$ and R$^3$ are Hydrogen, and R$^4$ is Benzyl A mixture of 3-benzyl-3-(4-bromophenylsulfonyl)-propionic acid (250 mg), p-methoxystyrene (0.1 ml), diisopropylethylemine (0.25 ml), palladium acetate (5 mg) and tri(o-methylphenyl)phosphine (16 mg) was stirred overnight at 80° C. The reaction mixture was dissolved in methylene chloride and washed with aqueous citric acid. Solvent was removed from the methylene chloride solution, and the residue chromatographed on silica gel (preparative TLC, eluting with 10% methanol/methylene chloride), to afford 3-benzyl-3-(4-styrylphenylsulfonyl)-propionic acid (21 mg).

18B. Preparation of Ik where R$^1$, R$^2$ and R$^3$ are Hydrogen, and R$^4$ is Benzyl The 3-benzyl-3-(4-styrylphenylsulfonyl)-propionic acid, prepared as shown above, was then converted to 3-benzyl-3-(4-styrylphenylsulfonyl)-N-hydroxypropionamide, LSIMS m/e=452.2 (M+H)$^+$, as described in Example 10A.

Example 19

Preparation of Compounds of Formula Il
Preparation of Il where n is 2, R1 and R$^2$ together with the Carbon to which they are attached are Piperidine, R$^2$ and R$^3$ are Hydrogen, and R$^5$ is 4-(4-Chlorophenoxy)phenyl Trifluoroacetic acid (4 mL) was added to a solution of N-tert-butoxy-2-[4-(4-phenoxyphenylsulfonylmethyl)-N-BOC-piperidin-4-yl]-carboxamide (2 g, 3.64 mmol) dissolved in methylene chloride (4 mL). The reaction mixture was stirred for 1.3 hours and concentrated in vacuo. The crude salt residue was dissolved in ethyl acetate (150 mL), washed with saturated aqueous sodium bicarbonate (2×50 mL), dried over magnesium sulfate, concentrated in vacuo, to afford the free base, N-tert-butoxy-2-[4-(4-phenoxyphenylsulfonylmethyl)-piperidin-4-yl]-carboxamide (1.57 g, 90%). $^1$HNMR (CDCl$_3$) δ 1.28 (s, 9H), 2.23 (m$_c$, 2H), 2.56 (m$_c$, 2H), 3.30 (m$_c$, 2H), 3.44 (m$_c$, 2H), 3.53 (m$_c$, 2H), 7.00 (d, J=8.9 Hz, 2H), 7.05 (d, J=8.8 Hz, 2H), 7.38 (d, J=8.8 Hz, 2H), 7.82 (d, J=8.8 Hz, 2H), 8.25 (br s, 1H), 8.48 (br s, 1H).

Example 20

Preparation of Compounds of Formula Im

20A. Preparation of Im where n is 2, R is Ethoxycarbonylmethyl, R$^1$ and R$^2$ are Hydrogen, and R$^5$ is 4-Phenoxyphenyl A solution of N-tert-butoxy-2-[4-(4-phenoxyphenyl-sulfonyl)-piperidin-4-yl]-acetamide (750 mg) in N,N-dimethylformamide (10 ml) was treated with ethyl bromoacetate (0.2 ml) and potassium carbonate (600 mg). The mixture was stirred overnight at room temperature, and then partitioned between ethyl acetate and water. After drying, solvent was removed from the organic layer under reduced pressure to yield N-tert-butoxy-2-[4-(4-phenoxyphenylsulfonyl)-1-(ethoxycarbonylmethyl) piperidin-4-yl]-acetamide, which was used in the next step without further purification.

20B. Preparation of Im where n is 2, R is Isopropyl, $R^1$ and $R^2$ are Hydrogen, and $R^5$ is 4-Phenoxyphenyl To a solution of N-tert-butoxy-2-[4-(4-phenoxyphenyl-sulfonyl)-piperidin-4-yl)]-acetamide (500 mg) in acetone (20 ml) was added 10% palladium on carbon (100 mg), and the mixture stirred under hydrogen for three days. The catalyst was filtered off, and solvent removed from the filtrate under reduced pressure. The residue was chromatographed on silica gel, eluting with 10% methanol/methylene chloride, to give N-t-butoxy-2-(4-(4-phenoxyphenyl-sulfonyl)-1-(isopropyl)piperidin-4-yl)]-acetamide (300 mg).

20C. Preparation of Im where n is 2, varying R

Similarly, following the procedures of Example 20A above, but replacing ethyl bromoacetate with 3-picolyl chloride, N-tert-butoxy-2-[4-(4-phenoxyphenylsulfonyl)-1-(3-picolyl)piperidin-4-yl]-acetamide was prepared.

Similarly, following the procedures of Example 20A above, but replacing N-tert-butoxy-2-[4-(4-phenoxyphenyl-sulfonyl)-piperidin-4-yl)]-acetamide with N-tert-butoxy-2-{4-[4-(4-fluorophenoxy)phenylsulfonyl]-piperidin-4-yl}-acetamide, and replacing ethyl bromoacetate with cyclopropylmethyl bromide, N-tert-butoxy-2-{4-[4-(4-fluorophenoxy)phenylsulfonyl]-1-(cyclopropylmethyl)-piperidin-4-yl}-acetamide was prepared.

Similarly, N-tert-butoxy-2-[4-(4-phenoxyphenyl-sulfonyl)-1-(acetamidocarbonylmethyl)piperidin-4-yl]-acetamide was prepared.

20D. Preparation of Im where n is 2, varying R

Similarly, following the procedures of Example 20A above, but optionally replacing N-tert-butoxy-2-[4-(4-phenoxyphenylsulfonyl)piperid-4-yl)]-acetamide with other compounds of Formula Iy, and optionally replacing ethyl bromoacetate with other compounds of formula RX, where R is lower alkyl, cycloalkylalkyl, acyl, alkoxycarbonylalkyl, picoline, —$SO_2R^a$, where $R^a$ is lower alkyl or —$NR^bR^c$, where $R^b$ and $R^c$ are independently hydrogen or lower alkyl; and the like, and X is chloro, bromo or iodo, other compounds of Formula Im were prepared:

N-tert-butoxy-2-[1-ethyl-4-(4-phenoxyphenylsulfonyl)-piperidin-4-yl]-acetamide;

N-tert-butoxy-2-[1-methyl-4-(4-phenoxyphenyl-sulfonyl)-piperidin-4-yl]-acetamide, m.p. 152–155° C.;

N-tert-butoxy-2-[1-(2-methylpropyl)-4-(4-phenoxy-phenylsulfonyl)-piperidin-4-yl]-acetamide;

N-tert-butoxy-2-[1-cyclopropylmethyl-4-(4-phenoxy-phenylsulfonyl)-piperidin-4-yl]-acetamide;

N-tert-butoxy-2-[1-cyclopropylmethyl-4-[4-(4-chlorophenoxy)-phenylsulfonyl]-piperidin-4-yl]-acetamide; and N-tert-butoxy-2-[1-acetyl-4-[4-(4-fluorophenoxy) phenylsulfonyl]-piperidin-4-yl]-acetamide.

20E. Preparation of Ic where n is 2, $R^3$ and $R^4$ are Hydrogen, $R^1$ and $R^2$ when taken together with the Carbon to which they are attached is 1-CyclopropylmethylPiperidine, and $R^5$ is 4-(4-Chlorophenoxy)phenyl To a solution of the free base N-tert-butoxy-2-[4-(4-phenoxyphenylsulfonylmethyl)-piperidin-4-yl]-carboxamide (1.28 g, 2.66 mmol) dissolved in N,N-dimethylformamide (17 mL), was added cyclopropylmethyl bromide (0.26 mL, 2.66 mmol), followed by potassium carbonate (1.84 g, 13.3 mmol). After the reaction mixture was stirred for 20 hours, water was added (100 mL), and the aqueous solution extracted with ethyl acetate (3×100 mL). The combined organic extracts were washed with brine (2×50 mL), dried over magnesium sulfate, concentrated in vacuo. Chromatography over silica gel, and eluting with 25% ethyl acetate/hexanes, gave N-tert-butoxy-2-[4-(4-phenoxyphenylsulfonylmethyl)-1-(cyclopropyl)piperidin-4-yl-carboxamide (1.30 g, 92%). $^1$HNMR (CDCl$_3$) δ 0.10 (ddd,J=5.6, 4.7, 4.6 Hz, 2H), 0.53 (ddd,J=8.7, 4.7, 4.5 Hz, 2H), 0.85 (m,, 1H), 1.31 (s, 3H), 1.64 ($m_c$, 2H), 2.06 ($m_c$, 2H), 2.24 ($m_c$, 2H), 2.28 (d, J=6.5 Hz, 2H), 2.67 ($m_c$, 4H), 3.50 ($m_c$, 2H), 7.01 (d, J=8.8 Hz, 2H), 7.04 (d, J=8.8 Hz, 2H), 7.37 (d, J=8.8 Hz, 2H), 7.85 (d, J=8.8 Hz, 2H), 8.33 (br s, 2H); FABMS (M$^+$+H): 535.2.

20F. Preparation of Ic where n is 2, $R^3$ and R4 are Hydrogen, $R^1$ and $R^2$ when taken together with the Carbon to which they are attached is 1-(3 -Picolyl) piperidine, and $R^5$ is 4-(4-Chloroahenoxy)phenyl Similarly, following the procedures of Example 20E above, but replacing cyclopropylmethyl bromide with 1.25 equivalents of 3-picolyol chloride hydrochloride, N-tert-butoxy-2-(4-(4-phenoxyphenylsulfonylmethyl)-1-(3-picolyl)piperidin-4-yl]-carboxamide was prepared: mp 83.3–93.8° C.; IR (KBr) 3436, 1661 cm$^{-1}$; $^1$HNMR (CDCl$_3$) δ 1.31 (s, 9H), 2.00 ($m_c$, 2H), 2.24 ($m_c$, 2H), 2.55 ($m_c$, 4H), 3.48 (s, 2H), 3.53 (s, 2H), 7.01 (d, J=8.9 Hz, 2H), 7.04 (d, J=8.9 Hz, 2H), 7.25 (dd, J=7.6, 4.6 Hz, 2H), 7.38 (d, J=8.8 Hz, 2H), 7.64 (brd, J=7.8 Hz, 2H), 7.85 (d, J=8.9 Hz, 2H), 8.36 (br s, 1H), 8.52 (m, 2H); FABMS (M$^+$+H): 572.0. Anal. Calcd. for $C_{29}H_{34}N_3SO_5Cl.0.5\ H_2O$: C, 59.03; H, 5.81; N, 7.12. Found: C, 59.37; H, 6.15; N, 7.98.

20G. Preparation of Ic where n is 2, $R^3$ and R4 are Hydrogen, $R^1$ and $R^2$ when taken together with the Carbon to which they are attached is 1-(Nicotinoyl)Piperidine, and $R^5$ is 4-(4-Chlorophenoxy)phenyl To a solution of the free base N-tert-butoxy-2-[4-(4-phenoxyphenylsulfonylmethyl)-piperidin-4-yl]-carboxamide (491 mg, 1.02 mmol) and N,N-diisopropylethylamine (444 mg, 2.55 mmol) in methylene chloride (2 mL) cooled to 0° C., was added nicotinyl chloride hydrochloride (219 mg, 1.27 mmol) in one portion. After the reaction mixture was stirred for 3 hours, water (30 mL) was added, and the aqueous solution extracted with ethyl acetate (2×60 mL). The combined organic extracts were washed with brine (2×50 mL), dried over magnesium sulfate, concentrated in vacuo. Chromatography over silica gel, and eluting with 6% methanol/methylene chloride, afforded N-tert-butoxy-2-[4-(4-phenoxyphenyl-sulfonylmethyl)-1-(nicotinoyl)piperidin-4-yl]-carboxamide (233 mg, 39%). $^1$HNMR (CDCl$_3$) δ 1.33 (s, 9H), 1.95 (m,, 2H), 2.35 (my, 2H), 3.45 (m., 2H), 3.49 (s, 2H), 3.55 ($m_c$, 4H), 7.01 (d, J=8.8 Hz, 2H), 7.06 (d, J=8.8 Hz, 2H), 7.39 (d, J=8.8 Hz, 2H), 7.41 ($m_c$, 2H), 7.79 ($m_c$, 2H), 7.83 (d, J=8.8 Hz, 2H), 8.69 (br s, 1H), 8.52 ($m_c$, 2H).

20H. Preparation of Ic where n is 2, $R^3$ and R4 are Hydrogen, $R^1$ and $R^2$ when taken together with the Carbon to which they are attached is 1-(Methanesulfonyl)Piperidine, and $R^5$ is 4-(4-Chlorophenoxy)Phenyl To a solution of the free base N-tert-butoxy-2-[4-(4-phenoxyphenylsulfonylmethyl)-piperidin-4-yl]-carboxamide (1.57 g, 3.26 mmol) in 67% methylene chloride/pyridine (16.5 mL) cooled to −78° C., was added a solution of methanesulfonyl chloride (0.51 mL, 6.53 mmol) in methylene chloride (2 mL). After the reaction mixture was stirred for 4 hours, 3N aqueous hydrochloric acid (25 mL) was added, and the aqueous solution extracted with ethyl acetate (2×60 mL). The combined organic extracts were washed with brine (2×50 mL), dried over magnesium sulfate, concentrated in vacuo. Chromatography over silica gel, and eluting with 45% ethyl acetate/hexanes, afforded N-tert-butoxy-2-[4-(4-phenoxyphenylsulfonylmethyl)-1-(methanesulfonyl)piperidin-4-yl]-carboxamide (1.16 g, 64%). $^1$HNMR (CDCl$_3$) δ 1.33 (s, 9H), 2.05 ($m_c$, 2H), 2.37

($m_c$, 2H), 2.79 (s, 3H), 3.23 ($m_c$, 2H), 3.43 (s, 2H), 3.47 ($m_c$, 2H), 7.01 (d, J=8.9 Hz, 2H), 7.06 (d, J=8.9 Hz, 2H), 7.39 (d, J=8.9 Hz, 2H), 7.85 (d, J=8 9 Hz, 2H); FABMS (M⁺+H): 559.1.

Example 21

Preparation of Compounds of Formula In

21A. Preparation of In where n is 2, R is Ethoxycarbonylmethyl, R¹ and R² are Hydrogen, and R⁵ is 4-Phenoxyphenyl The product from Example 20A, N-tert-butoxy-2-[4-(4-phenoxyphenylsulfonyl)-1-(ethoxycarbonylmethyl) piperidin-4-yl]-acetamide, was dissolved in dichloroethane (10 ml), cooled to 0° C., and saturated with hydrochloric acid gas. The reaction vessel was then sealed and the solution stirred for two days at 25° C. Solvent was removed from the reaction mixture under reduced pressure, and the residue purified by preparative TLC, eluting with 10% methanol/methylene chloride, to give N-hydroxy-2-[4-(4-phenoxyphenylsulfonyl)-1-(ethoxycarbonylmethyl) piperidin-4-yl]-acetamide (420 mg), m/e=477.1 (MH⁺, FABMS).

21B. Preparation of In where n is 2, R is Isopropyl, R¹ and R² are Hydrogen, and R⁵ is 4-Phenoxyphenyl The product from Example 20B, N-t-butoxy-2-[4-(4-phenoxyphenylsulfonyl)-1-(isopropyl)piperidin-4-yl)]-acetamide, was reacted with hydrochloric acid gas as described above, to yield N-hydroxy-2-[4-(4-phenoxyphenylsulfonyl)-1-(isopropyl)piperidin-4-yl)]-acetamide (155 mg), m.p. 128° C., m/e=432 (MH⁺,EIMS).

21C. Preparation of In where n is 2, varying R

Similarly, following the procedures of Example 21A above, but replacing ethyl bromoacetate with 3-picolyl chloride, N-hydroxy-2-[4-(4-phenoxyphenylsulfonyl)-1-(3-picolyl)piperidin-4-yl]-acetamide was prepared, m.p. 185–192° C. (dec).

Similarly, following the procedures of Example 19A above, but replacing N-tert-butoxy-2-[4-(4-phenoxyphenylsulfonyl)-piperidin-4-yl)]-acetamide with N-tert-butoxy-2-{4-(4-(4-fluorophenoxy)phenylsulfonyl]-piperidin-4-yl}-acetamide, and replacing ethyl bromoacetate with cyclopropylmethyl bromide, N-hydroxy-2-(4-[4-(4-fluorophenoxy)phenylsulfonyl]-1-cyclopropylmethyl-piperidin-4-yl)-acetamide was prepared, m.p. 104–105° C.

Similarly, N-hydroxy-2-[4-(4-phenoxyphenylsulfonyl)-1-acetamidocarbonylmethylpiperidin-4-yl]-acetamide was prepared.

21D. Preparation of In where n is 2, varying R

Similarly, following the procedures of Example 21A above, but optionally replacing N-tert-butoxy-2-[4-(4-phenoxyphenylsulfonyl)-piperid-4-yl)]-acetamide with other compounds of Formula Iy, and optionally replacing ethyl bromoacetate with other compounds of formula RX, where R is lower alkyl, cycloalkylalkyl, acyl, alkoxycarbonylalkyl, picoline, —SO₂Rᵃ, where Rᵃ is lower alkyl or —NRᵇRᶜ, where Rᵇ and Rᶜ are independently hydrogen or lower alkyl; and the like, and X is chloro, bromo or iodo, other compounds of Formula In were prepared:

2-[1-ethyl-4-(4-phenoxyphenylsulfonyl)-piperidin-4-yl]-N-hydroxyacetamide, m.p. 182–183° C.;

N-hydroxy-2-[1-methyl-4-(4-phenoxyphenylsulfonyl)-piperidin-4-yl]-acetamide, m.p. 152–155° C.;

N-hydroxy-2-[1-(2-methylpropyl)-4-(4-phenoxyphenylsulfonyl)-piperid-4-yl]-acetamide, m.p. 226–227° C.;

2-[1-cyclopropylmethyl-4-(4-phenoxyphenylsulfonyl)-piperidin-4-yl]-acetamide, m.p. 210–211° C.;

2-[1-cyclopropylmethyl-4-[4-(4-chlorophenoxy)-phenylsulfonyl]-piperidin-4-yl]-N-hydroxyacetamide, m.p. 110–112° C.; and 2-[1-acetyl-4-(4-(4-fluorophenoxy)phenylsulfonyl]-piperidin-4-yl]-N-hydroxyacetamide, m/e=450 (NH₄).

Example 22

Preparation of Compounds of Formula Iab

Preparation of Iab where R5 is 4-phenoxyphenyl

4-Phenoxythiophenol (4.8 g) was stirred for 45 min with potassium hydride (0.98 g) in N,N-dimethylformamide (100 ml) to produce a homogeneous solution of potassium 4-phenoxythiophenolate. The lactone, (S)-3-carbobenzyl-oxyamino-2-oxetanone (5.3 g) (Arnold, L. D. et al., J. Am. Chem. Soc., 107, 7105 (1985)), dissolved in N,N-dimethylformamide (50 ml) was then added at room temperature. After stirring for 30 minutes the mixture was poured into water and extracted with ethyl acetate. The combined extracts were dried over magnesium sulfate, and solvent removed under reduced pressure to give (R)-2-(benzyloxycarbonylamino)-3-(4-phenoxyphenylthio)-propionic acid (9.2 g). It can be used directly in the next step.

Example 23

Preparation of Compounds of Formula Io

Preparation of Io where R⁵ is 4-phenoxyphenyl

The above-prepared (R)-2-(benzyloxycarbonylamino)-3-(4-phenoxyphenylthio)-propionic acid was dissolved in methylene chloride (175 ml), cooled to 0° C., and treated with O-(tert-butyl)hydroxylamine hydrochloride (7.7 g), 4-methylmorpholine (9.4 ml), 1-hydroxybenzotriazole (2.8 g), and N-ethyl-N'-(3-dimethylaminopropyl)-carbodiimide (7.9 g). The mixture was allowed to warm to room temperature, stirred for 1.5 hours, then partitioned between methylene chloride and water. Solvent was removed from the organic phase under reduced pressure, and the residue purified by flash chromatography on silica gel, eluting with 0 to 50% ethyl acetate/hexane, to provide (R)-2-(benzyloxycarbonylamino)-N-tert-butoxy-3-(4-phenoxyphenylthio)-propionamide (7.4 g) as a white foam.

Example 24

Preparation of Compounds of Formula Ip

Preparation of Is where n is 2 and R⁵ is 4-phenoxyphenyl (R)-N-tert-butoxy-2-(benzyloxycarbonylamino)-3-(4-phenoxyphenylthio)-propionamide (1.5 mmol) was dissolved in methanol (140 ml), and a solution of OXONE (15 g) in water (50 ml) was added with vigorous stirring. The oxidation is usually complete within 2 hours. The mixture is then partitioned between methylene chloride and water. Solvent was removed from the dried organic phase under reduced pressure, to afford (R)-2-(benzyloxycarbonylamino)-N-tert-butoxy-3-(4-phenoxyphenylsulfonyl)-propionamide (8.3 g) in near-quantitative yield.

Example 25

Preparation of Compounds of Formula Iq

Preparation of Iq where n is 2, R¹ is Hydrogen, R² is —NR⁶R⁷, in which R⁶ is Hydrogen and R⁷ is Benzyloxycarbonylamino, and R⁵ is 4-phenoxyphenyl A solution of (R)-2-(benzyloxycarbonylamino)-N-tert-butoxy-3-(4-phenoxyphenylsulfonyl)-propionamide (1.2 g) obtained from Example 16 in methylene chloride (5 ml) was diluted with trifluoroacetic acid (30 ml). The solution was allowed to stand overnight, and solvent was removed under reduced pressure. This residue was chromatographed on silica gel, eluting with 10% methanol/methylene chloride to give (R)-2-(benzyloxycarbonylamino)-N-hydroxy-3-(4-phenoxyphenylsulfonyl)-propionamide (400 mg), m.p. 195–202° C.

Example 26

Preparation of Compounds of Formula Ir
Preparation of Ir where n is 2 and $R^5$ is 4-phenoxyphenyl
(R)-2-(benzyloxycarbonylamino)-N-tert-butoxy-3-(4-phenoxyphenylsulfonyl)-propionamide (6.0 g) obtained from Example 17 was dissolved in ethanol (100 ml) and hydrogenated at 1 atmosphere in the presence of 10% palladium on carbon (6 g) for a period of 18 hours. The catalyst was filtered off and the solvent removed from the filtrate under reduced pressure to give (R)-2-amino-N-tert-butoxy-3-(4-phenoxyphenylsulfonyl)-propionamide as a glass.

Example 27

Preparation of Compounds of Formula Is
Preparation of Is where n is 2, R is Hydrogen, $R^2$ is —$NR^6R^7$, in which $R^6$ and $R^7$ are both Hydrogen, and $R^5$ is 4-phenoxyphenyl
Similarly as in Example 25, (R)-2-amino-N-tert-butoxy-3-(4-phenoxyphenylsulfonyl)-propionamide (6.0 g) was dissolved in 1,2-dichloroethane (5 ml) and cooled to -20° C. and bubbled for 20 minutes with hydrochloric acid gas in a pressure tube. The flask was then sealed and the mixture stirred overnight. The tube was cooled, vented, and allowed to warm. The solution was rinsed with methanol, the solvent removed from the filtrate under reduced pressure, triturated with 1:1 hexane/ethyl acetate (4 ml). The residue was filtered and dried to give (R)-2 -amino-N-hydroxy-3-(4-phenoxyphenylsulfonyl)-propionamide hydrochloride, m.p. 178–180° C. (dec).

Example 28

Preparation of Compounds of Formula It
Preparation of It where n is 2, $R^1$ is Hydrogen, $R^2$ is —$NR^6R^7$, in which $R^6$ is Hydrogen and $R^7$ is CBZ-(S)-Valinamido, and $R^5$ is 4-phenoxyphenyl
To a solution of (R)-2-amino-N-tert-butoxy-3-(4-phenoxyphenylsulfonyl)-propionamide (1.9 g) in methylene chloride (30 ml) was added CBZ-(S)-valine (1.6 g), 1-hydroxybenzotriazole (0.9 g), triethylamine (1 ml), and N'-ethyl-N'-(3-dimethylaminopropyl)-carbodiimide (1.3 g). After stirring overnight at room temperature, the solution was partitioned between methylene chloride and water, and after the organic layer was dried over magnesium sulfate, solvent was removed under reduced pressure to give (R)-N-tert-butoxy-2-(CBZ-valinamido)-3-(4-phenoxyphenylsulfonyl)-propionamide, which was used without further purification.

Example 29

Preparation of Compounds of Formula Iu
Preparation of Iu where n is 2, $R^1$ is Hydrogen, $R^2$ is —$NR^6R^7$, in which $R^6$ is Hydrogen and $R^7$ is (S)-Valinamido, and $R^5$ is 4-phenoxyphenyl
A solution of (R)-N-tert-butoxy-2-(CBZ-valinamido)-3-(4-phenoxyphenylsulfonyl)-propionamide (prepared above) in a mixture of methanol (300 ml) and ethanol (100 ml) was stirred under hydrogen at 1 atmosphere with palladium on carbon catalyst (10% Pd, 4 g) for 3 hours. The mixture was filtered, and the filtrate evaporated under reduced pressure. The residue was chromatographed on silica gel, eluting with 0–3% methanol in methylene chloride, to give (R)-N-tert-butoxy-2-valinamido-3-(4-phenoxyphenylsulfonyl)-propionamide (1.6 g).

Example 30

Preparation of Compounds of Formula Iv
Preparation of Iv where n is 2, $R^1$ is Hydrogen, $R^2$ is —$NR^6R^7$, in which $R^6$ is Hydrogen and $R^7$ is (S)-Valinamido, and $R^5$ is 4-phenoxyphenyl
A solution of (R)-N-tert-butoxy-2-valinamido-3-(4-phenoxyphenylsulfonyl)-propionamide (1.6 g) in 1,2-dichloroethane (50 ml) was cooled to -20° C. and bubbled for 15–20 minutes with hydrochloric acid gas in a pressure tube. The flask was then sealed and the mixture stirred for 24 hours. After cooling the tube was cautiously vented and its contents evaporated to yield a gum, which upon trituration with ethyl acetate gave a crude product as a white powder. This product was stirred overnight with 10% methanol/methylene chloride (20 ml) and filtered to remove impurities. This was repeated three times to give (R)-N-hydroxy-2-valinamido-3-(4-phenoxyphenylsulfonyl)-propionamide hydrochloride (760 mg), m.p. 214–217° C.

Example 31

Preparation of Compounds of Formula Iw
Preparation of Iw where n is 2, Y is hydroxy or lower alkoxy, $R^1$ and $R^2$ when taken together with the carbon to which they are attached are Tetrahydropyan-4-yl, $R^3$ is hydrogen, and $R^4$ is Benzyl, and $R^5$ is 4-(4-Chlorophenoxy)phenyl
1. To a solution of 4-[4-(4-chlorophenoxy) phenylthiomethyl]-tetrahydropyran-4-carboxylic acid methyl ester in 20% tetrahydrofuranmethanol (9.5 mL) was added dropwise a solution of OXONE (1.53 g, 2.49 mmol) in water (8 mL) while maintaining an internal temperature of 15–20° C. The mixture was stirred 2 hours and the mixture dissolved in 40% ethyl acetate/water (200 mL). The layers were partitioned, and the water layer back extracted using ethyl acetate (2×50 mL). The combined organic layers were dried over magnesium sulfate, concentrated, and the residue purified by preparative chromatography (20×40–1000 um plates), eluting with 50% ethyl acetate/hexanes) to afford 4-[4-(4-chlorophenoxy)phenylsulfonylmethyl]-tetrahydropyran-4-carboxylic acid methyl ester (460 mg, 71%). $^1$HNMR (CDCl$_3$) δ 1.71–1.82 (m, 2H), 2.23 (dm, J=13.6 Hz, 2H), 3.47 (s, 2H), 3.58–3.67 (m, 2H), 3.59 (s, 3H), 3.73–3.81 (m, 2H), 6.97–7.10 (m, 4H), 7.39 (d, J=8.7 Hz, 2H), 7.84 (d, J=8.7 Hz, 2H).
2. Lithium diisopropylamide was prepared by the addition of 2.5M N-butyl lithium (610 μL, 1.53 mmol) in hexanes to a solution of diisopropylamine (200 μL, 1.53 mmol) in tetrahydrofuran (3 mL) at 0° C. and stirring for 20 minutes. Then a solution of 4-[4-(4-chlorophenoxy) phenylsulfonylmethyl]-tetrahydropyran-4-carboxylic acid methyl ester (540 mg, 1.27 mmol) in tetrahydrofuran (1 mL) was added to the solution of lithium diisopropylamide at −78° C., and stirred for an additional 60 minutes. Benzyl bromide (181 μL, 1.53 mmol) of was added to the mixture, stirred for an 50 minutes, warmed to room temperature over 30 minutes, and stirred for an additional 3 hours. The mixture was then diluted with 0.1M aqueous hydrochloric acid (25 mL) and extracted with methylene chloride (2×50 mL). The combined organic layers were dried over magnesium sulfate, concentrated in vacuo, chromatographed over silica gel, eluted with 20% ethyl acetate/hexanes, to afford 3-benzyl-4-[4-(4-chlorophenoxy)phenylsulfonylmethyl]-tetrahydropyran-4-carboxylic acid methyl ester (440 mg, 67%). IR (KBr) 1736 cm$^{-1}$; $^1$HNMR (CDCl$_3$) δ 1.78 (dm, J=13.5 Hz, 1H), 2.02–2.17 (m, 2H), 2.39 (dm, J=13.5 Hz, 1H), 3.19–3.23 (m, 2H), 3.37–3.45 (td, J=11.9, 2.4 Hz, 2H), 3.77–3.85 (m, 1H), 3.84 (s, 3H), 3.88–3.98 (m, 2H), 4.07–4.17 (m, 2H), 6.83–6.90 (m, 4H), 6.94 (d, J=8.7 Hz, 2H), 7.08–7.15 (m, 3H), 7.37 (d, J=8.7 Hz, 2H), 7.62 (d, J=8.7 Hz, 2H); FABMS (M$^+$+H): 515.

Example 32

Preparation of Compounds of Formula Ix

Preparation of Ix where n is 2, Y is hydroxy, R$^1$ and R$^2$ when taken together with the carbon to which they are attached are Tetrahydropyan-4-yl, R$^3$ is hydrogen, and R$^4$ is Benzyl, and R$^5$ is 4-(4-Chlorophenoxy)phenyl To a solution of 3-benzyl-4-[4-(4-chlorophenoxy)-phenylsulfonylmethyl]-tetrahydropyran-4-carboxylic acid methyl ester (410 mg, 0.80 mmol) in N,N-dimethylformamide (4 mL) was added lithium iodide (1.06 g, 7.96 mmol), followed by sodium cyanide (78 mg, 1.59 mmol). The mixture was heated to 120° C. for 8 hours, cooled to room temperature, the N,N-dimethylformamide solvent removed by heating under reduced pressure, and the residue partitioned between ethyl acetate (150 mL) and saturated aqueous sodium bisulfite (50 mL). The ethyl acetate layer was dried over magnesium sulfate, concentrated in vacuo, purified by preparative chromatography (20×40–1000 um plates), eluted with 8% methanol/methylene chloride) to afford 317 mg (80%) of 3-benzyl-4-[4-(4-chlorophenoxy)-phenylsulfonylmethyl]-tetrahydropyran-4-carboxylic acid $^1$HNMR (N,N-dimethylformamide contaminant, CDCl$_3$) δ 1.74 (dm, J=13.5 Hz, 1H), 2.05–2.18 (m, 2H), 2.42 (dm, J=13.5 Hz, 1H), 3.22–3.26 (m, 2H), 3.48–3.58 (m, 2H), 3.78–4.18 (m, 5H), 6.83–6.88 (m, 4H), 6.93 (d, J=8.5 Hz, 2H), 7.08–7.13 (m, 3H), 7.36 (d, J=8.7 Hz, 2H), 7.62 (d, J=8.7 Hz, 2H); CIMS (NH$_3$, M$^+$+NH$_4$+): 518.

Example 33

Preparation of Compounds of Formula I

Preparation of I where n is 2, R$^2$ is —NR$^6$R$^7$, in which R$^6$ and R$^7$ are both Methyl, and R$^5$ is 4-phenoxyphenyl To a solution of (R)-2-amino-N-tert-butoxy-3-(4-phenoxyphenylsulfonyl)-propionamide (1.6 g) in N,N-dimethylformamide (5 ml) was added potassium carbonate (0.5 g) and methyl iodide (550 μl). After stirring for 2.5 hours, the mixture was partitioned between ethyl acetate and water, and after the organic layer was dried over magnesium sulfate, solvent was removed under reduced pressure. The residue was chromatographed on silica gel, eluting with 50% ethyl acetate/hexane to give (R)-N-tert-butoxy-2-dimethylamino-3-(4-phenoxyphenylsulfonyl)-propionamide (0.6 g).

This compound, (R)-N-tert-butoxy-2-dimethylamino-3-(4-phenoxyphenylsulfonyl)-propionamide, was dissolved in 1,2-dichloroethane (50 ml), cooled to −30° C. and bubbled for 15–20 minutes with hydrochloric acid gas in a pressure tube. The flask was then sealed and the mixture stirred overnight. After cooling the tube was cautiously vented and its contents evaporated, to yield a gum, which upon trituration with 2:1 hexane/ethyl acetate gave a white powder, (R)-2-dimethylamino-N-hydroxy-3-(4-phenoxyphenyl-sulfonyl)-propionamide hydrochloride (0.43 g), m.p. 65–70° C.

Example 34

Preparation of Compounds of Formula I

Preparation of I where n is 2, R$^2$ is —NR$^6$R$^7$, in which R$^6$ is Hydrogen and R$^7$ is Dimethylaminosulfonyl, and R$^5$ is 4-phenoxyphenyl To a solution of (R)-2-amino-N-tert-butoxy-3-(4-phenoxyphenylsulfonyl)-propionamide (1.5 g) in methylene chloride (20 ml) and pyridine (1.2 ml) was added dimethylsulfamoyl chloride (1 ml), and the mixture stirred overnight at room temperature. The mixture was partitioned between methylene chloride and water, and after the organic layer was dried over magnesium sulfate, solvent was removed under reduced pressure. The residue was chromatographed on silica gel, eluting with 0–45% ethyl acetate/hexane, to give (R)-N-tert-butoxy-2-dimethylamino-sulfonamido-3-(4-phenoxyphenylsulfonyl)-propionamide (1.6 g).

This compound, (R)-N-tert-butoxy-2-dimethyl-aminosulfonamido-3-(4-phenoxyphenylsulfonyl)-propionamide, was dissolved in trifluoroacetic acid (30 ml) and the mixture stirred overnight at room temperature. The trifluoroacetic acid was removed under reduced pressure, and the residue chromatographed on silica gel, eluting with 10% methanol/methylene chloride, to give (R)-2-dimethylaminosulfonamido-3-(4-phenoxyphenylsulfonyl)-N-hydroxypropionamide hydrochloride (550 mg). PMR (d6-DMSO) 7.90 (d,2H), 7.47 (d,2H), 7.25 (t,1H), 7.13 (m,4H), 3.95 (m,1H), 3.55 (m,2H), 2.6 (s,6H).

Example 35

Example of Preparation of Compounds of Formula I on a Large Scale

Preparation of I where n is 2, R$^1$ and R$^2$ when taken together with the Carbon to which they are attached represent Tetrahydropyran, R$^3$ and R$^4$ are Hydrogen, and R$^5$ is 4-(4-Chlorophenoxy)phenyl 1. Preparation of a Compound of Formula (7a)

To a mixture of N,N-dimethylformamide (56 Kg) and diethyl malonate (22 Kg) was added a 21% solution of sodium ethoxide in ethanol (45 Kg), followed by 2-chloroethyl ether (19 Kg). The mixture was heated to 85° C., causing ethanol to distil from the mixture. The temperature was raised to 120° C. until all the ethanol formed was removed (3 hours), and then the mixture was allowed to cool to 25° C. The mixture was then rewarmed to 120° C. and a further 45 Kg of a 21% solution of sodium ethoxide in ethanol added at such a rate as to cause the ethanol formed to distil off. When the distillation was complete, the mixture was cooled to 100° C., and after it was determined that the reaction was complete then cooled to 25° C. The mixture was partitioned between toluene (80 Kg) and water (216 Kg) and solvent removed from the organic layer by distillation. The product was used in the next step with no further purification.

2. Preparation of a Compound of Formula (8a) where R$^1$ and R$^2$ when taken together with the Carbon Atom to which they are attached represent Tetrahydropyran A solution of diethyl tetrahydro-4H-pyran-4,4-dicarboxylate, the compound of Formula (7a), (12 Kg) in toluene (104 Kg) was cooled to between −30° C. to −35° C., and diisobutylaluminum hydride (69 Kg) was added at such a rate so as to maintain a reaction temperature of −25° C. After the addition was complete, the temperature was raised to 15° C. over 3 hours, and the reaction stirred until all starting material was consumed. The mixture was then recooled to −15° C. and allowed to stand overnight. The product was partitioned between ethyl acetate (54 Kg), ethanol (48 Kg), and saturated sodium sulfate solution (60 liters), and the mixture stirred overnight at 250C. The precipitated salts were filtered off, washed with tetrahydrofuran, and the filtrate washed with brine and separated. The organic layer was dried over magnesium sulfate and solvent removed under reduced pressure, to give ethyl 4-hydroxymethyltetrahydropyran-4-carboxylate (3.8 Kg), the compound of Formula (8a).

3. Preparation of a Compound of Formula (9a) where $R^1$ and $R^2$ when taken together with the Carbon Atom to which they are attached represent Tetrahydropyran To a solution of lithium hydroxide monohydrate (4.46 Kg) in methanol (44 liters) and water (11 Kg) was added ethyl 4-hydroxymethyl-tetrahydropyran-4-carboxylate (8.0 Kg) The mixture was refluxed for 30 minutes, then solvent removed under reduced pressure. The mixture was cooled to 20° C., methyl tert-butyl ether (14.8 Kg) added, stirred for 10 minutes, and allowed to settle. The top organic layer was separated. This was repeated twice more, then the remaining mixture cooled to –10° C., and a solution of 31% hydrochloric acid (13 Kg) in water (3 Kg) added, maintaining the temperature below 5° C. The mixture was extracted several times with tetrahydrofuran, and the combined organic phases dried over magnesium sulfate. Approximately 90% of the tetrahydrofuran was removed, and the remaining solution added to a mixture of hexane (64.5 Kg) and methyl tert-butylether (23.7 Kg) with stirring. The precipitated solid material was filtered off and dried under reduced pressure at 60° C., to give 4-hydroxymethyl-tetrahydropyran-4-carboxylic acid (3.7 Kg), the compound of Formula (9a).

4. Preparation of a Compound of Formula Ia where $R^1$ and $R^2$ when taken together with the Carbon Atom to which they are attached represent Tetrahydropyran To a mixture of 4-hydroxymethyl-tetrahydropyran-4-carboxylic acid (3.84 Kg), 4-dimethylaminopyridine (0.6 Kg) in dichloromethane (32 liters) was added triethylamine (4.88 Kg). The mixture was cooled to –20° C., and a solution of benzenesulfonyl chloride (4.66 Kg) in dichloromethane (5 liters) was added over a period of 35 minutes, maintaining the temperature below –10° C. The mixture was stirred at –10° C. for 30 minutes, then 3N hydrochloric acid (10 liters) and water (10 liters) were added with stirring, then the layers allowed to separate. The organic layer was separated, the aqueous layer washed with dichloromethane (16 liters), the combined organics washed with aqueous 5% sodium bicarbonate solution (12 liters), then with water (12 liters), and solvent removed under reduced pressure, to give 2,7-dioxaspiro[3,5]nonane-1-one, a compound of Formula (10a)

To a mixture of 60% sodium hydride (0.92 Kg) in tetrahydrofran (26 liters) at 0° C. was added a solution of 4-(4-chlorophenoxy)thiophenol (4.37 Kg) in tetrahydrofuran (15 liters), maintaining the temperature below 10° C. The mixture was allowed to warm to room temperature for 30 minutes, then recooled to 0° C. The concentrated solution of 2,7-dioxaspiro[3,5]nonane-1-one obtained above was then added slowly to this mixture, maintaining the temperature below 10° C. The mixture was allowed to warm to room temperature, and stirred for 30 minutes. The mixture was then treated with 3N hydrochloric acid (16 liters) and dichloromethane (30 liters). The organic layer was separated and the aqueous layer extracted twice with dichloromethane (20 liters). The combined organics were washed with water (20 liters), filtered, and 100 liters of solvent removed under atmospheric pressure. To the remaining reaction product was added acetonitrile (60 liters) and after a further 60 liters of solvent were removed by distillation, acetonitrile (40 liters) was added and the total volume of the remainder reduced to 30 liters by distillation. This mixture was then heated to mild reflux (80° C.), and then slowly cooled to 0° C. The product was filtered off, washed with hexane, and dried to about 60° C. under reduced pressure, to yield 4-[4-(4-chlorophenoxy)phenylthiomethyl]tetrahydropyran-4-carboxylic acid (5.61 Kg).

5. Preparation of a Compound of Formula Iba where $R^1$ and $R^2$ when taken together with the Carbon Atom to which they are attached represent Tetrahydropyran A solution of 4-[4-(4-chlorophenoxy)phenylthiomethylltetrahydropyran-4-carboxylic acid (5.5 Kg) and N,N-dimethylformamide (27 ml) in dichloromethane (27.5 liters) was cooled to 5° C., and oxalyl chloride (1.4 liters) added slowly with stirring. After addition was complete, the mixture was allowed to warm to room temperature and stirred for 2 hours, thus forming a compound of Formula (12). The solution was then recooled to 10° C., and a mixture of 50% aqueous hydroxylamine (5.4 liters), tert-butanol (12.1 liters) and tetrahydrofuran (30.5 liters) was added slowly, maintaining the temperature below 21° C. The mixture was then allowed to warm to room temperature until the reaction was complete. The solvent was then evaporated under reduced pressure until 90% had been removed, at which point acetonitrile (42.5 liters) was added and the remaining dichloromethane removed by distillation under reduced pressure. The remaining solution was heated under reflux, and water (126 Kg) added at such a rate so as to maintain reflux. The solution was then cooled to 5° C. for 12 hours, and the solid thus obtained filtered off. This product was washed with water and dried under vacuum at 50° C. to yield 4-[4-(4-chlorophenoxy)phenylthiomethyl] tetrahydropyran-4-(N-hydroxycarboxamide) (5.06 Kg), a compound of Formula Iba.

6. Preparation of a Compound of Formula Id where $R^1$ and $R^2$ when taken together with the Carbon Atom to which they are attached represent Tetrahydropyran To a solution of 4-[4-(4-chlorophenoxy)phenylthiomethyl]-tetrahydropyran-4-(N-hydroxycarboxamide) (5.06 Kg) in tetrahydrofuran (28 liters) and methanol (112 liters) at 15° C. was added a solution of OXONE (14.23 Kg) in water (72 liters) with stirring, ensuring that the temperature did not exceed 16° C. After the addition was complete, the temperature was raised to 20° C. and the mixture stirred for 3 hours, then poured into a cold mixture (5° C.) of toluene (60 liters) and ethyl acetate (98 liters) with stirring. The resultant mixture was filtered, the organic and aqueous layers thus obtained separated, and the aqueous layer washed with a mixture of ethyl acetate (25 liters) and toluene (10 liters). This wash was repeated twice more. The combined extracts and organic layer was washed twice with water (25 liters), and solvent removed under reduced pressure to a volume of 30 liters. The solution was cooled to 5° C., and the solid filtered off, washed with ethyl acetate/water and dried under vacuum at 50° C., to yield 4-(4-(4-chlorophenoxy)phenylsulfonylmethyl]-tetrahydropyran-4-(N-hydroxycarboxamide) (4.3 Kg).

7. Similarly other Compounds of Formula I may be prepared.

Example 36

This example illustrates the preparation of representative pharmaceutical compositions for oral administration containing a compound of Formula I, or a pharmaceutically acceptable salt thereof, e.g., N-hydroxy-2-[4-(4-phenoxyphenylsulfonyl)-piperidin-4-yl)]-acetamide:

| A. Ingredients | % wt./wt. |
| --- | --- |
| Compound of Formula I | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./wt. |
| --- | --- |
| Compound of Formula I | 20.0% |
| Magnesium stearate | 0.9% |
| Starch | 8.6% |
| Lactose | 79.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tablet machine.

| C. Ingredients | |
| --- | --- |
| Compound of Formula I | 0.1 g |
| Propylene glycol | 20.0 g |
| Polyethylene glycol 400 | 20.0 g |
| Polysorbate 80 | 1.0 g |
| Water | q.s. 100 mL |

The compound of Formula I is dissolved in propylene glycol, polyethylene glycol 400 and polysorbate 80. A sufficient quantity of water is then added with stirring to provide 100 mL of the solution which is filtered and bottled.

| D. Ingredients | % wt./wt. |
| --- | --- |
| Compound of Formula I | 20.0% |
| Peanut Oil | 78.0% |
| Span 60 | 2.0% |

The above ingredients are melted, mixed and filled into soft elastic capsules.

Example 37

This example illustrates the preparation of a representative pharmaceutical formulation for parenteral administration containing a compound of Formula I, or a pharmaceutically acceptable salt thereof, e.g., N-hydroxy-2-[4-(4-phenoxyphenylsulfonyl)-piperidin-4-yl)]-acetamide:

| Ingredients | |
| --- | --- |
| Compound of Formula I | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of Formula I is dissolved in propylene glycol, polyethylene glycol 400 and polysorbate 80. A sufficient quantity of 0.9% saline solution is then added with stirring to provide 100 mL of the I.V. solution which is filtered through a 0.2μ membrane filter and packaged under sterile conditions.

Example 38

This example illustrates the preparation of a representative pharmaceutical composition in suppository form containing a compound of Formula I, or a pharmaceutically acceptable salt thereof, e.g., N-hydroxy-2-[4-(4-phenoxyphenylsulfonyl)-piperidin-4-yl)]-acetamide:

| Ingredients | % wt./wt. |
| --- | --- |
| Compound of Formula I | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 39

This example illustrates the preparation of a representative pharmaceutical formulation for insufflation containing a compound of Formula I, or a pharmaceutically acceptable salt thereof, e.g., N-hydroxy-2-[4-(4-phenoxyphenylsulfonyl)-piperidin-4-yl)]-acetamide

| Ingredients | % wt./wt. |
| --- | --- |
| Micronized compound of Formula I | 1.0% |
| Micronized lactose | 99.0% |

The ingredients are milled, mixed, and packaged in an insufflator equipped with a dosing pump.

Example 40

This example illustrates the preparation of a representative pharmaceutical formulation in nebulized form containing a compound of Formula I, or a pharmaceutically acceptable salt thereof, e.g., N-hydroxy-2-[4-(4-phenoxyphenylsulfonyl)-piperidin-4-yl)]-acetamide:

| Ingredients | % wt./wt. |
| --- | --- |
| Compound of Formula I | 0.005% |
| Water | 89.995% |
| Ethanol | 10.000% |

The compound of Formula I is dissolved in ethanol and blended with water. The formulation is then packaged in a nebulizer equipped with a dosing pump.

Example 41

This example illustrates the preparation of a representative pharmaceutical formulation in aerosol form containing a compound of Formula I, or a pharmaceutically acceptable salt thereof, e.g., N-hydroxy-2-[4-(4-phenoxyphenylsulfonyl)-piperidin-4-yl)]-acetamide:

| Ingredients | % wt./wt. |
| --- | --- |
| Compound of Formula I | 0.10% |
| Propellant 11/12 | 98.90% |
| Oleic acid | 1.00% |

The compound of Formula I is dispersed in oleic acid and the propellants. The resulting mixture is then poured into an aerosol container fitted with a metering valve.

Example 42

In Vitro Assay

42A. Isolation of MMPs for Assays

The catalytic domain of human collagenase-1 was expressed as a fusion protein with ubiquitin in *E. Coli* (Gehring, E. R. et al., *J. Biol. Chem.*, 270, 22507, (1995)). After purification of the fusion protein, the fibroblast collagenase-1 catalytic domain was released by treatment with 1 mM of aminophenylmercuric acetate (APMA) for 1 hour at 37° C. and purified by zinc chelate chromatography.

Human collagenase-2 and gelatinase B were isolated in active form from buffy coats (Mookhtiar, K. A. et al., *Biochemistry*, 29, 10620, (1990)).

The propeptide and catalytic domain portion of human collagenase-3 was expressed in *E. Coli* as an N-terminal fusion protein with ubiquitin. After purification, the catalytic domain was obtained by treatment with 1 mM APMA for 1 hour at 37° C., and purified by zinc chelate chromatography.

Rat collagenase-3 was purified in active form from the culture media of uterine smooth muscle cells (Roswit, W. T. et al., *Arch. Biochem. Biophys.*, 225, 285–295 (1983)).

The catalytic and fibronectin-like portion of human progelatinase A was expressed as a fusion protein with ubiquitin in *E. Coli*. Assays were carried out on autolytically activated material. Rat progelatinase A was purified from the culture media of interleukin-1 stimulated keratinocytes and activated by treatment with 1 mM APMA for 1 hour at 37° C., and subsequently dialyzed to remove excess APMA.

Human prostromelysin-1 was purified from the culture medium of synovial fibroblasts by affinity chromatography using an immobilized monoclonal antibody. The zymogen was activated by treatment with trypsin (1.5 µg/ml) for 1 hour at 23° C. to give a mixture of 45 and 28 kD species. The catalytic domain of human stromelysin was prepared by expression and purification of prostromelysin-1 from *E. Coli* and activated with 1 mM APMA for 1 hour at 37° C., followed by dialysis. Rat prostromelysin-1 was expressed in Chinese Hampster Ovary cells and purified from the culture media. It was activated by 1 mM APMA for 1 hour at 37° C., followed by dialysis.

Human promatrilysin was expressed and purified from Chinese Hampster Ovary cells (Barnett, J. et al., *Prot. Expres. Pur*, 5, 27, (1994)). The zymogen was activated by treatment with 1 mM APMA for 1 hour at 37° C., and purified by zinc chelate chromatography.

Compounds of Formula I exhibited the ability to inhibit the collagenases when tested in this assay.

42B. In Vitro Assay Procedure

Assays were performed in assay buffer (50 mM Tricine pH 7.5, 200 mM sodium chloride, 10 mM calcium chloride, 0.005% Brij-35) containing 2.5% methyl sulfoxide (DMSO) once the substrate and inhibitor were diluted into it. Stock solutions of inhibitors were prepared in 100% DMSO. Stock solutions of the substrate were prepared in 100% DMSO at a concentration of 2 mM.

The assay method was based on the hydrolysis of MCA-Pro-Leu-Gly-Leu-DPA-Ala-Arg-$NH_2$ (Bachem, Inc.) at 37° C. (Knight, C. G. et al., *FEBS*, 296, 263–266 (1992)). The fluorescence changes were monitored with a Perkin-Elmer LS-50B fluorimeter using an excitation wavelength of 328 nm and an emission wavelength of 393 nm. The substrate concentration used in the assays was 10 pmole. The inhibitor was diluted into the assays from a solution in 100% DMSO, and controls substituted an equal volume of DMSO so that the final DMSO concentration from inhibitor and substrate dilutions in all assays was 2.5%. The inhibition results are expressed as the inhibitor concentration that produced 50% inhibition ($IC_{50}$) of the activity in the control (non-inhibited) reaction.

Example 43

In Vitro Assay

This assay determines the ability of the compounds of Formula I to inhibit the degradation of the collagen matrix (as judged by release of hydroxyproline), and proteoglycan (as judged by the release of 35S-labelled glycosaminoglycans) from cartilage explants.

Small cartilage explants (3 mm diameter) were prepared from freshly sacrificed bovine knee joints and labeled with $^{35}SO_4$. $^{35}$S-labelled glycosaminoglycans (GAG's) and collagen fragments are released into the culture medium in response to the addition of rhIL-1-alpha, which induces the expression of chondrocyte matrix metalloproteases (MMP's), including stromelysin and collagenase. The percent inhibition of hydroxyproline and GAG's released was corrected for spontaneous release in the absence of rhIL-1-alpha.

Compounds of Formula I, when tested in this assay, displayed the ability to inhibit the release of both collagen fragments and $^{35}$S-labelled GAG's from cartilage explants.

Example 44

In Vivo Assay

The cartilage plug implantation assay measures the destruction of the collagen matrix of a cartilage plug implanted in a rat (Bishop, J. et al., *J. Phazm. Tox. Methods*, 30, 19, (1993)).

Previously frozen bovine nasal cartilage plugs weighing approximately 20 mg were embedded in polyvinyl sponges impregnated with Mycobacterium tuberculosis and implanted subcutaneously in female Lewis rats. Dosing was begun 9 days after implantation and the plugs were harvested about one week later. The plugs were weighed, hydrolyzed, and the hydroxyproline content measured. Efficaciousness was determined by the comparison of the compound-treated groups with vehicle treated controls.

The compounds of Formula I exhibited the ability to inhibit the degradation of the cartilage plugs in this assay.

Example 45

In Vivo Assay Procedure

45A. Determination of TNF Production Following LPS Stimulation

Female Balb/c mice, 6–8 weeks old (Jackson Labs or Harlan) were used. For each treatment group, 6–8 mice were used Mice were injected I.P. with LPS (Sigma, 13129, 10–20 µg/mouse) after treatment with a compound of Formula I. The compound of Formula I or vehicle was administered subcutaneously (S.C.) once, 30–60 minutes prior to LPS challenge. Control animals received CMC vehicle alone or CMC+2–5% DMSO. Animals were bled 1.5 hours after LPS injection under anesthesia with metofane from the retroorbital plexus, using a Pasteur pipette Blood was collected in a microtainer serum separator tube (Becton Dickinson #5960). The sera were separated and either tested the next day or they were kept at −20° C. until ready to test for TNF-α.

45B. ELISA Assay for Murine TNF-A

The Endogen (EM-TNFA kit, Endogen, Woburn, Mass.) mouse tumor necrosis factor alpha (mTNF-α) kit is an in vitro enzyme-linked immunosorbent assay for the quantitative measurement of mouse TNF-α. Standards (lyophilized recombinant *E. coli*-derived mouse TNF-α) or serum samples (50 μl each) were added in duplicate to each well of the precoated anti-mTNF-α plate. Biotinylated antibody (50 μl) was added, the plates were incubated for 2–3 hours at room temperature. The wells were washed five times with wash buffer and 100 μl of diluted strepavidin HRP were added to each well and then were incubated at room temperature for 30 minutes. After washing (5×), 100 μl premixed TMB substrate solution were added to each well and plates were developed at room temperature in the dark for 30 minutes. The reaction was stopped by adding 100 μl of the stop solution. Absorbance at 450–575 nm was measured in a plate reader (ThermoMax, Molecular Devices). Results are calculated at pg/ml TNF-α by comparison to the standard curve, using Immunofit Beckman software. They are expressed as mean pg/ml of TNF-α, and as percentage of inhibition compared to controls (animals injected with LPS alone), considered 100% of TNF-α production.

The compounds of Formula I, when tested in this assay, exhibited the ability to inhibit TNF-α production.

Example 46

TNF Conjugate Immunoassay

Human Monomac 6 cells were cultured at 37° C. in RPMI 1640 medium supplemented with 10% fetal calf serum to a density of 1×10⁵ cells/mL. All subsequent incubations were performed at 37° C. 230 μl of these cells were placed in each well of a 96-well tissue culture plate and the cells incubated for 15 minutes. 10 μl of desired concentration of compounds of Formula I in the above mentioned medium were added to the appropriate wells and incubated for an additional 15 minutes. To each well was added 10 μl of an LPS/PMA mixture which brings the final concentration of LPS to 10 ng/mL and the final PMA concentration to 30 ng/mL. The cells were then incubated for 2 hours after which the plate was centrifuged and the medium removed and analyzed for TNF content. The analysis was performed using an R & D Systems TNF Quantikine Immunoassay (Catalog No. DTA50, R & D Systems, Minneapolis, Minn.) and following the manufacturer's protocol. The IC$_{50}$ was calculated from the percent inhibition of TNF released into the medium.

The compounds of Formula I, when tested in this assay, exhibited the ability to inhibit TNF production.

Example 47

TNFR Shedding Immunoassay

Human Monomac 6 cells are cultured to a density of 1×10⁶ cells/mL at 37° C. in RPMI 1640 medium supplemented with 10% fetal calf serum. All subsequent incubations are performed at 37° C. 230 μl of these cells are placed in each well of a 96-well tissue culture plate and the cells are incubated for 15 minutes. 10 μl of desired concentration of compounds of Formula I in the above mentioned medium are added to the appropriate wells and incubated for an additional 15 minutes. To each well is added 10 μl of PMA at a final concentration of 30 ng/mL. The cells are then incubated for 16 hours after which the plate is centrifuged and the medium is removed and analyzed for TNF receptor content. The analysis is performed using an R & D Systems TNF receptor Quantikine Immunoassay following the manufacturer's protocol. Measurements of each TNF receptor (receptor I and receptor II) are performed in this way. The IC$_{50}$ is calculated from the percent inhibition of TNF released into the medium.

The compounds of Formula I, when tested in this assay, exhibited the ability to selectively inhibit TNF production.

While the present invention has been described with respect to specific embodiments thereof, it will be understood by those skilled in the art that various changes may be made and equivalents may be substituted without departing from the true spirit and scope of the invention. All such modifications are intended to be within the scope of the claims appended hereto.

What is claimed is:

1. A compound of the formula:

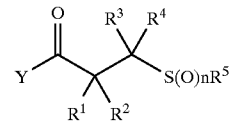

wherein:

n is 0, 1 or 2;

Y is hydroxy or XONH—, where X is hydrogen or lower alkyl;

R$^1$ is hydrogen or lower alkyl;

R$^2$ is hydrogen, lower alkyl, heteroalkyl, aryl, aralkyl, arylheteroalkyl, cycloalkyl, cycloalkylalkyl, heteroaryl, heteroaralkyl, heteroarylheteroalkyl, heterocyclo, heterocylo-lower alkyl, heterocyclo-lower heteroalkyl or —NR$^6$R$^7$, wherein:

R$^6$ is hydrogen, lower alkyl, cycloalkyl or cycloalkylalkyl, aryl, heteroaryl and heteroaralkyl;

R$^7$ is hydrogen, lower alkyl, cycloalkyl or cycloalkylalkyl, aryl, aralkyl, heteroaryl, heteroaralkyl, —C(O)R$^8$, —C(O)NR$^8$R$^9$, —SO$_2$NR$^8$R$^9$, —SO$_2$R$^{10}$, aryloxycarbonyl, or alkoxycarbonyl; or R$^6$ and R$^7$ together with the nitrogen atom to which they are attached represent a heterocyclo group; wherein R$^8$ and R$^9$ are independently hydrogen, lower alkyl, cycloalkyl, cycloalkylalkyl, aryl, aralkyl, heteroaryl, heteroaralkyl or heteroalkyl; and R$^{10}$ is lower alkyl, cycloalkyl, cycloalkylalkyl, aryl, aralkyl, heteroaryl, heteroaralkyl, heteroalkyl or heterocyclo; or R$^1$ and R$^2$ together with the carbon atom to which they are attached represent a cycloalkyl or heterocyclo group;

R$^3$ is hydrogen, lower alkyl, cycloalkyl, cycloalkylalkyl, aryl, aralkyl, heteroaryl, heteroaralkyl, heteroalkyl or lower alkoxy;

R$^4$ is hydrogen, lower alkyl, cycloalkyl or cycloalkylalkyl; or

R² and R³ together with the carbons to which they are attached represent a cycloalkyl or heterocyclo group; or R³ and R⁴ together with the carbon to which they are attached represent a cycloalkyl or heterocyclo group; and R⁵ is lower alkyl, cycloalkyl, cycloalkylalkyl, aryl, aralkyl, heteroaryl or heteroaralkyl;

or a pharmaceutically acceptable salt or ester thereof provided that:

(a) when n=O, then Y=XONH; and (b) when Y=OH and n=1 or 2, then (i) $R_1$ and $R_2$ or $R_3$ and $R_4$, together with the carbons to which they are attached form a heterocyclo group; or (ii) $R_1$ is lower alkyl, and $R_2$ is heteroalkyl, arylheteroalkyl, cycloalkyl, cycloalkylalkyl, heteroaryl, heteroaralkyl, heterocyclo, heterocyclo-lower alkyl or heterocyclo-lower heteroalkyl.

2. A compound of claim 1, wherein R² is —NR⁶R⁷.

3. The compound of claim 1, wherein n is 2 and Y is XONH— in which X is hydrogen, or a pharmaceutically acceptable salt thereof.

4. The compound of claim 3, wherein R¹ is hydrogen and R⁵ is aryl or heteroaryl, or a pharmaceutically acceptable salt thereof.

5. The compound of claim 4, wherein R² is hydrogen and R³ is aralkyl and R⁴ is hydrogen, or a pharmaceutically acceptable salt thereof.

6. The compound of claim 5, wherein R³ is benzyl and R⁵ is optionally substituted phenyl or naphthyl, or a pharmaceutically acceptable salt thereof.

7. The compound of claim 6, wherein R⁵ is phenyl, 4-methoxyphenyl, 1-(4-methoxyphenyl)-2-phenylethene, phenylthiophenyl, phenoxyphenyl, or biphenyl, or a pharmaceutically acceptable salt thereof.

8. The compound of claim 7, wherein R⁵ is 4-phenylthiophenyl, 4-phenoxyphenyl, or 4-biphenyl, or a pharmaceutically acceptable salt thereof.

9. The compound of claim 4, wherein R³ and R⁴ together with the carbon to which they are attached form a cycloalkyl group, or a pharmaceutically acceptable salt thereof.

10. The compound of claim 9, wherein R⁵ is 4-methoxyphenyl or 4-phenoxyphenyl and the cycloalkyl group is cyclopentyl, cyclohexyl, or 4-methylcyclohexyl, or a pharmaceutically acceptable salt thereof.

11. The compound of claim 4, wherein R³ and R⁴ together with the carbon to which they are attached form a heterocyclo group, or a pharmaceutically acceptable salt thereof.

12. The compound of claim 11, wherein the heterocyclo group is optionally substituted piperidine or tetrahydropyranyl, or a pharmaceutically acceptable salt thereof.

13. The compound of claim 12, wherein the heterocyclo group is piperidin-4-yl and R⁵ is 4-phenoxyphenyl, 4-(4-bromophenoxy)phenyl, 4-(4-chlorophenoxy)phenyl, or 4-(4-fluorophenoxy)phenyl, or a pharmaceutically acceptable salt thereof.

14. The compound of claim 12, wherein the heterocyclo group is 1-methylpiperidin-4-yl and R is 4-phenoxyphenyl, 4-(4-bromophenoxy)phenyl, 4-(4-chlorophenoxy)phenyl, or 4-(4-fluorophenoxy)phenyl, or a pharmaceutically acceptable salt thereof.

15. The compound of claim 12, wherein the heterocyclo group is 1-(cyclopropylmethyl)piperidin-4-yl and R⁵ is 4-phenoxyphenyl, 4-(4-bromophenoxy)phenyl, 4-(4-chlorophenoxy)phenyl, or 4-(4-fluorophenoxy)phenyl, or a pharmaceutically acceptable salt thereof.

16. The compound of claim 12, wherein the heterocyclo group is tetrahydropyran-4-yl and R⁵ is 4-phenoxyphenyl, 4-(4-bromophenoxy)phenyl, 4-(4-chlorophenoxy)phenyl, or 4-(4-fluorophenoxy)phenyl, or a pharmaceutically acceptable salt thereof.

17. The compound of claim 12, wherein the heterocyclo group is tetrahydropyran-4-yl, R² is hydrogen and R⁵ is 4-phenoxyphenyl, namely N-hydroxy-2-[4-(4-phenoxyphenylsulfonyl)tetrahydropyran-4-yl]-acetamide, or a pharmaceutically acceptable salt thereof.

18. The compound of claim 12, wherein the heterocyclo group is tetrahydropyran-4-yl, R² is hydrogen, and R⁵ is 4-(4-chlorophenoxy)phenyl, namely 2-{4-[4-(4-chlorophenoxy)phenylsulfonyl]-tetrahydropyran-4-yl}-N-hydroxyacetamide, or a pharmaceutically acceptable salt thereof.

19. The compound of claim 12, wherein the heterocyclo group is tetrahydropyran-4-yl, R² is hydrogen, and R⁵ is 4-(4-fluorophenoxy)phenyl, namely 2-{4-[4-(4-fluorophenoxy)phenylsulfonyl]-tetrahydropyran-4-yl}-N-hydroxyacetamide, or a pharmaceutically acceptable salt thereof.

20. The compound of claim 3, wherein R² and R³ together with the carbons to which they are attached form a cycloalkyl group and R⁵ is aryl, or a pharmaceutically acceptable salt thereof.

21. The compound of claim 20, wherein the cycloalkyl group is cyclopentyl or cyclohexyl, R⁴ is hydrogen, and R⁵ is 4-methoxyphenyl, or a pharmaceutically acceptable salt thereof.

22. The compound of claim 3, wherein R² is —NR⁶R⁷, R¹, R³ and R⁴ are hydrogen, and R⁵ is aryl, or a pharmaceutically acceptable salt thereof.

23. The compound of claim 22, wherein R⁵ is 4-phenoxyphenyl, 4-(4-chlorophenoxy)phenyl, or 4-(4-fluorophenoxy)phenyl, or a pharmaceutically acceptable salt thereof.

24. The compound of claim 23, wherein R⁵ is 4-phenoxyphenyl, R⁶ is hydrogen and R⁷ is CBZ-(S)-valinamido, namely (R)-2-(CBZ-valinamido)-N-hydroxy-3-(4-phenoxyphenylsulfonyl)-propionamide, or a pharmaceutically acceptable salt thereof.

25. The compound of claim 23, wherein R⁵ is 4-phenoxyphenyl, R⁶ is hydrogen and R⁷ is (S)-valinamido, namely (R)-N-hydroxy-2-valinamido-3-(4-phenoxyphenylsulfonyl)-propionamide, or a pharmaceutically acceptable salt thereof.

26. The compound of claim 23, wherein R⁵ is 4-phenoxyphenyl, and R⁶ and R¹ are both methyl, namely (R)-2-dimethylamino-N-hydroxy-3-(4-phenoxyphenylsulfonyl)-propionamide, or a pharmaceutically acceptable salt thereof.

27. The compound of claim 23, wherein R⁵ is 4-phenoxyphenyl, R⁶ is hydrogen, and R⁷ is dimethylaminosulfonyl, namely (R)-2-dimethylaminosulfonamido-N-hydroxy-3-(4-phenoxyphenylsulfonyl)-propionamide, or a pharmaceutically acceptable salt thereof.

28. The compound of claim 3, wherein R¹ and R² together with the carbon to which they are attached form a heterocyclo group, or a pharmaceutically acceptable salt thereof.

29. The compound of claim 28, wherein R³ and R⁴ are both hydrogen and the heterocyclo group is optionally substituted piperidine or tetrahydropyranyl, or a pharmaceutically acceptable salt thereof.

30. The compound of claim 29, wherein the heterocyclo group is piperidin-4-yl and $R^5$ is 4-phenoxyphenyl, 4-(4-bromophenoxy)phenyl, 4-(4-chlorophenoxy)phenyl, or 4-(4-fluorophenoxy)phenyl, or a pharmaceutically acceptable salt thereof.

31. The compound of claim 29, wherein the heterocyclo group is tetrahydropyran-4-yl and $R^5$ is 4-phenoxyphenyl, 4-(4-bromophenoxy)phenyl, 4-(4-chlorophenoxy)phenyl, 4-(4-fluorophenoxy)phenyl, 4-(thiophen-2-yl)phenoxyphenyl, 4-(thiophen-3-yl)phenoxyphenyl, 4-(2-pyridyloxy)phenyl, 4-(5-chloro-2-pyridyloxy)phenyl, or a pharmaceutically acceptable salt thereof.

32. The compound of claim 31, wherein $R^5$ is 4-(4-chlorophenoxy)phenyl, namely 4-[4-(4-chlorophenoxy)phenylsulfonylmethyl]-tetrahydropyran-4-(N-hydroxycarboxamide), or a pharmaceutically acceptable salt thereof.

33. The compound of claim 31, wherein $R^5$ is 4-(thiophen-2-yl)phenoxyphenyl, namely 4-[4-(4-thiophen-2-yl)phenoxyphenylsulfonylmethyl]-tetrahydropyran-4-(N-hydroxycarboxamide), or a pharmaceutically acceptable salt thereof.

34. The compound of claim 3, wherein $R^1$ and $R^2$ are both alkyl, $R^3$ and $R^4$ are hydrogen, and $R^5$ is 4-phenoxyphenyl, 4-(4-bromophenoxy)phenyl, 4-(4-chlorophenoxy)phenyl, or 4-(4-fluorophenoxy)phenyl, or a pharmaceutically acceptable salt thereof.

35. The compound of claim 34, wherein $R^1$ and $R^2$ are both methyl, $R^5$ is 4-(4-chlorophenoxy)phenyl, namely 3-[4-(4-chlorophenoxy)phenylsulfonyl]-2,2-dimethyl-N-hydroxypropionamide, or a pharmaceutically acceptable salt thereof.

36. A process for preparing a compound of the Formula:

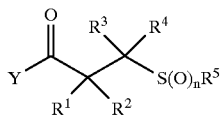

wherein:

n is 1 or 2;

Y is hydroxy or XONH—, where X is hydrogen or lower alkyl;

$R^1$ is hydrogen or lower alkyl;

$R^2$ is hydrogen, lower alkyl, aralkyl, cycloalkyl, cycloalkylalkyl, or heterocyclo; or $R^1$ and $R^2$ together with the carbon atom to which they are attached represent a cycloalkyl or heterocyclo group;

$R^3$ is hydrogen, lower alkyl, cycloalkyl, cycloalkylalkyl, aralkyl, heteroaralkyl, or lower alkoxy;

$R^4$ is hydrogen or lower alkyl; or $R^2$ and $R^3$ together with the carbons to which they are attached represent a cycloalkyl or heterocyclo group; or $R^3$ and $R^4$ together with the carbon to which they are attached represent a cycloalkyl or heterocyclo group; and $R^5$ is lower alkyl, aryl, aralkyl, heteroaryl, or heteroaralkyl; comprising contacting a compound of the Formula:

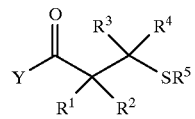

with an oxidizing agent.

37. The process of claim 36, wherein the oxidizing agent is OXONE.

38. The process of claim 37, wherein the reaction is carried out in a mixture of methanol, tetrahydrofuran and water.

39. The process of claim 38, wherein n is 2, $R^1$ and $R^2$ taken together with the carbon to which they are attached is tetrahydropyran-4-yl, $R^3$ and $R^4$ are both hydrogen, $R^5$ is 4-(4-chlorophenoxy)-phenyl, and Y is XONH—, in which X is hydrogen.

40. The process of claim 36, wherein the compound of Formula:

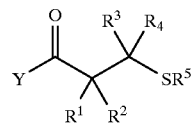

in which $R^1$, $R^2$, $R^3$, $R^4$, $R^5$ and Y are as defined;

is prepared by contacting a compound of the Formula:

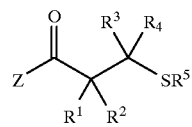

in which $R^1$, $R^2$, $R^3$, $R^4$, and $R^5$ are as defined and Z is chloro, bromo or iodo, which N,O-bis(trimethylsilyl)hydroxylamine or aqueous hydroxylamine.

41. The process of claim 40, wherein Z is chloro and the reactant is aqueous hydroxyl amine.

42. The process of claim 41, wherein the reaction is carried out in a solvent comprising a mixture of tert-butanol and tetrahydrofuran.

43. The process of claim 42, wherein $R^1$ and $R^2$ taken together with the carbon to which they are attached is tetrahydropyran-4-yl, $R^3$ and $R^4$ are both hydrogen, $R^5$ is 4-(4-chlorophenoxy)-phenyl, and Y is XONH—, in which X is hydrogen.

44. The process of claim 40, wherein the compound of Formula:

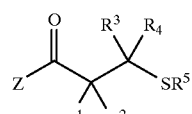

in which $R^1$, $R^2$, $R^3$, $R^4$, $R^5$, and Z are as defined;

is prepared by contacting a compound of the Formula:

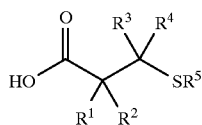

in which $R^1$, $R^2$, $R^3$, $R^4$, $R^5$ are as defined;
with a halogenating agent.

45. The process of claim 44, wherein the halogenating agent is oxalyl chloride.

46. The process of claim 44, wherein the compound of Formula:

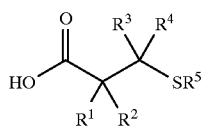

in which $R^1$, $R^2$, $R^3$, $R^4$, $R^5$ are as defined;
is prepared by reacting a compound of the Formula:

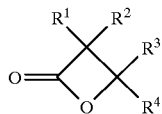

in which $R^1$, $R^2$, $R^3$, and $R^4$ are as defined;
with an anion of a compound of Formula $R^5SH$, where $R^5$ is as defined.

47. The process of claim 46, wherein the anion is prepared by reacting $R^5SH$ with sodium hydride.

48. The process of claim 47, wherein the solvent is tetrahydrofuran.

49. The process of claim 48, wherein $R^1$ and $R^2$ taken together with the carbon to which they are attached is tetrahydropyran-4-yl, $R^3$ and $R^4$ are both hydrogen, and $R^5$ is 4-(4-chlorophenoxy)phenyl.

50. The process of claim 46, wherein the compound of Formula:

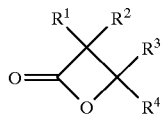

in which $R^1$, $R^2$, $R^3$, and $R^4$ are as defined;
is prepared by reacting a compound of the Formula:

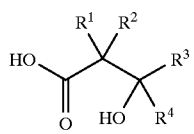

in which $R^1$, $R^2$, $R^3$, and $R^4$ are as defined;
with a dehydrating agent.

51. The process of claim 50, wherein the dehydrating agent is trifluoromethanesulfonic anhydride, methanesulfonic anhydride, methanesulfonyl chloride, or benzenesulfonyl chloride, and the reaction is carried out in diethyl ether or dichloromethane as a solvent, in the presence of a tertiary base and optionally 4-dimethylaminopyridine.

52. The process of claim 51, wherein the dehydrating agent is benzenesulfonyl chloride, the solvent is dichloromethane, the tertiary base is triethylamine, and 4-dimethylaminopyridine is present.

53. The process of claim 52, wherein $R^1$ and $R^2$ taken together with the carbon to which they are attached is tetrahydropyran-4-yl, and $R^3$ and $R^4$ are both hydrogen.

54. The process of claim 50, wherein the compound of Formula:

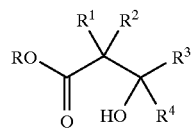

in which $R^1$ and $R^2$ are as defined and $R^3$ and $R^4$ are both hydrogen;
is prepared by reacting a compound of the Formula:

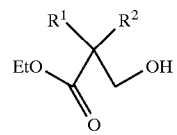

in which $R^1$ and $R^2$ are as defined;
with a selective reducing agent in an inert solvent.

55. The process of claim 54, wherein the selective reducing agent is diisobutylaluminum hydride and the inert solvent is toluene.

56. A pharmaceutical composition comprising a pharmaceutically acceptable non-toxic excipient and a therapeutically effective amount of a compound of claim 1, or a pharmaceutically acceptable salt thereof.

57. A method for treating a mammal having a disease-state which is alleviated by treatment with a matrix metalloprotease inhibitor, which method comprises administering to a mammal in need of such treatment a therapeutically effective amount of a compound of claim 1, or a pharmaceutically acceptable salt thereof.

58. The method of claim 57, wherein the disease state is rheumatoid arthritis, osteoarthritis, osteoporosis, periodontal disease, aberrant angiogenesis, multiple sclerosis, tumor metastasis, or corneal ulceration.

59. The method of claim 57, wherein the disease state is mediated by tumor necrosis factor.

60. The method of claim 59, wherein the disease state is inflammation, hemorrhage, graft versus host reaction, or an autoimmune disease.

* * * * *